US010214572B2

(12) United States Patent
Boye et al.

(10) Patent No.: US 10,214,572 B2
(45) Date of Patent: Feb. 26, 2019

(54) DUAL-AAV VECTOR-BASED SYSTEMS AND METHODS FOR DELIVERING OVERSIZED GENES TO MAMMALIAN CELLS

(71) Applicant: University of Florida Research Foundation, Inc., Gainesville, FL (US)

(72) Inventors: Sanford Leon Boye, Gainesville, FL (US); Shannon Elizabeth Boye, Gainesville, FL (US); Frank Markus Dyka, Gainesville, FL (US); William W. Hauswirth, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 200 days.

(21) Appl. No.: 14/279,142

(22) Filed: May 15, 2014

(65) Prior Publication Data
US 2014/0256802 A1 Sep. 11, 2014

Related U.S. Application Data

(63) Continuation of application No. PCT/US2012/065645, filed on Nov. 16, 2012.

(60) Provisional application No. 61/560,437, filed on Nov. 16, 2011.

(51) Int. Cl.
*C07K 14/47* (2006.01)
*A61K 48/00* (2006.01)
*C12N 15/86* (2006.01)

(52) U.S. Cl.
CPC .......... *C07K 14/47* (2013.01); *A61K 48/0066* (2013.01); *C12N 15/86* (2013.01); *C07K 14/4716* (2013.01); *C12N 2750/14143* (2013.01); *C12N 2800/40* (2013.01); *C12N 2830/50* (2013.01); *C12N 2840/445* (2013.01); *C12N 2999/007* (2013.01)

(58) Field of Classification Search
None
See application file for complete search history.

(56) References Cited

U.S. PATENT DOCUMENTS

2010/0003218 A1 1/2010 Duan et al.
2010/0266551 A1 10/2010 Richard et al.

FOREIGN PATENT DOCUMENTS

WO WO 2008/088895 A2 7/2008

OTHER PUBLICATIONS

Duan et al.; Expanding AAV Packaging Capacity with Trans-splicing or Overlapping Vectors: A Quantitative Comparison; Molecular Therapy vol. 4, No. 4, Oct. 2001.*
Jacobson et al.; Usher syndromes due to MYO7A, PCDH15, USH2A or GPR98 mutations share retinal disease mechanism; Human Molecular Genetics, 2008, vol. 17, No. 15; pp. 2405-2415.*
Human Myosin VIIA; Human myosin VIIA (USH1B) mRNA, complete cds; GenBank: U39226.1; http://www.ncbi.nlm.nih.gov/nuccore/U39226; pp. 1-5; available Jul. 11, 1996.*
Li et al.; High-Efficiency Transduction of Fibroblasts and Mesenchymal Stem Cells by Tyrosine-Mutant AAV2 Vectors for Their Potential Use in Cellular Therapy; Human Gene Therapy; 21: 1527-1543; published online Sep. 29, 2010.*
International Search Report and Written Opinion for International Application No. PCT/US2012/065645 dated Mar. 29, 2013.
International Preliminary Report on Patentability for International Application No. PCT/U52012/065645 dated May 30, 2014.
Allocca et al., Serotype-dependent packaging of large genes in adeno-associated viral vectors results in effective gene delivery in mice. J Clin Invest. May 1, 2008; 118(5): 1955-1964. Published online Apr. 15, 2008. doi: 10.1172/JCI34316.
Dong et al., Characterization of genome integrity for oversized recombinant AAV vector. Mol Ther. Jan. 2010;18(1):87-92. doi: 10.1038/mt.2009.258. Epub Nov. 10, 2009.
Lai et al., Evidence for the Failure of Adeno-associated Virus Serotype 5 to Package a Viral Genome ∓8.2 kb. Mol Ther. 2010; 18 1, 75-79. doi:10.1038/mt.2009.256.
Wu et al., Effect of genome size on AAV vector packaging. Mol Ther. Jan. 2010;18(1):80-6. doi: 10.1038/mt.2009.255. Epub Nov. 10, 2009.

(Continued)

*Primary Examiner* — Antonio Galisteo Gonzalez
(74) *Attorney, Agent, or Firm* — Wolf, Greenfield & Sacks, P.C.

(57) ABSTRACT

Disclosed are materials and methods for treating diseases of the mammalian eye, and in particular, Usher syndrome 1B (USH1B). The invention provides AAV-based, dual-vector systems that facilitate the expression of full-length proteins whose coding sequences exceed that of the polynucleotide packaging capacity of an individual AAV vector. In one embodiment, vector systems are provided that include i) a first AAV vector polynucleotide that includes an inverted terminal repeat at each end of the polynucleotide and a suitable promoter followed by a partial coding sequence that encodes an N-terminal portion of a full-length polypeptide; and ii) a second AAV vector polynucleotide that includes an inverted terminal repeat at each end of the polynucleotide and a partial coding sequence that encodes a C-terminal portion of a full-length polypeptide, optionally followed by a polyadenylation (pA) signal sequence. In another embodiment, the vector system includes i) a first AAV vector polynucleotide comprising an inverted terminal repeat at each end, a suitable promoter followed by a partial coding sequence that encodes an N-terminal portion of a full-length polypeptide followed by a splice donor site and intron and ii) a second AAV vector polynucleotide comprising an inverted terminal repeat at each end, followed by an intron and a splice-acceptor site for the intron, followed by a partial coding sequence that encodes a C-terminal portion of a full-length polypeptide, optionally followed by a polyadenylation (pA) signal sequence. The coding sequence or the intron sequence in the first and second AAV vectors preferably includes a sequence region that overlaps.

7 Claims, 26 Drawing Sheets
(13 of 26 Drawing Sheet(s) Filed in Color)
Specification includes a Sequence Listing.

(56) References Cited

OTHER PUBLICATIONS

Yan et al., Inverted terminal repeat sequences are important for intermolecular recombination and circularization of adeno-associated virus genomes. J Virol. Jan. 2005;79(1):364-79.
Duan et al., Circular intermediates of recombinant adeno-associated virus have defined structural characteristics responsible for long-term episomal persistence in muscle tissue. J Virol. Nov. 1998;72(11):8568-77.
Hashimoto et al., Lentiviral gene replacement therapy of retinas in a mouse model for Usher syndrome type 1B. Gene Therapy. 2007:14;584-594.

* cited by examiner

Untreated

Treated

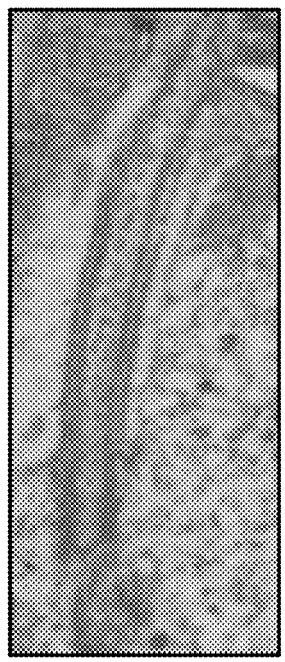 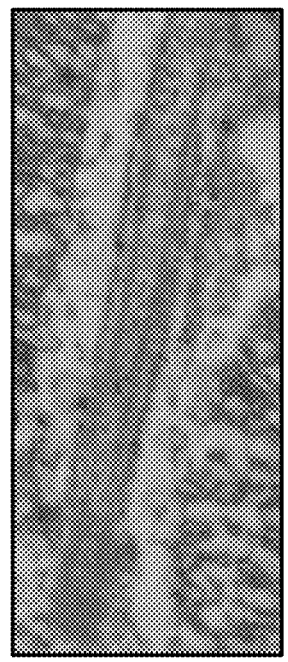 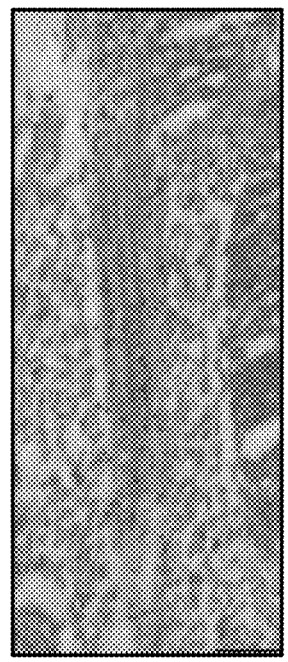
FIG. 11A     FIG. 11B     FIG. 11C
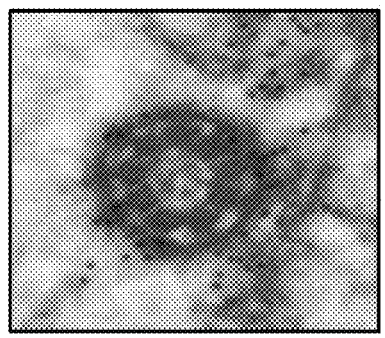 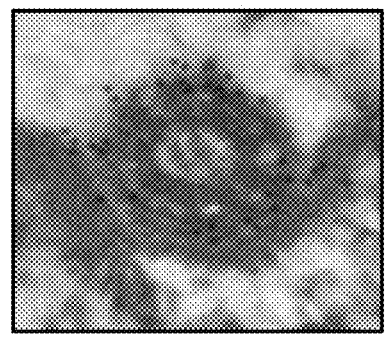
FIG. 11D     FIG. 11E

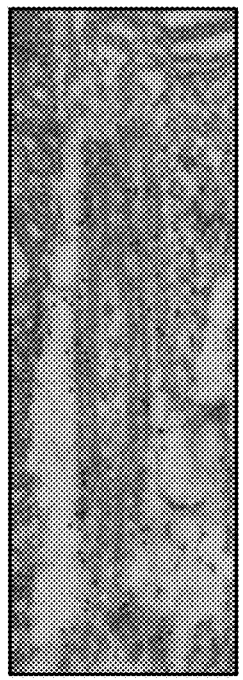 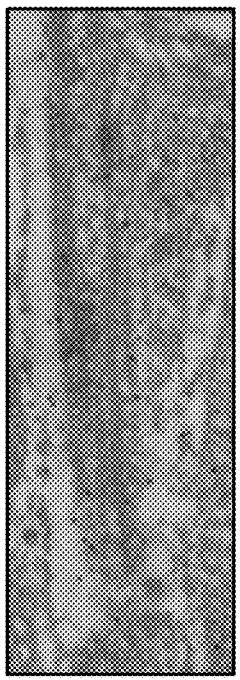 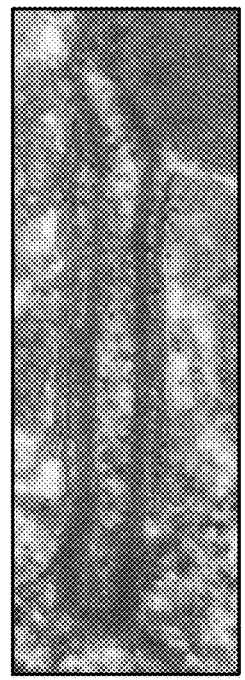 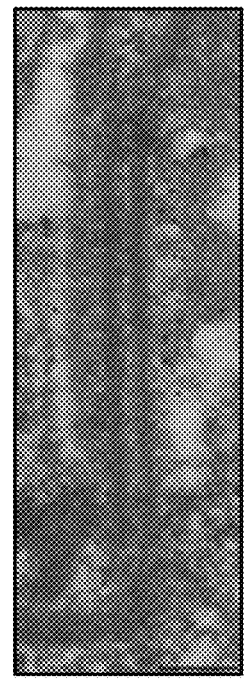
*FIG. 18A*  *FIG. 18B*  *FIG. 18C*  *FIG. 18D*
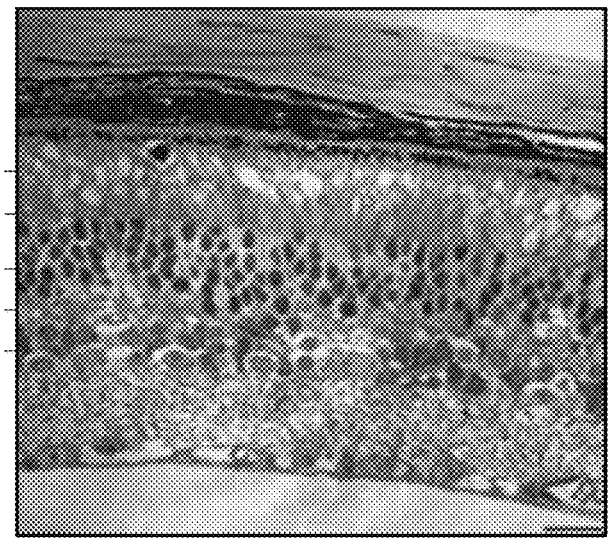
*FIG. 19*

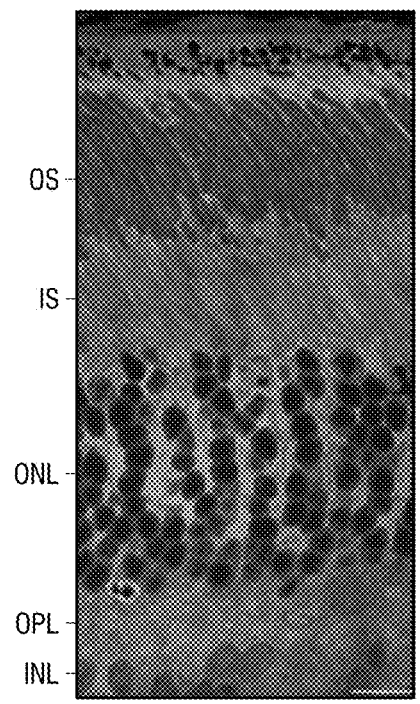
FIG. 20
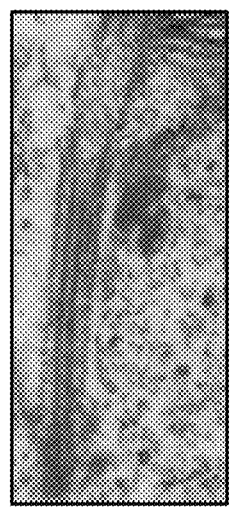 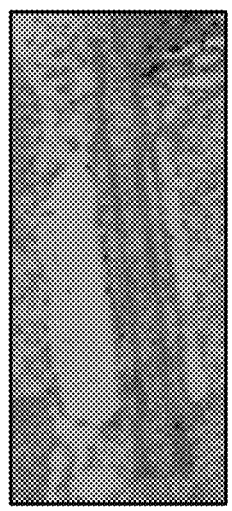 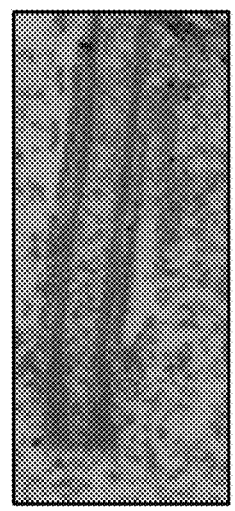 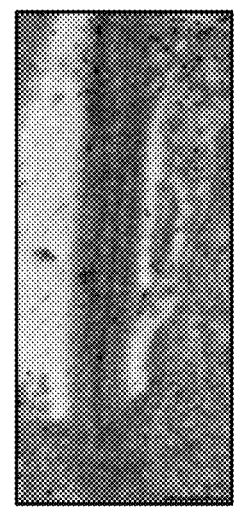
FIG. 21A  FIG. 21B  FIG. 21C  FIG. 21D

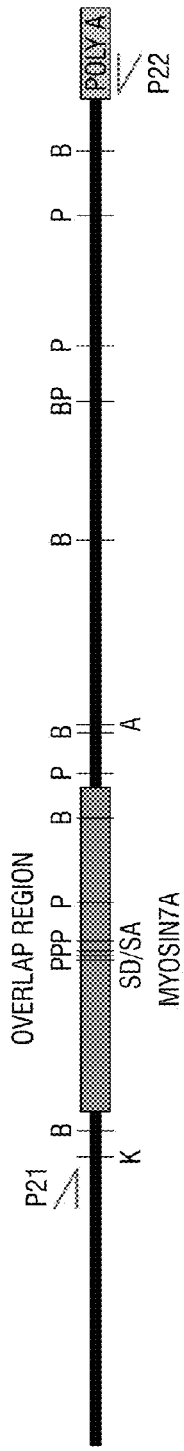
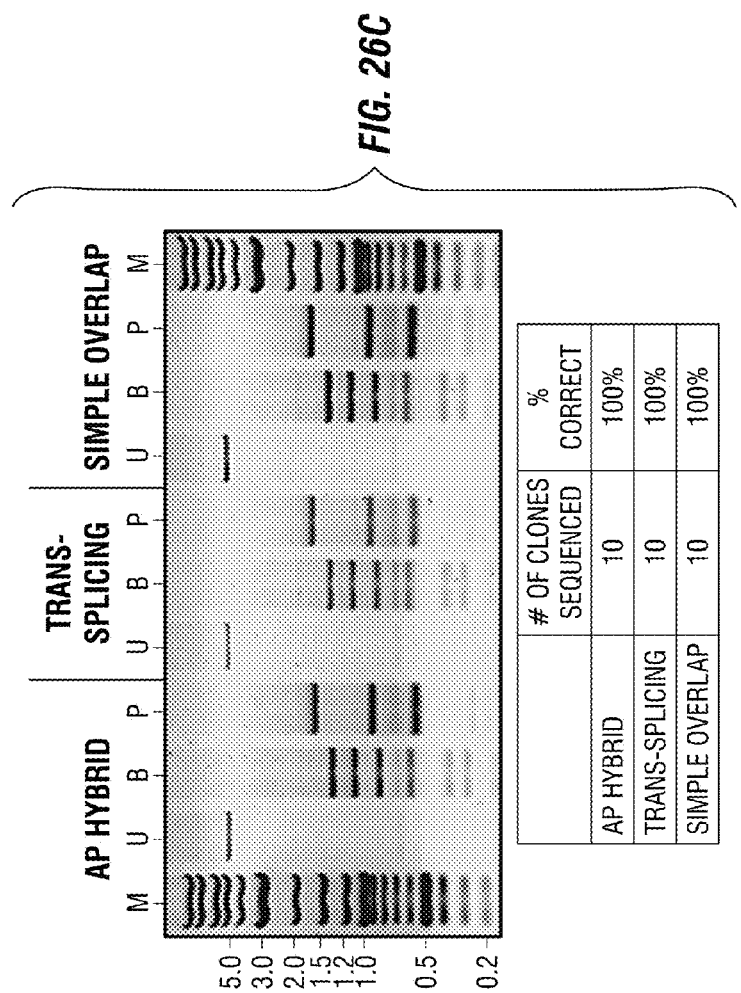
FIG. 26B
FIG. 26C

DUAL-AAV VECTOR-BASED SYSTEMS AND METHODS FOR DELIVERING OVERSIZED GENES TO MAMMALIAN CELLS

CROSS-REFERENCE TO RELATED APPLICATIONS

The present application is a continuation of PCT Intl. Patent Appl. No. PCT/US2012/065645 filed Nov. 16, 2012 (nationalized), which claimed priority to U.S. Provisional Patent Appl. No. 61/560,437, filed Nov. 16, 2011; the contents of each of which is hereby incorporated in its entirety by express reference thereto.

STATEMENT REGARDING FEDERALLY SPONSORED RESEARCH OR DEVELOPMENT

This invention was made with government support under grant numbers EY00331 and EY021721 awarded by the National Institutes of Health. The government has certain rights in the invention.

NAMES OF THE PARTIES TO A JOINT RESEARCH AGREEMENT

Not Applicable.

BACKGROUND OF THE INVENTION

Field of the Invention

The present invention relates generally to the fields of molecular biology and virology, and in particular, to the development of gene delivery vehicles. Disclosed are improved rAAV dual-vector systems, and compositions useful in delivering a variety of nucleic acid segments, including those encoding therapeutic proteins polypeptides, peptides, antisense oligonucleotides, or ribozyme constructs to selected host cells for use in various gene-therapy regimens. Methods are also provided for preparing and using these modified rAAV-dual-vector based systems in a variety of viral-based gene therapies, and in particular, for the treatment and/or amelioration of symptoms of Myosin VII-deficiency, including, without limitation, the treatment of human Usher syndrome.

Description of Related Art

As has been established by a multitude of successful proof-of-concept studies, and various clinical trials, recombinant AAV has emerged as the most optimal gene delivery vehicle to treat retinal disease. However, one limitation of AAV is its relatively small DNA packaging capacity—approximately 4.7 kilobases (KB). Thus, standard AAV vector systems are unsuitable for addressing diseases in which large genes are mutated or otherwise dysfunctional. An example of such a disease is Usher syndrome.

The most common form of Usher syndrome, USH1B, is a severe autosomal-recessive, deaf-blindness disorder caused by mutations in the myosinVIIa gene. Blindness occurs from a progressive retinal degeneration that begins after deafness, and after development of the retina. MYO7a protein is expressed in photoreceptors and retinal pigment epithelium (RPE), and is involved in opsin transport through photoreceptor cilia and the movement of RPE melanosomes.

The coding region for the human Myosin VII protein (MYO7a), however, is 6534 or 6648 nucleotides in length (depending on the allelic variant), making traditional AAV vector systems unsuitable for gene therapy of USH1B.

Previously, Allocca et al. (2008) published intriguing results suggesting that AAV5 serotype vectors were capable of packaging genomes of up to 8.9 KB in size, and that these vectors expressed full-length proteins when delivered in vivo. In this study, the authors expressed full-length MYO7A protein from an AAV5 vector containing the CMV promoter driving hMyo7a. Subsequent studies, carried out to directly validate the Allocca et al. findings were simultaneously published by three independent groups (Lai et al., 2010; Dong et al., 2010; Wu et al., 2010), and their publication was accompanied by an expert commentary (See, Hirsch et al., 2010). While all three studies confirmed that these 'oversized' AAV5 vectors did indeed drive full-length protein expression, the genetic content of each vector capsid was found to be limited only to ~5 KB of DNA, and not the 8.7 KB originally reported by Allocca et al. (2008). These vector capsids were shown to contain a "heterogeneous mixture" of truncated vector genomes (e.g., the 5'-end of the gene, the 3'-end of the gene, or a mixture of the two, with an internal sequence deletion) (Lai et al., 2010; Dong et al., 2010; Wu et al., 2010). Additionally, these oversized/heterogeneous vectors exhibited poor packaging efficiency (i.e., low-vector titers) and low transduction efficiency when compared to matched reporter vectors of standard size (<5 KB) (Wu et al., 2010).

Using this 'heterogeneous' system, vectors containing portions of the MYO7A transgene were packaged, however, and proof-of-concept results were demonstrated in the shaker-1 mouse model of USH1B. The therapeutic results achieved with the heterogeneous AAV-hMyo7a vectors were comparable to previous gene replacement results using a Lentivirus-based hMyo7a vector (Hashimoto et al., 2007).

This Lentivirus-Myo7a vector is under development by Oxford BioMedica in collaboration with Sanofi-Aventis for a phase I/II clinical trial of USH1B, marketed under the name UshStat® LentiVector®. Lentivirus is regarded as a vector platform that is not well-suited for infecting post-mitotic (i.e., non-dividing) cells. Furthermore, although the vector is suitable for transducing RPE, many studies have shown it to be ineffective at transducing adult photoreceptors. Even though MYO7A is expressed in both cell types, UshStat® may only be effective at rescuing the RPE phenotype. A study showed that PRs are actually the initial site of disease, so not targeting this cell type effectively may result in zero therapy, although it remains to be seen in the human clinical trial.

Because of the excellent safety profile and encouraging reports of efficacy in the AAV gene therapy trials for LCA2/RPE65, there has been continuing interest in creating an AAV-based system for treating USH1B patients. However, the current AAV vector for MYO7A, as previously mentioned, is heterogeneous; it is manufactured and purified as a single-virus preparation containing a mixture of viral payloads. This fact, unfortunately, makes it virtually impossible to characterize the vector fully—a requirement for government regulatory review and approval. In order to address this concern directly (i.e., that the vector genome of any AAV-based vectors for USH1B must be fully characterized before gaining Food and Drug Administration (FDA) approval, the inventors have developed an AAV dual-vector-based system to facilitate gene therapy approaches for treating USH1B.

BRIEF SUMMARY OF THE INVENTION

The subject invention concerns materials and methods for gene therapy of diseases, such as Usher syndrome 1B (USH1B). The inventors have characterized dual vector platforms described herein as to transcript fidelity, and have shown and that mRNA arising from the system is 100% accurate relative to what would be predicted by correct homologous recombination on the front and back vector pairs, making them useful as gene therapy delivery vector systems.

One aspect of the invention concerns a dual AAV vector system that permits expression of full-length proteins, whose coding sequence exceeds the polynucleotide packaging capacity of an individual AAV vector.

In one embodiment, a vector system of the invention comprises:

(i) a first AAV vector polynucleotide comprising an inverted terminal repeat at each end of the polynucleotide, and a suitable promoter followed by a partial coding sequence that encodes an N-terminal part of a selected full-length polypeptide; and (ii) a second AAV vector polynucleotide comprising an inverted terminal repeat at each end of the polynucleotide, and a partial coding sequence that encodes a C-terminal part of the selected full-length polypeptide, optionally followed by a polyadenylation (pA) signal sequence.

The coding sequence in the first and second AAV vectors comprises sequence that overlaps, such that part of the coding sequence present at the 3'-end of the coding sequence of the first vector is identical or substantially identical with part of the coding sequence present at the 5'-end of the coding sequence of the second vector. In an illustrative embodiment, the polypeptide encoded is a wild type or biologically-functional human myosin VIIa polypeptide (hmyo7a).

In another embodiment, a vector system of the invention includes:

(i) a first AAV vector polynucleotide comprising an inverted terminal repeat at each end, a suitable promoter followed by a partial coding sequence that encodes an N-terminal part of a selected full-length polypeptide followed by a splice donor site for an intron and an intron; and (ii) a second AAV vector polynucleotide comprising an inverted terminal repeat at each end, followed by an intron and a splice acceptor site for the intron, followed by a partial coding sequence that encodes a C-terminal part of the selected full-length polypeptide, optionally followed by a polyadenylation (pA) signal sequence.

The intron sequence in the first and second AAV vectors includes a sequence that overlaps, such that all or part of the intron sequence present at the 3'-end of the coding sequence of the first vector is identical, or substantially identical, with all or part of the intron sequence present at the 5'-end of the coding sequence of the second vector. In one embodiment, the intron is intron 23 of the hmyo7a gene. In a specific embodiment, the polypeptide encoded is a wild type (i.e., functional) human myosin VIIa polypeptide, and the intron is the full intron 23 of the hmyo7a gene.

BRIEF DESCRIPTION OF THE DRAWINGS

For promoting an understanding of the principles of the invention, reference will now be made to the embodiments, or examples, illustrated in the drawings and specific language will be used to describe the same. It will, nevertheless be understood that no limitation of the scope of the invention is thereby intended. Any alterations and further modifications in the described embodiments, and any further applications of the principles of the invention as described herein are contemplated as would normally occur to one of ordinary skill in the art to which the invention relates.

The following drawings form part of the present specification and are included to demonstrate certain aspects of the present invention. The application contains at least one drawing that is executed in color. Copies of this patent or patent application publication with color drawing(s) will be provided by the Patent and Trademark Office upon request and payment of the necessary fee. The invention may be better understood by reference to the following description taken in conjunction with the accompanying drawings, in which like reference numerals identify like elements, and in which:

FIG. 10A is a diagram of the viral vector encoding human MYO7A cDNA. FIG. 10B is a western blot of WT eyecup (lane 1), primary RPE cultures derived from Myo7a-null mice and infected with AAV2-MYO7A (lane 2) or AAV5-MYO7A (lane 3), or not infected (lane 4), and primary RPE cultures derived from Myo7a$^{+/-}$ mice (lane 5). All lanes were immunolabeled with antibodies against actin (as a loading indicator of relative protein loading) and MYO7A. FIG. 10C, FIG. 10D, FIG. 10E, and FIG. 10F are immunofluorescence images of primary RPE cell cultures. Cells derived from Myo7a-null mice that were not infected (FIG. 10C), from Myo7a$^{+/-}$ mice (FIG. 10D), or from Myo7a-null mice infected with either 1×AAV2-MYO7A (FIG. 10E) or 1×AAV5-MYO7A (FIG. 10F). Scale=10 µm;

FIG. 11A, FIG. 11B, FIG. 11C, FIG. 11D, FIG. 11E, FIG. 11F, FIG. 11F-1, FIG. 11G, FIG. 11G-1, FIG. 11H, FIG. 11I, FIG. 11J, FIG. 11K, FIG. 11L, and FIG. 11M show the expression of MYO7A from single AAV2 and AAV5 vectors in vivo. FIG. 11A, FIG. 11B, FIG. 11C, FIG. 11D, and FIG. 11E show EM images of MYO7A immunogold labelling of the connecting cilium and pericilium from rod photoreceptors in a Myo7a-null retina. FIG. 11A is a longitudinal section from an untreated Myo7a-null retina (background label only). FIG. 11B and FIG. 11C are longitudinal sections from Myo7a-null retinas treated with AAV2-MYO7A (FIG. 11B) or AAV5-MYO7A (FIG. 11C). Scale=50 nm. FIG. 11D and FIG. 11E are transverse sections of connecting cilia from rod photoreceptors in Myo7a-null retinas treated with AAV2-MYO7A (FIG. 11D) or AAV5-MYO7A (FIG. 11E). Scale=50 nm. FIG. 11F and FIG. 11G show EM images of RPE cells from Myo7a-null retinas treated with AAV2-MYO7A (FIG. 11F) or AAV5-MYO7A (FIG. 11G). Scale=500 nm. BM=Bruch's membrane, AP=apical processes. Areas indicated by rectangles are enlarged in FIG. 11F-1 and FIG. 11G-1 to show MYO7A immunogold labeling (indicated by circles). Scale=50 nm. FIG. 11H and FIG. 11I show EM image of a longitudinal section of the connecting cilium and pericilium from a rod (FIG. 11H) and a cone (FIG. 11I) photoreceptor in a Myo7a-null retina, treated with AAV2-MYO7A. The section was double-labeled with MYO7A (12-nm gold) and rod opsin (15-nm gold) antibodies. Rod outer segments were labeled with the opsin antibody, while cones were identified by lack of rod opsin labeling in their outer segments. The sections show just the base of the outer segments. Nearly all the label in the connecting cilium is MYO7A, even in the rod. Scale=50 nm. FIG. 11J, FIG. 11K, FIG. 11L, and FIG. 11M are bar graphs indicating MYO7A immunogold particle density in the rod photoreceptor cilium and pericilium (FIG. 11J and FIG. 11K) and in the RPE (FIG. 11L and FIG. 11M), following treatment with AAV2-MYO7A (FIG. 11J and FIG. 11L) or AAV5-MYO7A (FIG. 11K and FIG. 11M) of different concentrations. n=3 animals per condition. Bars indicate SEM;

FIG. 12E illustrates a region distant from injection site, where all RPE cells lacked melanosomes in their apical processes. Brackets on left side indicate RPE apical processes. Scale=25 µm. FIG. 12F is a diagram of an eyecup, indicating the relative locations of the images shown in FIG. 12A, FIG. 12B, FIG. 12C, FIG. 12D, and FIG. 12E. Arrow indicates the site of injection; ONH indicates the optic nerve head;

FIG. 14A-1, FIG. 14A-2, FIG. 14B, FIG. 14C, FIG. 14D, FIG. 14E, FIG. 14F, and FIG. 14G show the expression of MYO7A from the overlapping AAV2-MYO7A dual vectors. FIG. 14A-1 and FIG. 14A-2 illustrate a diagram of the overlapping AAV2-MYO7A dual vectors. The overlapping region contains 1365 bases. FIG. 14B is a Western blot of proteins from primary RPE cultures derived from Myo7a-null mice and not infected (lane 1), or infected with AAV2-MYO7A(dual) (lane 2); primary RPE cultures derived from Myo7a$^{+/-}$ mice (lane 3); WT eyecup (lane 4); HEK293A cells transfected with pTR-smCBA-MYO7A (lane 5). All lanes were immunolabeled with anti-MYO7A and anti-actin. FIG. 14C, FIG. 14D, FIG. 14E, and FIG. 14F show immunofluorescence of cultured RPE cells transduced with AAV2-MYO7A(dual). FIG. 14C, FIG. 14D, and FIG. 14E show primary RPE cultures derived from Myo7a-null mice and ARPE19 (FIG. 14F) cells. Scale=10 µm. FIG. 14G is a bar graph indicating the distribution of MYO7A immunogold particle density among RPE cells from retinas of Myo7a-null mice, injected with AAV2-MYO7A(dual). n=3 animals;

FIG. 15A is the results of light microscopy of a semi-thin section from a treated Myo7a-null mouse retina. The region shown is near the injection site. Arrows indicate melanosomes in the apical processes. White lines indicate cells that still show the Myo7a-null phenotype, with an absence of melanosomes in the apical processes. Scale=50 µm. FIG. 15B is a low-magnification immunoEM image of RPE from a retina treated with AAV2-MYO7A(dual). As in FIG. 15A, the white line indicated a region that still showed the Myo7a-null phenotype. Rectangle 'c', includes melanosomes in the apical region, indicating a corrected RPE cell. Scale=500 nm. FIG. 15C, FIG. 15D, and FIG. 15E show higher-magnification images of regions outlined by the rectangles shown in FIG. 15B. MYO7A immunogold particles were indicated by circles. Scale=50 nm. FIG. 15F is a bar graph illustrating MYO7A immunogold particle density measured in RPE cells from Myo7a-null retinas, WT retinas, or from Myo7a-null retinas treated with AAV2-MYO7A (dual) and determined to be corrected or not corrected by the location of their apical melanosomes. n=3 animals per condition. Bars indicate SEM. FIG. 15G is an immunoEM image of a rod photoreceptor cilium double-labeled with antibodies against MYO7A (small gold particles) and against rod opsin (large gold particles). MYO7A labeling is associated with the connecting cilium and periciliary membrane, indicating expression and correct localization of MYO7A. While this region is devoid of opsin labeling, which is restricted to the disk membranes, it is consistent with the wild type (WT) phenotype, thus indicating correction of the mutant phenotype. Scale=300 nm;

FIG. 18A, FIG. 18B, FIG. 18C, and FIG. 18D show MYO7A expression in the connecting cilium and pericilium of rod photoreceptors from Myo7a-null retinas injected with diluted AAV2-MYO7A (FIG. 18a and FIG. 18B) or AAV5-MYO7A (FIG. 18C and FIG. 18D); (FIG. 18A and FIG. 18C) 1:10, (FIG. 18B and FIG. 18D) 1:100. Scale=200 nm;

FIG. 19 shows the structural preservation of injected Myo7a-null retinas. Light microscopy of the photoreceptor layer 3 weeks after injection with 10×AAV5-MYO7A. Scale=15 μm;

FIG. 20 shows structural preservation of injected Myo7a-null retinas. Light microscopy of photoreceptor layer 3 months after injection with 1×AAV2-MYO7A. Scale=10 μm;

FIG. 21A, FIG. 21B, FIG. 21C, and FIG. 21D show correction of abnormal levels of opsin in the connecting cilium and pericilium of rod photoreceptors following subretinal injections with AAV2-MYO7A or AAV5-MYO7A. ImmunoEMs from WT retina (FIG. 21A), Myo7a-null retinas treated with 1×AAV2-MYO7A (FIG. 21B) or 1×AAV5-MYO7A (FIG. 21C), and from an untreated Myo7a-null retina (FIG. 21D) labeled with anti-rod opsin and 12-nm gold-conjugated secondary antibody. Scale=200 nm;

FIG. 22A is a fragmented vector (fAAV). FIG. 22B shows simple overlap: the 1365-bp shared between the two vectors is shaded gray. FIG. 22C is a trans-splicing vector. FIG. 22D shows an AP hybrid vector: the 270-bp element shared between the two vectors is marked with diagonal gradient shading (⅓ head as described by Ghosh et al., 2011). FIG. 22 shows the native intron hybrid vectors utilizing the natural intron 23 of MYO7A sharing a 250-bp overlapping sequence. 3'MYO7A is the 3'-portion of MYO7A; 5'MYO7A is the 5'-portion of MYO7A; AAV is adeno-associated virus; AP is alkaline phosphatase; intron=intron 23 of MYO7A; pA=polyadenylation signal; SA=splice-acceptor site; SD=splice-donor site; smCBA=cytomegalovirus immediate early/chicken β-actin chimeric promoter;

FIG. 23A shows HEK293 cells infected with AAV2(tripleY-F) at MOIs of 10,000, 2000, and 400 FIG. 23B is a time-course assay of MYO7A expressed in HEK293 cells. Cells were harvested 3-7 days after infection. In FIG. 23C, HEK293 cells were infected with AAV2 dual vectors; MOI=multiplicity of infection; T=HEK293 cells transfected with full-length MYO7A plasmid; U=untreated HEK293 cells;

FIG. 26A, FIG. 26B, and FIG. 26C show the characterization of MYO7A dual-vectors' restoration of coding sequence. The experimental plan is shown in FIG. 26A. HEK293 cells were infected with AAV2-based dual-vector platforms, RNA was extracted, and gene-specific primers amplified the sequences using PCT. Control digests with BglII (B) and PpuMI (P) revealed the predicted banding pattern shown in FIG. 26B. Undigested (U) PCR product is shown as control and a DNA size marker for reference (M). Separately, products were digested with KpnI and AgeI, and then cloned into pUC57 for sequencing of the entire overlap region FIG. 26C. Ten clones per vector platform were analyzed. M13 forward- and reverse-primers specific for the subclone vector were used to obtain sense and antisense reads (each ~1000 bp) resulting in ~440 bp for which the sense and antisense reads overlapped. PCR=polymerase chain reaction

BRIEF DESCRIPTION OF THE SEQUENCES

Figure 1:
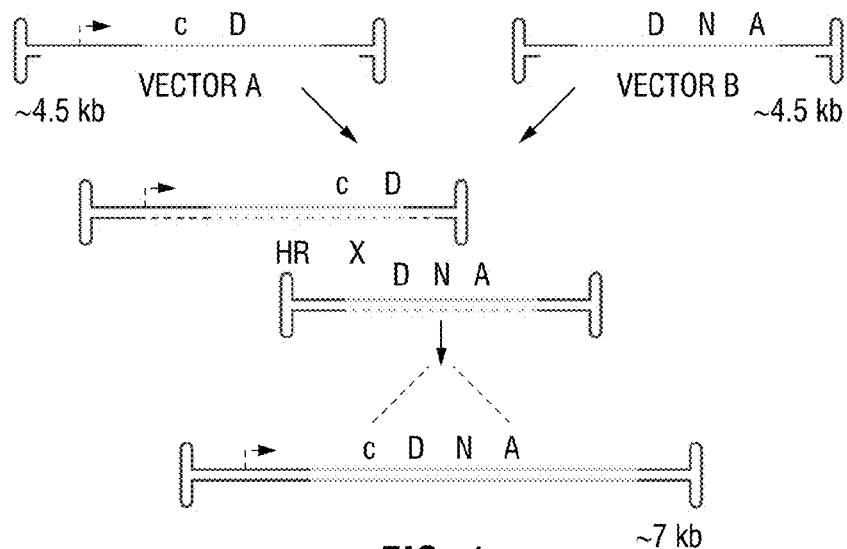
FIG. 1 shows the formation of complete gene cassette from dual AAV vectors via homologous recombination.

SEQ ID NO:1 is the nucleotide sequence of an "hMyo7a coding overlap vector A" of the subject invention;

SEQ ID NO:2 is the nucleotide sequence of an "hMyo7a coding overlap vector B" of the subject invention;

SEQ ID NO:3 is the nucleotide sequence of an "hMyo7a intron 23 splicing vector A" of the subject invention;

SEQ ID NO:4 is the nucleotide sequence of an "hMyo7a intron 23 splicing vector B" of the subject invention;

SEQ ID NO:5 is a nucleotide sequence encoding a human myosin VIIa polypeptide (protein coding sequence is nucleotides 273-6920);

SEQ ID NO:6 is the amino acid sequence of the human myosin VIIa polypeptide encoded by nucleotides 273-6920 of SEQ ID NO:5;

SEQ ID NO:7 is a nucleotide sequence that encodes a human myosin VIIa polypeptide;

SEQ ID NO:8 is an amino acid sequence of a human myosin VIIa polypeptide (isoform 2);

SEQ ID NO:9 is a synthetic oligonucleotide sequence, designated herein as P1, useful in accordance with one aspect of the present invention;

SEQ ID NO:10 is a synthetic oligonucleotide sequence, designated herein as P2, useful in accordance with one aspect of the present invention;

SEQ ID NO:11 is a synthetic oligonucleotide sequence, designated herein as P3, useful in accordance with one aspect of the present invention;

SEQ ID NO:12 is a synthetic oligonucleotide sequence, designated herein as P4, useful in accordance with one aspect of the present invention;

SEQ ID NO:13 is a synthetic oligonucleotide sequence, designated herein as P5, useful in accordance with one aspect of the present invention;

SEQ ID NO:14 is a synthetic oligonucleotide sequence, designated herein as P6, useful in accordance with one aspect of the present invention;

SEQ ID NO:15 is a synthetic oligonucleotide sequence, designated herein as P7, useful in accordance with one aspect of the present invention;

SEQ ID NO:16 is a synthetic oligonucleotide sequence, designated herein as P8, useful in accordance with one aspect of the present invention;

SEQ ID NO:17 is a synthetic oligonucleotide sequence, designated herein as P9, useful in accordance with one aspect of the present invention;

SEQ ID NO:18 is a synthetic oligonucleotide sequence, designated herein as P10, useful in accordance with one aspect of the present invention;

SEQ ID NO:19 is a synthetic oligonucleotide sequence, designated herein as P11, useful in accordance with one aspect of the present invention;

SEQ ID NO:20 is a synthetic oligonucleotide sequence, designated herein as P12, useful in accordance with one aspect of the present invention;

SEQ ID NO:21 is a synthetic oligonucleotide sequence, designated herein as P13, useful in accordance with one aspect of the present invention;

SEQ ID NO:22 is a synthetic oligonucleotide sequence, designated herein as P14, useful in accordance with one aspect of the present invention;

SEQ ID NO:23 is a synthetic oligonucleotide sequence, designated herein as P15, useful in accordance with one aspect of the present invention;

SEQ ID NO:24 is a synthetic oligonucleotide sequence, designated herein as P16, useful in accordance with one aspect of the present invention;

SEQ ID NO:25 is a synthetic oligonucleotide sequence, designated herein as P17, useful in accordance with one aspect of the present invention;

SEQ ID NO:26 is a synthetic oligonucleotide sequence, designated herein as P18, useful in accordance with one aspect of the present invention;

SEQ ID NO:27 is a synthetic oligonucleotide sequence, designated herein as P19, useful in accordance with one aspect of the present invention;

SEQ ID NO:28 is a synthetic oligonucleotide sequence, designated herein as P20, useful in accordance with one aspect of the present invention;

SEQ ID NO:29 is a synthetic oligonucleotide sequence, designated herein as P21, useful in accordance with one aspect of the present invention; and SEQ ID NO:30 is a synthetic oligonucleotide sequence, designated herein as P22, useful in accordance with one aspect of the present invention.

DESCRIPTION OF ILLUSTRATIVE EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would be a routine undertaking for those of ordinary skill in the art having the benefit of this disclosure.

The subject invention concerns materials and methods for genetic therapy of diseases and conditions, such as Usher syndrome 1B (USH1B). One aspect of the invention concerns AAV-based dual-vector systems that provide for expression of full-length proteins whose coding sequence exceeds the polynucleotide packaging capacity of individual AAV vector. In one embodiment, a vector system of the invention includes:

i) a first AAV vector polynucleotide comprising an inverted terminal repeat at each end (5' and 3' end) of the polynucleotide, and between the inverted terminal repeats a suitable promoter followed by (i.e., 3' to the promoter) a partial coding sequence that encodes an N-terminal part of a selected full-length polypeptide, and ii) a second AAV vector polynucleotide comprising an inverted terminal repeat at each end (i.e., the 5'- and 3'-ends) of the polynucleotide, and between the inverted terminal repeats a partial coding sequence that encodes a C-terminal portion of the selected full-length polypeptide, and optionally followed by a polyadenylation (pA) sequence. The coding sequences in the first and second vectors when combined encode the selected full-length polypeptide, or a functional fragment or variant thereof. The polypeptide encoding sequence in the first and second AAV vectors comprises sequence that overlaps.

In other words, a portion of the coding sequence present at the 3'-end of the coding sequence of the first vector is identical or substantially identical with a portion of the coding sequence present at the 5'-end of the coding sequence of the second vector. In one embodiment, the sequence overlap between the first and second AAV vectors is between about 500 and about 3000 nucleotides; between about 1000 and about 2000 nucleotides; between about 1200 and about 1800 nucleotides; or between about 1300 and about 1400 nucleotides.

In a specific embodiment, the sequence overlap is about 1350 nucleotides. In an exemplified embodiment, the sequence overlap is approximately 1365 nucleotides. In one embodiment, the polypeptide encoded is wild type or functional human myosin VIIa (hmyo7a). Amino acid sequences of wild type and functional hmyo7a polypeptides, and polynucleotides encoding them, are known in the art (see, for example, GenBank accession numbers NP_000251 and U39226.1). In one embodiment, an hmyo7a polypeptide comprises the amino acid sequence shown in SEQ ID NO:6 or SEQ ID NO:8, or a functional fragment or a variant thereof. In one embodiment, the hmyo7a polypeptide is encoded by the nucleotide sequence shown in SEQ ID NO:5 or SEQ ID NO:7. Other polypeptides contemplated include, but are not limited to, harmonin (Uniprot Q9Y6N9), cadherin 23 (Uniprot Q9H251), protocadherin 15 (Uniprot Q96QU1), and usherin (USH2A) (Uniprot O75445). In an exemplified embodiment, the first AAV vector polynucleotide comprises the nucleotide sequence of SEQ ID NO:1, or a functional fragment and/or variant thereof, and the second AAV vector polynucleotide comprises the nucleotide sequence of SEQ ID NO:2, or a functional fragment and/or variant thereof. In one embodiment, a construct or vector of the invention is administered by parenteral administration, such as intravenous, intramuscular, intraocular, intranasal, etc. In a specific embodiment, a construct or vector is administered by subretinal injection. The construct or vector can be administered in vivo or ex vivo.

In another embodiment, a vector system of the invention comprises i) a first AAV vector polynucleotide comprising an inverted terminal repeat at each end (i.e., the 5'-end and the 3'-end) of the polynucleotide, and between the inverted terminal repeats a suitable promoter followed by (i.e., 3' to the promoter) a partial coding sequence that encodes an N-terminal part of a selected full-length polypeptide followed by a splice donor site and an intron, and ii) a second AAV vector polynucleotide comprising an inverted terminal repeat at each end (5'-end and 3'-end) of the polynucleotide, and between the inverted terminal repeats an intron and a splice acceptor site for the intron, followed by a partial coding sequence that encodes a C-terminal part of the selected full-length polypeptide, optionally followed by a polyadenylation (pA) signal sequence.

The coding sequences in the first and second vectors when combined encode the selected full-length polypeptide, or a functional fragment or variant thereof. The intron sequence in the first and second AAV vectors comprises sequence that overlaps. In other words, all or part of the intron sequence present at the 3'-end of the coding sequence of the first vector is identical or substantially identical with all or part of the intron sequence present at the 5'-end of the coding sequence of the second vector. In one embodiment, intron sequence overlap between the first and second AAV vectors is several hundred nucleotides in length. In a specific embodiment, the intron sequence overlap is about 50 to about 500 nucleotides or so in length; alternatively between about 200 and about 300 nucleotides or so in length. In one embodiment, the intron sequence utilized in the vector system of the invention is a sequence of an intron naturally present in the genomic sequence of a gene encoding the selected polypeptide. In one embodiment, the intron is intron 23 of the hmyo7a gene. In a specific embodiment, the polypeptide encoded is hmyo7a and the intron is the full intron 23 of the hmyo7a gene. In an exemplified embodiment, the first AAV vector polynucleotide comprises the nucleotide sequence of SEQ ID NO:3, or a functional fragment and/or variant thereof, and the second AAV vector polynucleotide comprises the nucleotide sequence of SEQ ID NO:4, or a functional fragment and/or variant thereof. In another embodiment, the intron sequence utilized in the vector system of the invention is a sequence of an intron that is not naturally present in the genomic sequence of a gene encoding the selected polypeptide. In a specific embodiment, the intron is a synthetic alkaline phosphatase (AP) intron. The intron sequences utilized in the vector system of the present invention can comprise splice donor and splice acceptor sequences. In one embodiment, a construct or vector of the invention is administered by parenteral administration, such as intravenous, intramuscular, intraocular, intranasal, etc. In a specific embodiment, a construct or vector is administered by subretinal injection. The construct or vector can be administered in vivo or ex vivo.

The inverted terminal repeat (ITR) sequences used in an AAV vector system of the present invention can be any AAV ITR. The ITRs used in an AAV vector can be the same or different. In particular embodiments, the ITR may be obtained from an AAV serotype 2 (AAV2) or an AAV serotype 5 (AAV5). An AAV vector of the invention can comprise different AAV ITRs. For example, a vector may comprise an ITR of AAV2 and an ITR of AAV5. AAV ITR sequences are well known in the art (see, for example, GenBank Accession Nos. AF043303.1; NC_001401.2; J01901.1; JN898962.1; K01624.1; and K01625.1).

The AAV dual-vector systems disclosed herein are able to efficiently express a therapeutic gene that is larger than what may ordinarily be packaged within a single AAV vector.

The subject invention also concerns a virus or virion comprising a polynucleotide, expression construct, or vector construct of the invention. In one embodiment, the virus or virion is an AAV virus. Methods for preparing viruses and virions comprising a heterologous polynucleotide or construct are known in the art. In the case of AAV, cells can be co-infected or transfected with adenovirus or polynucleotide constructs comprising adenovirus genes suitable for AAV helper function. Examples of materials and methods are described, for example, in U.S. Pat. Nos. 8,137,962 and 6,967,018 (each of which is specifically incorporated herein, by express reference thereto).

An AAV virus or AAV vector of the invention can be of any AAV serotype, including, but not limited to, serotype AAV1, AAV2, AAV3, AAV4, AAV5, AAV6, AAV7, AAV8, AAV9, AAV10, AAV11, and AAV12. In exemplary embodiments, AAV2 and AAV5 serotype vectors have been utilized.

Figure 5:
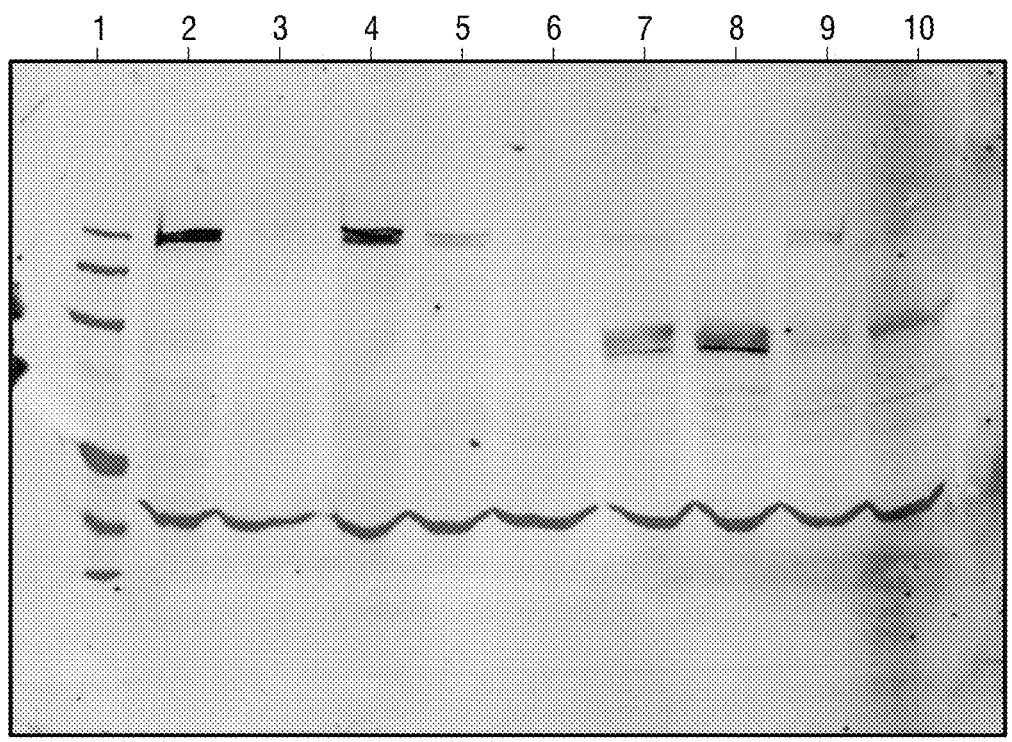
FIG. 5 shows an immunoblot to detect the presence of MYO7A in infected or transfected HEK293 cells. Heterogeneous vectors (described in introduction) are compared to all three dual-vector systems. Dual vectors were packaged either in AAV2 or in AAV2(triple mutant) capsids. The triple mutant contains three tyrosine-to-phenylalanine mutations on the capsid surface. For all three dual-vector systems, infections were performed with either a) the front-half (N-terminal) and back-half (C-terminal) vectors; or b) the front-half vectors alone (to confirm the presence or absence of a truncated protein product expressed from the promoter-containing N-terminal vectors)

In one embodiment, the AAV serotype provides for one or more tyrosine to phenylalanine (Y→F) mutations on the capsid surface. In a specific embodiment, the AAV is an AAV8 serotype having a tyrosine-to-phenylalanine (Tyr- →Phe) mutation at position 733 (Y733F). In FIG. 5, a triple-mutant vector is also contemplated. It contains tyrosine-to-phenylalanine (Tyr→Phe) mutations at positions Y733F, Y500F, and Y730F, respectively, corresponding to the amino acid sequence of the wild-type AAV8-capsid protein, or in one or more of the amino acids corresponding to those sequences in one or more related AAV capids, including, for example, AAV2, AAV5, and the like.

The subject invention also concerns methods for treating or ameliorating a disease or condition, such as an eye disease, in a human or animal using gene therapy and an AAV-based dual-vector system of the present invention. In one embodiment, a method of the invention comprises administering a vector system of the invention that encodes a polypeptide that provides for treatment or amelioration of the disease or condition. In one embodiment, the vectors of the invention are provided in an AAV virus or virion. The vector system can be administered in vivo or ex vivo. In one embodiment, a vector system of the invention is administered by parenteral administration, such as intravenous, intramuscular, intraocular, intranasal, etc. Administration can be by injection. In a specific embodiment, a vector system of the invention is administered to the human or animal by intraocular subretinal injection. In one embodiment, the disease or condition to be treated is Usher syndrome and the polypeptide provided is a mammalian myosin VIIa protein. In a specific embodiment, the myosin VIIa is a human myosin VIIa polypeptide. In one embodiment, an hmyo7a polypeptide comprises the amino acid sequence shown in SEQ ID NO:6 or SEQ ID NO:8, or a functional fragment or a variant thereof. In one embodiment, the hmyo7a polypeptide is encoded by the nucleotide sequence shown in SEQ ID NO:5 or SEQ ID NO:7.

Other polypeptides contemplated include, but are not limited to, harmonin (Uniprot Q9Y6N9), cadherin 23 (Uniprot Q9H251), protocadherin 15 (Uniprot Q96QU1), and usherin (USH2A) (Uniprot 075445). Dosage regimes and effective amounts to be administered can be determined by ordinarily skilled clinicians. Administration may be in the form of a single dose or multiple doses. General methods for performing gene therapy using polynucleotides, expression constructs, and vectors are known in the art (see, for example, *Gene Therapy: Principles and Applications* (1999); and U.S. Pat. Nos. 6,461,606; 6,204,251 and 6,106,826, each of which is specifically incorporated herein in its entirety by express reference thereto).

The subject invention also concerns methods for expressing a selected polypeptide in a cell. In one embodiment, the method comprises incorporating in the cell an AAV-based, dual-vector system as disclosed herein, wherein the vector system includes a polynucleotide sequence that encodes a selected polypeptide and of interest, and expressing the polynucleotide sequences in the cell. In certain embodiments, the selected polypeptide may be a polypeptide that is heterologous to the cell. In one embodiment, the cell is a mammalian cell, and preferably, a human cell. In one embodiment, the cell is human a photoreceptor cell, and preferably a human photoreceptor cone cell or a photoreceptor rod cell. In a specific embodiment, the cell expresses a wild type, functional, and/or biologically-active hmyo7a polypeptide that is encoded by a nucleic acid segment present in a vector system as disclosed herein. In one embodiment, the hmyo7a polypeptide is encoded by the nucleotide sequence shown in SEQ ID NO:5 or SEQ ID NO:7. Other polypeptides contemplated include, but are not limited to, harmonin (Uniprot Q9Y6N9), cadherin 23 (Uniprot Q9H251), protocadherin 15 (Uniprot Q96QU1), and usherin (USH2A) (Uniprot 075445). The cell can be one that is provided in vivo or in vitro.

The subject invention also concerns one or more mammalian cells that contain one of the AAV-based, dual-vector systems disclosed herein.

In one embodiment, the cell is a photoreceptor cell. In a specific embodiment, the cell is a cone cell; preferably, it is a human cone cell or a human rod cell. Such cells may express one or more nucleotide sequences provided in at least a first AAV-based, dual-vector system of the invention. In a specific embodiment, the cell expresses a wild type, functional, and/or biologically active hmyo7a polypeptide that is encoded by a nucleic acid segment comprised within one or more of the AAV-based vector systems as disclosed herein. In one embodiment, the hmyo7a polypeptide is encoded by the nucleotide sequence of SEQ ID NO:5 or SEQ ID NO:7. Other polypeptides contemplated include, but are not limited to, harmonin (Uniprot Q9Y6N9), cadherin 23 (Uniprot Q9H251), protocadherin 15 (Uniprot Q96QU1), and usherin (USH2A) (Uniprot 075445).

Vector systems of the invention can include regulatory elements that are functional in the intended host cell in which the vector is to be expressed. A person of ordinary skill in the art can select regulatory elements for use in appropriate host cells, for example, mammalian or human host cells. Regulatory elements include, for example, promoters, transcription termination sequences, translation termination sequences, enhancers, and polyadenylation elements.

A vector of the invention can comprise a promoter sequence operably linked to a nucleotide sequence encoding a desired polypeptide. Promoters contemplated for use in the subject invention include, but are not limited to, cytomegalovirus (CMV) promoter, SV40 promoter, Rous sarcoma virus (RSV) promoter, chimeric CMV/chicken β-actin promoter (CBA) and the truncated form of CBA (smCBA) (see, e.g., Haire et al. 2006 and U.S. Pat. No. 8,298,818, which is specifically incorporated herein in its entirety by express reference thereto). Additional photoreceptor-specific, human rhodopsin kinase (hGRK1) promoter, rod specific IRBP promoter, VMD2 (vitelliform macular dystrophy/Best disease) promoter, and EF1 alpha promoter sequences are also contemplated to be useful in the practice of various aspects of the present invention.

In a specific embodiment, the promoter is a chimeric CMV-β-actin promoter. In one embodiment, the promoter is a tissue-specific promoter that shows selective activity in one or a group of tissues but is less active or not active in other tissue. In one embodiment, the promoter is a photoreceptor-specific promoter. In a further embodiment, the promoter is preferably a cone cell-specific promoter or a rod cell-specific promoter, or any combination thereof. In one embodiment, the promoter is the promoter for human myosin 7a gene. In a further embodiment, the promoter comprises a cone transducin α (TaC) gene-derived promoter. In a specific embodiment, the promoter is a human GNAT2-derived promoter. Other promoters contemplated within the scope of the invention include, without limitation, a rhodopsin promoter, a cGMP-phosphodiesterase β-subunit promoter, a retinitis pigmentosa-specific promoter, an RPE cell-specific promoter [such as a vitelliform macular dystrophy-2 (VMD2) promoter (Best1) (Esumi et al., 2004)], or any combination thereof.

Promoters can be incorporated into a vector using standard techniques known to those of ordinary skill in the molecular biology and/or virology arts. Multiple copies of promoters, and/or multiple distinct promoters can be used in the vectors of the present invention. In one such embodiment, a promoter may be positioned about the same distance from the transcription start site as it is from the transcription start site in its natural genetic environment, although some variation in this distance is permitted, of course, without a substantial decrease in promoter activity. In the practice of the invention, one or more transcription start site(s) are typically included within the disclosed vectors.

The vectors of the present invention may further optionally include one or more transcription termination sequences, one or more translation termination sequences, one or more signal peptide sequences, one or more internal ribosome entry sites (IRES), and/or one or more enhancer elements, or any combination thereof. Transcription termination regions can typically be obtained from the 3' untranslated region of a eukaryotic or viral gene sequence. Transcription termination sequences can be positioned downstream of a coding sequence to provide for efficient termination. Signal peptide sequences are amino-terminal peptidic sequences that encode information responsible for the location of an operably-linked polypeptide to one or more post-translational cellular destinations, including, for example, specific organelle compartments, or to the sites of protein synthesis and/or activity, and even to the extracellular environment.

Enhancers—cis-acting regulatory elements that increase gene transcription—may also be included in one of the disclosed AAV-based vector systems. A variety of enhancer elements are known to those of ordinary skill in the relevant arts, and include, without limitation, a CaMV 35S enhancer element, a cytomegalovirus (CMV) early promoter enhancer element, an SV40 enhancer element, as well as combinations and/or derivatives thereof. One or more nucleic acid sequences that direct or regulate polyadenylation of the mRNA encoded by a structural gene of interest, may also be optionally included in one or more of the vectors of the present invention.

The disclosed dual-vector systems may be introduced into one or more selected mammalian cells using any one or more of the methods that are known to those of ordinary skill in the gene therapy and/or viral arts. Such methods include, without limitation, transfection, microinjection, electroporation, lipofection, cell fusion, and calcium phosphate precipitation, as well as biolistic methods. In one embodiment, the vectors of the invention may be introduced in vivo, including, for example, by lipofection (i.e., DNA transfection via liposomes prepared from one or more cationic lipids) (see, for example, Feigner et al., 1987). Synthetic cationic lipids (LIPOFECTIN, Invitrogen Corp., La Jolla, Calif., USA) may be used to prepare liposomes that will encapsulate the vectors to facilitate their introduction into one or more selected cells. A vector system of the invention can also be introduced in vivo as "naked" DNA using methods known to those of ordinary skill in the art.

Polynucleotides described herein can also be defined in terms of more particular identity and/or similarity ranges with those exemplified herein. The sequence identity will typically be greater than 60%, preferably greater than 75%, more preferably greater than 80%, even more preferably greater than 90%, and can be greater than 95%. The identity and/or similarity of a sequence can be 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% or greater as compared to a sequence exemplified herein.

Unless otherwise specified, as used herein percent sequence identity and/or similarity of two sequences can be determined using the algorithm of Karlin and Altschul (1990), modified as in Karlin and Altschul (1993). Such an algorithm is incorporated into the NBLAST and XBLAST programs of Altschul et al. (1990). BLAST searches can be performed with the NBLAST program, score=100, wordlength=12, to obtain sequences with the desired percent sequence identity. To obtain gapped alignments for comparison purposes, Gapped BLAST can be used as described (Altschul et al., 1997). When utilizing BLAST and Gapped BLAST programs, the default parameters of the respective programs (NBLAST and XBLAST) can be used in accordance with published methods.

The subject invention also contemplates those polynucleotide molecules having sequences that are sufficiently homologous with the polynucleotide sequences of the invention to permit hybridization with that sequence under standard stringent conditions and standard methods (Maniatis et al., 1982). As used herein, "stringent" conditions for hybridization refers to conditions wherein hybridization is typically carried out overnight at 20-25° C. below the melting temperature ($T_m$) of the DNA hybrid in 6×SSPE, 5×Denhardt's solution, and 0.1% SDS, containing 0.1 mg/mL of a suitable non-specific denatured DNA. Calculation of the melting temperature may be obtained using the standard formula of Beltz et al., (1983):

$$T_m = 81.5° C. + 16.6 \text{ Log } [Na^+] + 0.41(\% G+C) - 0.61(\% \text{ formamide}) - 600/\text{length of duplex in base pairs.}$$

Washes are typically carried out as follows:
(1) Twice at room temperature for 15 min in 1×SSPE, 0.1% SDS (i.e., a low-stringency wash); and
(2) Once at $T_m - 20°$ C. for 15 min in 0.2×SSPE, 0.1% SDS (i.e., a moderate-stringency wash).

As used herein, the terms "nucleic acid" and "polynucleotide sequence" refer to a deoxyribonucleotide or ribonucleotide polymer in either single- or double-stranded form, and unless otherwise limited, encompass known analogs of natural nucleotides that can function in a similar manner as naturally occurring nucleotides. The polynucleotide sequences include both full-length sequences, as well as shorter sequences derived from the full-length sequences. It is understood that a particular polynucleotide sequence includes the degenerate codons of the native sequence or sequences that may be introduced to provide codon preference in a specific host cell. The polynucleotide sequences falling within the scope of the subject invention further include sequences that specifically hybridize with the sequences coding for a peptide of the invention. The polynucleotide includes both the sense and antisense strands, either as individual strands or in the duplex.

Fragments and variants of a polynucleotide or polypeptide of the present invention can be generated as described herein and tested for the presence of function using standard techniques known in the art. Thus, an ordinarily skilled artisan can readily prepare and test fragments and variants of a polynucleotide or polypeptide of the invention and determine whether the fragment or variant retains functional activity that is the same or similar to a full-length or a non-variant polynucleotide or polypeptide, such as a myosin VIIa polynucleotide or polypeptide.

As those skilled in the art can readily appreciate, there can be a number of variant sequences of a protein found in nature, in addition to those variants that can be artificially created by the skilled artisan in the lab. The polynucleotides and polypeptides of the subject invention encompasses those specifically exemplified herein, as well as any natural variants thereof, as well as any variants which can be created artificially, so long as those variants retain the desired functional activity.

Also within the scope of the subject invention are polypeptides which have the same amino acid sequences of a polypeptide exemplified herein except for amino acid substitutions, additions, or deletions within the sequence of the polypeptide, as long as these variant polypeptides retain substantially the same relevant functional activity as the polypeptides specifically exemplified herein. For example, conservative amino acid substitutions within a polypeptide that do not affect the function of the polypeptide would be within the scope of the subject invention. Thus, the polypeptides disclosed herein should be understood to include variants and fragments, as discussed above, of the specifically exemplified sequences.

The subject invention further includes nucleotide sequences that encode the polypeptides disclosed herein. These nucleotide sequences can be readily constructed by those skilled in the art having the knowledge of the protein and amino acid sequences that are presented herein. As would be appreciated by one skilled in the art, the degeneracy of the genetic code enables the artisan to construct a variety of nucleotide sequences that encode a particular polypeptide or protein. The choice of a particular nucleotide sequence could depend, for example, upon the codon usage of a particular expression system or host cell.

Polypeptides having substitution of amino acids other than those specifically exemplified in the subject polypeptides are also contemplated within the scope of the present invention. For example, non-natural amino acids can be substituted for the amino acids of a polypeptide of the invention, so long as the polypeptide having substituted amino acids retains substantially the same activity as the polypeptide in which amino acids have not been substituted. Examples of non-natural amino acids include, but are not limited to, ornithine, citrulline, hydroxyproline, homoserine, phenylglycine, taurine, iodotyrosine, 2,4-diaminobutyric acid, α-amino isobutyric acid, 4-aminobutyric acid, 2-amino butyric acid, γ-amino butyric acid, ε-amino hexanoic acid, 6-amino hexanoic acid, 2-amino isobutyric acid, 3-amino propionic acid, norleucine, norvaline, sarcosine, homocitrulline, cysteic acid, τ-butylglycine, τ-butylalanine, phenylglycine, cyclohexylalanine, β-alanine, fluoro-amino acids, designer amino acids such as β-methyl amino acids, C-methyl amino acids, N-methyl amino acids, and amino acid analogs in general. Non-natural amino acids also include amino acids having derivatized side groups. Furthermore, any of the amino acids in the protein can be of the D- (dextrorotary) or the L- (levorotary) form.

Amino acids can be generally categorized in the following classes: non-polar, uncharged polar, basic, and acidic. Conservative substitutions whereby a polypeptide having an amino acid of one class is replaced with another amino acid of the same class fall within the scope of the subject invention so long as the polypeptide having the substitution retains substantially the same biological activity as a polypeptide that does not have the substitution. Table 1 provides a listing of examples of amino acids belonging to each class.

TABLE 1

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |

TABLE 1-continued

| Class of Amino Acid | Examples of Amino Acids |
| --- | --- |
| Acidic | Asp, Glu |
| Basic | Lys, Arg, His |

Also within the scope of the subject invention are polynucleotides that have the same, or substantially the same, nucleotide sequence of a polynucleotide exemplified herein, except for the presence of one or more nucleotide substitutions, additions, or deletions within the sequence of the polynucleotide, so long as these variant polynucleotides retain substantially the same relevant functional activity as the polynucleotides exemplified herein (i.e., they encode a protein having the same amino acid sequence or the same functional activity as one of the polynucleotides specifically exemplified herein). Thus, the polynucleotides disclosed herein should also be understood to include variants and fragments thereof.

The methods of the present invention can be used with humans and other animals. The other animals contemplated within the scope of the invention include domesticated, agricultural, or zoo- or circus-maintained animals. Domesticated animals include, for example, dogs, cats, rabbits, ferrets, guinea pigs, hamsters, pigs, monkeys or other primates, and gerbils. Agricultural animals include, for example, horses, mules, donkeys, burros, cattle, cows, pigs, sheep, and alligators. Zoo- or circus-maintained animals include, for example, lions, tigers, bears, camels, giraffes, hippopotamuses, and rhinoceroses. As used herein, the terms "patient" and "subject" are used interchangeably and are intended to include such human and non-human species. Likewise, in vitro methods of the present invention may also be performed on cells of one or more human or non-human, mammalian species.

As one of ordinary skill in the molecular biological arts can readily appreciate, there can be a number of variant sequences of a gene or polynucleotide found in nature, in addition to those variants that may be artificially prepared or synthesized by an ordinary-skilled artisan in a laboratory environment. The polynucleotides of the subject invention encompasses those specifically exemplified herein, as well as any natural variants thereof, as well as any variants which can be created artificially, so long as those variants retain the desired biological activity.

Also within the scope of the subject invention are polynucleotides which have the same nucleotide sequences of a polynucleotide exemplified herein except for nucleotide substitutions, additions, or deletions within the sequence of the polynucleotide, as long as these variant polynucleotides retain substantially the same relevant biological activity as the polynucleotides specifically exemplified herein. Thus, the polynucleotides disclosed herein should be understood to include variants and fragments, as discussed above, of the specifically exemplified sequences.

Pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

The present invention also concerns pharmaceutical compositions comprising a vector system of the invention in combination with a pharmaceutically acceptable carrier. Pharmaceutical compositions adapted for topical or parenteral administration, comprising an amount of a compound constitute a preferred embodiment of the invention. The dose administered to a patient, particularly a human, in the context of the present invention should be sufficient to achieve a therapeutic response in the patient over a reasonable timeframe, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

The subject invention also concerns kits comprising a vector system of the invention in one or more containers. Kits of the invention can optionally include pharmaceutically acceptable carriers and/or diluents. In one embodiment, a kit of the invention includes one or more other components, adjuncts, or adjuvants as described herein. In one embodiment, a kit of the invention includes instructions or packaging materials that describe how to administer a vector system contained within the kit to a selected mammalian recipient. Containers of the kit can be of any suitable material, e.g., glass, plastic, metal, etc., and of any suitable size, shape, or configuration. In one embodiment, a vector system of the invention is provided in the kit as a solid. In another embodiment, a vector system of the invention is provided in the kit as a liquid or solution. In certain embodiments, the kits may include one or more ampoules or syringes that contain a vector system of the invention in a suitable liquid or solution form.

Multiple distinct AAV-based, dual-vector systems have been created and disclosed herein for use in gene-replacement therapies, including, for example, in the treatment of USH1B in human patients. In a specific embodiment, a vector system of the present invention employs two discrete AAV vectors that each packages a maximal-size DNA molecule (i.e., ~4.5 to 4.8 Kb). The two vectors are co-administered to selected recipient cells to reconstitute the full-length, biologically-active, Myo7a polypeptide. In these constructs, a portion of overlapping nucleic acid sequence is common to each of the vector genomes (see FIG. 1). When co-delivered to suitable cells, the overlapping sequence region facilitates the proper concatamerization of the two partial gene cassettes. These gene cassettes then undergo homologous recombination to produce a full-length gene cassette within the cells (see FIG. 1). Shared components of exemplified embodiments of the dual-vector systems include the use of AAV inverted terminal repeats (TR), the small version of the chimeric CMV/chicken β-actin promoter (smCBA), human Myo7a (hMyo7a) cDNA sequence and the SV40 polyadenylation (pA) signal.

Exemplary Definitions

In accordance with the present invention, polynucleotides, nucleic acid segments, nucleic acid sequences, and the like, include, but are not limited to, DNAs (including, but not limited to, genomic and/or extragenomic DNAs), genes, peptide nucleic acids (PNAs) RNAs (including, but not limited to, rRNAs, mRNAs, and/or tRNAs), nucleosides, as well as one or more nucleic acid segments obtained from natural sources, chemically synthesized, genetically modified, or otherwise prepared or synthesized in whole or in part by the hand of man.

Unless defined otherwise, all technical and scientific terms used herein have the same meaning as commonly understood by one of ordinary skill in the art to which this invention belongs. Although any methods and compositions similar or equivalent to those described herein can be used in the practice or testing of the present invention, the preferred methods and compositions are described herein. For purposes of the present invention, the following terms are defined below:

The term "effective amount," as used herein, refers to an amount that is capable of treating or ameliorating a disease or condition or otherwise capable of producing an intended therapeutic effect.

The term "operably linked," as used herein, refers to that the nucleic acid sequences being linked are typically contiguous, or substantially contiguous, and, where necessary to join two protein coding regions, contiguous and in reading frame. However, since enhancers generally function when separated from the promoter by several kilobases and intronic sequences may be of variable lengths, some polynucleotide elements may be operably linked but not contiguous.

The term "promoter," as used herein, refers to a region or regions of a nucleic acid sequence that regulates transcription.

The term "regulatory element," as used herein, refers to a region or regions of a nucleic acid sequence that regulates transcription. Exemplary regulatory elements include, but are not limited to, enhancers, post-transcriptional elements, transcriptional control sequences, and such like.

The term "substantially corresponds to," "substantially homologous," or "substantial identity," as used herein, denote a characteristic of a nucleic acid or an amino acid sequence, wherein a selected nucleic acid or amino acid sequence has at least about 70 or about 75 percent sequence identity as compared to a selected reference nucleic acid or amino acid sequence. More typically, the selected sequence and the reference sequence will have at least about 76, 77, 78, 79, 80, 81, 82, 83, 84 or even 85 percent sequence identity, and more preferably, at least about 86, 87, 88, 89, 90, 91, 92, 93, 94, or 95 percent sequence identity. More preferably still, highly homologous sequences often share greater than at least about 96, 97, 98, or 99 percent sequence identity between the selected sequence and the reference sequence to which it was compared.

The percentage of sequence identity may be calculated over the entire length of the sequences to be compared, or may be calculated by excluding small deletions or additions which total less than about 25 percent or so of the chosen reference sequence. The reference sequence may be a subset of a larger sequence, such as a portion of a gene or flanking sequence, or a repetitive portion of a chromosome. However, in the case of sequence homology of two or more polynucleotide sequences, the reference sequence will typically comprise at least about 18-25 nucleotides, more typically at least about 26 to 35 nucleotides, and even more typically at least about 40, 50, 60, 70, 80, 90, or even 100 or so nucleotides.

When highly-homologous fragments are desired, the extent of percent identity between the two sequences will be at least about 80%, preferably at least about 85%, and more preferably about 90% or 95% or higher, as readily determined by one or more of the sequence comparison algorithms well-known to those of ordinary skill in the art, such as e.g., the FASTA program analysis described by Pearson and Lipman (1988).

The term "subject," as used herein, describes an organism, including mammals such as primates, to which treatment with the compositions according to the present invention can be provided. Mammalian species that can benefit from the disclosed methods of treatment include, but are not limited to, humans, non-human primates such as apes; chimpanzees; monkeys, and orangutans, domesticated animals, including dogs and cats, as well as livestock such as horses, cattle, pigs, sheep, and goats, or other mammalian species including, without limitation, mice, rats, guinea pigs, rabbits, hamsters, and the like.

The term "treatment" or any grammatical variation thereof (e.g., treat, treating, and treatment etc.), as used herein, includes but is not limited to, alleviating a symptom of a disease or condition; and/or reducing, suppressing, inhibiting, lessening, ameliorating or affecting the progression, severity, and/or scope of a disease or condition.

The term "vector," as used herein, refers to a nucleic acid molecule (typically one containing DNA) that is capable of replication in a suitable host cell, or one to which another nucleic acid segment can be operatively linked so as to facilitate replication of the operably-nucleic acid segment. Exemplary vectors include, without limitation, plasmids, cosmids, viruses and the like.

All patents, patent applications, provisional applications, and publications referred to or cited herein are incorporated by reference in their entirety, including all figures and tables, to the extent they are not inconsistent with the explicit teachings of this specification.

EXAMPLES

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Dual-AAV Vector System 1: hMyo7a Coding Overlap

Figure 2:
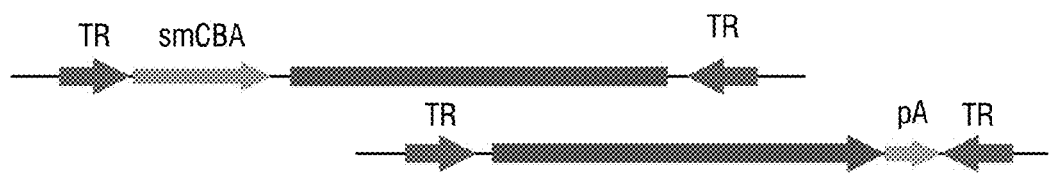
FIG. 2 shows a schematic of the two vector components that make up Dual-Vector System 1 in accordance with one aspect of the present invention.

In the case of Dual-Vector System 1 (FIG. 2) the overlapping DNA sequence shared by both vector A and vector B consists of a 1350-bp coding region for the human Myo7a gene. This is the simplest system of the present invention, and appears to be highly efficient in terms of full-length gene reconstitution, and MYO7A expression. Advantageously, each vector is of standard AAV packaging size, and as such, each packages DNA with a high degree of efficiency, and is readily adaptable to conventional GMP standards. Such vectors are also readily characterized to permit requisite regulatory approval prior to use in humans.

Example 2—Dual-AAV Vector System 2: hMyo7a Intron 23 Splicing

Figure 3:
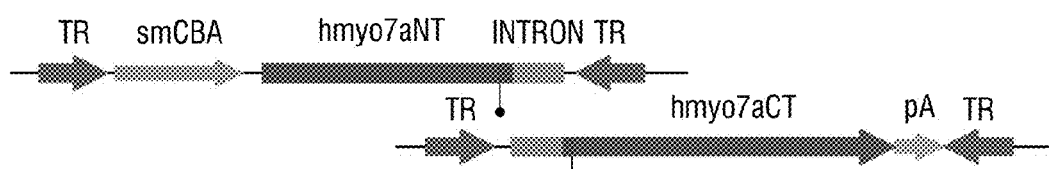
FIG. 3 shows a schematic of the two vector components that make up Dual-Vector System 2 in accordance with one aspect of the present invention. Native hMyo7a intron 23 in shown in light green; splice donor and splice acceptor sequence are shown in dark green.
Figure 4:
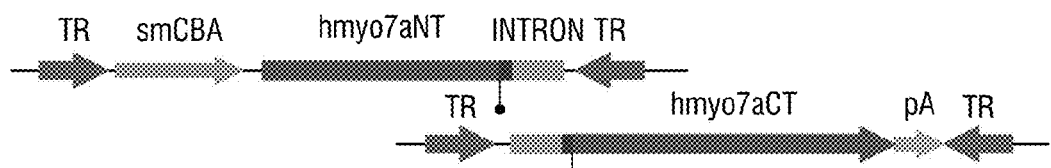
FIG. 4 shows the schematic of the two vector components that make up Dual-Vector System 3 in accordance with one aspect of the present invention. This is an exemplary standard transplicing dual vector pairs with the "intron" in this case referring to the alkaline phosphatase splice donor and acceptor sites. Synthetic alkaline phosphatase (AP) intron is shown in light blue; AP splice donor and splice acceptor sequences are shown in dark blue.

In the case of Dual-Vector System 2 (FIG. 3) the overlapping DNA sequence is composed of the native intron 23 of human Myo7a. Vector A contains the coding sequence corresponding to the amino-terminal portion of the hMyo7a cDNA relative to intron 23 (hMyo7aNT) and the native splice-donor site, followed by the entire intron 23 of hMyo7a (minus the native acceptor site). Vector B contains the carboxy-terminal portion of the hMyo7a cDNA relative to intron 23 (hMyo7aCT), and the full intron 23 of Myo7a (minus the native splice-donor site), followed by the native splice-acceptor site. Upon co-delivery to suitable mammalian host cells, the DNA of vectors A and B recombine to form a reconstituted full-length gene cassette. The resulting RNA transcript will then 'splice out' the native intron. Alternatively, recombination and formation of the gene cassette can occur via the AAV TRs. In this case, the RNA transcript will 'splice out' the native intron23-TR-intron23 motif. In both cases, however, the resulting mRNA is that of the reconstituted full-length hMyo7a gene sequence.

Example 3—In Vitro Performance of System 1: hMyo7a Coding Overlap

Figure 6A:
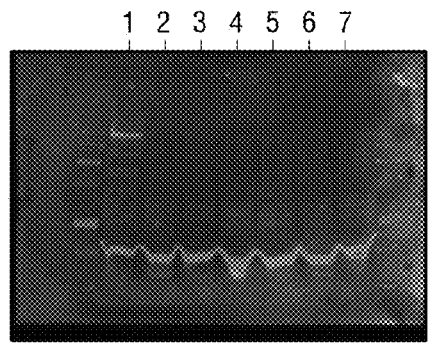
FIG. 6A and FIG. 6B show immunoblot to detect the presence of myo7A in HEK293 cells infected with Dual-Vector System 1. Results are presented as a time course from 3-7 days post infection (lanes 3-7) and are compared to cells transfected with myo7a plasmid (lane 1) and uninfected control (lane 2). The area inside the white box shown in FIG. 6A is magnified and presented at higher contrast in FIG. 6B. Starting at 3-days' post-infection, full-length human MYO7a protein was visible, with peak expression occurring around day 5.
Figure 6B:

HEK293 cells were infected simultaneously with vector A and vector B of Dual-Vector System 1 (FIG. 2) at a ratio of 10000:1 vg/cell for each vector. The AAV vectors were then packaged in AAV2 virions that contain three Y→F mutations in the capsid protein (see, for example, Zhong et al., 2008). As a positive control, cells were transfected with plasmid containing full-length hMyo7a under the control of smCBA. Protein was recovered from cells at 3-, 4-, 5-, 6- and 7-days' post-infection, and an antibody directed against MYO7A was used to assay for its presence in the infected cells via immunoblotting. The results are shown in FIG. 6A and FIG. 6B. The area inside the white box is magnified, and presented at higher contrast on the right. Starting at 3-days' post-infection, the full-length human MYO7a protein was visible; peak expression of the protein occurred around Day 5.

Example 4—In Vivo Performance of System 1: hMyo7a Coding Overlap

Figure 7A:
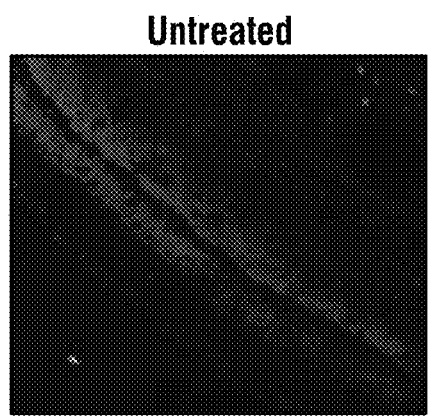
FIG. 7A and FIG. 7B show retinas from untreated mice and mice treated subretinally with Dual-Vector System 1. Immunohistochemistry (IHC) was performed using an antibody directed against MYO7A. The 'green' is the stain of MYO7A and 'blue' corresponds to nuclear, DAPI stain.
Figure 7B:
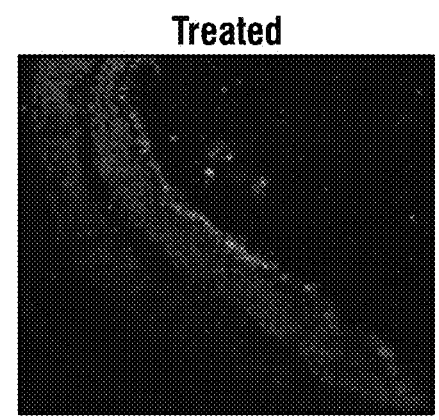
Figure 8A:
FIG. 8A, FIG. 8B, FIG. 8C, and FIG. 8D show differences in RPE melanosome localization in wild type vs. shaker-1 mice. In wild type mice, RPE melanosome apically migrate towards photoreceptor outer segments (FIG. 8A) whereas this phenomenon fails to occur in mice lacking Myo7a (shaker-1), as seen in (FIG. 8B). To the right is a high magnification image of single RPE cells from either a wild type (FIG. 8C) or shaker-1 (FIG. 8D) mouse showing this phenomenon up close.
Figure 8B:
Figure 8C:
Figure 8D:
Figure 9A:
FIG. 9A, FIG. 9B, and FIG. 9C show apical migration of RPE melanosomes is restored in shaker-1 mice injected with Dual-Vector System 1. Electron microscopy reveals that melanosomes of untreated shaker-1 mice do not apically migrate (FIG. 9A). In shaker-1 mice injected with Dual-Vector System 1 (packaged in AAV2), RPE melanosomes migrate apically towards photoreceptors, which can be seen here in both low- and high-magnification images (FIG. 9B and FIG. 9C)
Figure 9B:
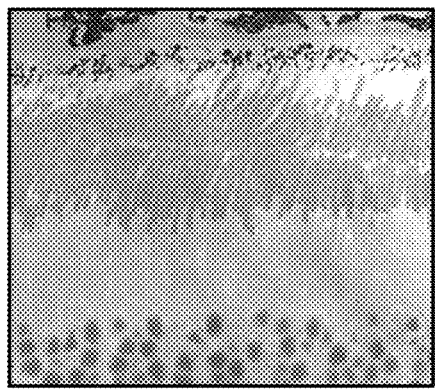
Figure 9C:

Six week old shaker-1 (Myo7a null) mice were sub-retinally co-injected with 1 µL of the same preparations of vector A and vector B of Dual-Vector System 1 used in the above in vitro study. Both vectors contained ~1×10$^{12}$ vg/mL. Four weeks' post-injection, retinas from treated and untreated eyes were collected and immunohistochemistry (IHC) was performed using an antibody directed against MYO7A (see FIG. 7A and FIG. 7B). The area in green showed MYO7A-specific staining, while the areas in blue corresponded to the nuclear-specific, DAPI stain. In the treated eye, MYO7A expression was clearly visible, and it appeared to be restricted to photoreceptors—more precisely to the juncture of the photoreceptor inner and outer segments.

Example 5—AAV Dual Vectors Efficiently Deliver Oversized Genes

Animals.

Shaker-1 mice carrying the 4626SB allele, an effective null mutation (Liu et al., 1999; Hasson et al., 1997), were used on the C57BL6 genetic background, and maintained and genotyped as described (Liu et al., 1999; Gibbs et al., 2003a). They were maintained on a 12-hr light/12-hr dark cycle, with exposure to 10-50 lux of fluorescent lighting during the light phase, and were treated according to federal and institutional animal care guidelines. Homozygous mutants were distinguished from the heterozygous controls by their hyperactivity, head-tossing and circling behavior (Gibson et al., 1995), and/or by a PCR/restriction digest assay.

Construction of AAV Vectors.

Single-vector platform: AAV vector plasmid, containing the truncated chimeric CMV/chicken β-actin promoter (smCBA) (Haire et al., 2006) and MYO7A cDNA was constructed by removing the full MYO7A cDNA from pEGFP-C2 by EagI and SalI digest, and then ligating into pTR-smCBA-GFP that had been digested with NotI and SalI to remove GFP. The MYO7A cDNA (~6.7 kb) corresponded to isoform 2 of human MYO7A, and was the same as that described previously by Hashimoto et al. (2007), which was based on the sequence published by Chen et al. (1996) (see, SEQ ID NO:8). MYO7A isoform 2 is 114-kb shorter than isoform 1 (Chen et al., 1996; Weil et al., 1996). Both the MYO7A cDNA, and the resulting junctions were fully sequenced prior to packaging. All vectors intended for in vitro analyses were separately packaged in wild type AAV2, or alternatively in the AAV2(tripleY→F) capsid mutant vector (Petrs-Silva et al., 2011). As noted above, AAV2-based vectors were chosen for the in vitro experiments due to their increased transduction efficiency relative to other serotypes (Ryals et al., 2011). All vectors were packaged, purified, and titered using standard methods as previously described (Zolotukhin et al., 2002; Jacobson et al., 2006). Human embryonic kidney (HEK293) cells were transfected by the calcium phosphate method with vector plasmid carrying the full-length MYO7A coding sequence of variant 2 (the plasmid used to package fAAV). These transfected cells were then used as a positive control throughout immunoblot analyses to indicate the appropriate size of full-length MYO7A protein. Vector infections were carried out in HEK293 cells with titer-matched AAV vectors. In brief, cells were grown to 60-70% confluency. All vectors were diluted in a balanced salt solution to achieve the desired multiplicity of infection (MOI). If not specifically mentioned, cells were infected at 10,000 genome-containing particles/cell of each vector, resulting in an MOI of 20,000 total for each vector pair. Cells were incubated in medium containing 10% serum for 3 days post-infection at 37° C. under 7% $CO_2$, and then analyzed via immunoblot. Titers of $10^{12}$ to $10^{13}$ particles/mL were obtained for different lots of AAV2-MYO7A and AAV5-MYO7A.

Oligonucleotide Sequences.

For in vivo studies, a human influenza hemagglutinin (HA) tag was added to the 3' termini of the full-length, simple overlap, trans-splicing, and *hybrid* 3' vectors by utilizing a unique BamHI site (P19), and replacing the non-tagged 3'-end with an HA-tagged (P20) version. All constructs were sequence verified by Sanger sequencing.

AAV Vector Plasmid Design and Cloning.

Figure 22A:
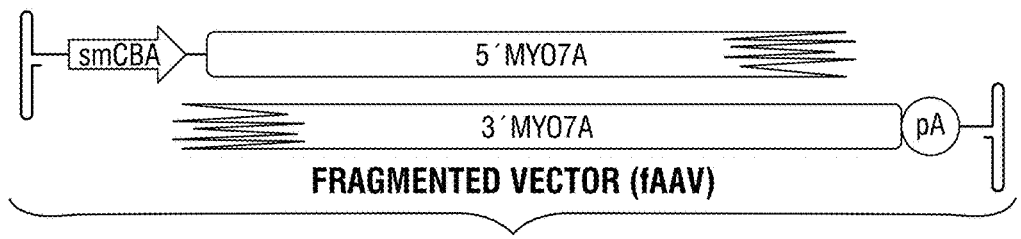
FIG. 22A, FIG. 22B, FIG. 22C, FIG. 22D, and FIG. 22E show a schematic representation of the dual-AAV-vector pairs created for this study.
Figure 22B:
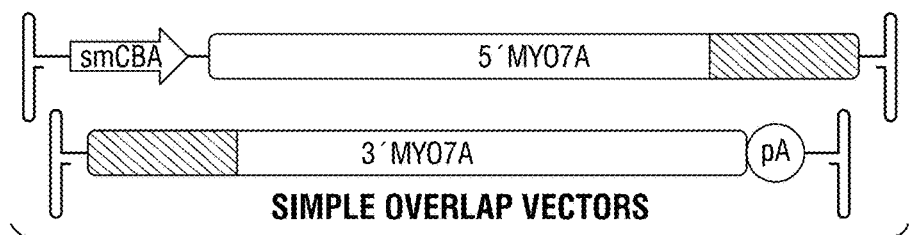
Figure 22C:
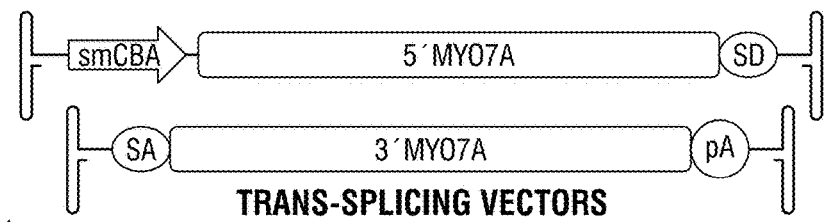
Figure 22D:
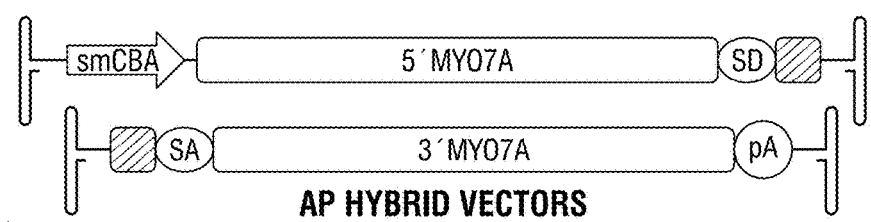
Figure 22E:
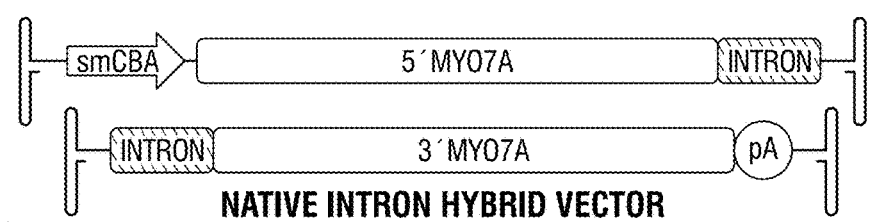

The full-length coding sequence of MYO7A (human isoform 2; GenBank Accession No. NM_001127180) was cloned into a vector plasmid containing the strong, ubiquitous CMV/chicken β-actin (smCBA) promoter (Haire et al., 2006), a polyadenylation signal, and the AAV2 ITRs. Packaging of this plasmid generated the fAAV vector (FIG. 22A). In all systems, the 5' vectors shared the smCBA promoter and a 5' portion of MYO7A, whereas the 3' vectors contained a 3'-portion of MYO7A, and a bovine growth hormone (bGH) polyadenylation signal. Oligonucleotides used for vector construction are listed in Table 2. The simple overlap contained nucleotides 1 through 3644 of MYO7A cDNA from the ATG in the 5' vector, and nucleotides 2279 through 6534 in the 3' vector. The fragments were amplified with oligonucleotides P1 and P3 by polymerase chain reaction (PCR) and cloned into the 5' vector via NotI and NheI, and the 3' vector with P3 (AflII) and P4 (KpnI), respectively. The resulting two vector plasmids share 1365 bp of overlapping MYO7A sequence (FIG. 22B). The trans-splicing and hybrid vectors utilize splice junctions composed of either ideal splice donor and acceptor sites derived from AP coding sequence or native MYO7A splice junctions from exons 23 and 24 (Yan et al., 2002). To create the 5' trans-splicing vector, the splice-acceptor site was amplified using oligonucleotides P5 and P6 (NheI), and the amplicon was then used in a second reaction with oligonucleotide P7 (NsiI) to add a part of the MYO7A coding sequence for cloning. The corresponding 3' vector was similarly created by amplifying the splice-acceptor site with oligonucleotides P8 (AflII) and P9 in a first PCR, and adding part of the 3' MYO7A coding sequence with oligonucleotide P10 (AgeI) in a second PCR (see FIG. 22C). The AP hybrid vectors were created by adding 270 bp of AP overlap sequence to the respective trans-splicing vectors (Ghosh et al., 2011). The sequence was amplified by PCR and, in so doing, appropriate restriction endonuclease sites were added. For the 5' vector oligonucleotides P11 (NheI) and P12 (SalI) were used, while oligonucleotides P13 (NotI) and P14 (AflII) were used for the 3' vector (FIG. 22D). A fourth vector pair, "native intron hybrid" vector, was also created to exploit the natural sequence in and around intron 23 of MYO7A as a recombination locus, and subsequent splicing signal. The 5'-portion was created by amplifying intron 23 with oligonucleotides P15 and P16 (NheI) first, and then using the resulting amplicon in a second reaction with oligonucleotide P7 (NsiI) to facilitate cloning. The corresponding 3'-vector was constructed by amplifying the intron 23 with oligonucleotides P17 and P18 (AflII), and the resulting amplicon, with oligonucleotide P10 (AgeI) in a second reaction (see FIG. 22E).

TABLE 2

OLIGONUCLEOTIDES USED IN THIS STUDY

| | Oligo 5'-3' sequence (restriction sites underlined) | Restriction site | (SEQ ID NO:) |
|---|---|---|---|
| P1 | GCG<u>GCGGCCGC</u>CACCATGGTGATTCTTCAGCAGGGGAC | NotI | (SEQ ID NO: 9) |
| P2 | GCG<u>GCTAGC</u>GAAGTTCCGCAGGTACTTGAC | NheI | (SEQ ID NO: 10) |
| P3 | GCG<u>CTTAAG</u>CAGGTCTAACTTTCTGAAGCTG | AflII | (SEQ ID NO: 11) |

TABLE 2-continued

OLIGONUCLEOTIDES USED IN THIS STUDY

| Oligo | 5'-3' sequence (restriction sites underlined) | Restriction site | (SEQ ID NO:) |
|---|---|---|---|
| P4 | GCGGGTACCTCACTTGCCGCTCCTGGAGCC | KpnI | (SEQ ID NO: 12) |
| P5 | GGCACCTAGTGGCTTTGAGGTAAGTATCAAGGTTACAAGAC | | (SEQ ID NO: 13) |
| P6 | GCGGCTAGCTCAGAAACGCAAGAGTCTTC | NheI | (SEQ ID NO: 14) |
| P7 | CTTCTTTGTGCGATGCATCAAG | NsiI | (SEQ ID NO: 15) |
| P8 | GCGCTTAAGCGACGCATGCTCGCGATAG | AflII | (SEQ ID NO: 16) |
| P9 | CGCCCTCGCTCCAGGTCCTGTGGAGAGAAAGGCAAAG | | (SEQ ID NO: 17) |
| P10 | GAACCCGAACCGGTCCTTG | AgeI | (SEQ ID NO: 18) |
| P11 | GCGGCTAGCCCCCGGGTGCGCGGCG | NheI | (SEQ ID NO: 19) |
| P12 | GCGGTCGACGAAACGGTCCAGGCTATGTG | SalI | (SEQ ID NO: 20) |
| P13 | GCGGCGGCCGCCCCCGGGTGCGCGGCG | NotI | (SEQ ID NO: 21) |
| P14 | GCGCTTAAGGAAACGGTCCAGGCTATGTG | AflII | (SEQ ID NO: 22) |
| P15 | CAGGCACCTAGTGGCTTTGAGGTACCAGGCTAGGGACAGG | | (SEQ ID NO: 23) |
| P16 | GCGGCTAGCCGCCTGAGCCCAGAAGTTC | NheI | (SEQ ID NO: 24) |
| P17 | CGCCCTCGCTCCAGGTCCTGAAGGAGACAAGAGGTATG | | (SEQ ID NO: 25) |
| P18 | GCGCTTAAGCACCGCTTGTGTTGATCCTC | AflII | (SEQ ID NO: 26) |
| P19 | GCCAGGGAAGGATCCCATG | BamHI | (SEQ ID NO: 27) |
| P20 | GCGGGTACCTCATGCGTAATCCGGTACATCGTAAGGGTACTTGCCGCTCCTGGAGCC | KpnI | (SEQ ID NO: 28) |
| P21 | AGCTTCGTAGAGTTTGTGGAGCGG | | (SEQ ID NO: 29) |
| P22 | GAGGGGCAAACAACAGATG | | (SEQ ID NO: 30) |

Oligonucleotides were used to make 5' and 3' vectors of the dual-vector platforms (P1-P20). Oligonucleotides were used to characterize the fidelity of the overlap in simple overlap, trans-splicing and AP hybrid vector platforms (P21-P22). Restriction sites used for cloning are underlined and the introduced HA tag is noted in italics (P19).

Dual-Vector Platform.

Two separate vector plasmids were constructed: Vector A contains the strong, ubiquitous "smCBA" promoter and MYO7A cDNA encoding the N-terminal portion. Vector B contains MYO7A cDNA encoding the C-terminal portion and a poly-A signal sequence. Each vector plasmid contained both inverted terminal repeats (ITRs). Using PCR with full-length MYO7A cDNA as a template, the MYO7A cDNA was divided roughly in half with amplicons encompassing nucleotide positions 1 through 3644 (Vector A) and 2279 through 6647 (Vector B) relative to ATG start position 1. The resulting two-vector plasmids shared 1365 bp of overlapping MYO7A sequence, and were 5.0- and 4.9-Kb in length, respectively. This was well within the size limitation of standard AAV vectors. Both vector plasmids were sequence verified and separately packaged by standard AAV production methods (Zolotukhin et al., 2002; Jacobson et al., 2006). The titer of the first lot contained $2.5 \times 10^{12}$ particles/mL of each vector, and the second lot contained $4 \times 10^{12}$ particles/mL of each vector.

Reverse Transcription and Characterization of Overlap Region.

HEK293 cells were infected with dual vectors, and total RNA was extracted with the RNeasy® kit (Qiagen, Hilden, Germany) according to the manufacturer's recommended protocol. Two micrograms of RNA was then subjected to DNaseI (NEB) digestion for 30 min at 37° C., followed by heat inactivation at 75° C. for 10 min Reverse transcription to cDNA was achieved with the SuperscriptIII® kit (Life Technologies, Grand Island, N.Y., USA) according to the standard protocol utilizing the oligo dT primer. Two microliters of cDNA was used as template in a PCR (95° C. for 3 min initial denature, 35 cycles of 95° C. for 45 sec, 55° C. for 45 sec, 72° C. for 12 min, and a final 72° C. for 15 min) using oligonucleotide primers P21 and P22 (see Table 2). Annealing sites for these primers are located 5' and 3', respectively, of the area of cDNA overlap (in other words, outside the region of overlap) in the simple overlap and hybrid vector pairs. The 3'-primer annealed to sequence that was complimentary to the bGH polyA. Resulting products were digested with either PpuMI or BglII, separated on a 1.5% agarose gel, and subsequently analyzed on a UV screen. Separately, products were digested with KpnI and AgeI, and subsequently cloned into a pUC vector for sequencing of the entire overlap region. M13 forward and reverse primers that were specific for the vector were used to obtain sense and antisense reads resulting in an ~140 bp overlap of the sense and antisense reads. To demonstrate that these methods were capable of detecting aberrant sequence (i.e., quality control), a MYO7A sequence was generated using either an artificial insertion (HindIII fill-in at position 2635) or a point mutation (T→C) at position 2381, and the analyses were repeated.

Viral Delivery In Vitro.

HEK293A cells (Invitrogen), grown in DMEM with 10% FBS and 1×NEAA and Pen/Strep (Invitrogen) were plated in 6 well-plates. The next day cells were incubated, at 37° C. and 5% $CO_2$, with AAV2- and AAV5-MYO7A at an MOI of 10,000 viral particles/cell in 500 µL of complete medium, containing also 40 µM of calpain inhibitor (Roche, Pleasanton, Calif., USA). Two hours later complete medium was added. The next day, the medium was changed and cells were incubated for an additional 48 hrs. Alternatively, some cells were transfected with 1 µg of vector pTR-smCBA-MYO7A, complexed with Lipofectamine 2000 (ratio 1:3), according to the manufacturer's instructions (Invitrogen).

Primary mouse RPE cells were derived from P14-P16 Myo7a-null animals and cultured in 24-well dishes, as described (Gibbs et al., 2003a; Gibbs and Williams, 2003b). After 48 hrs in culture, cells were transduced with viruses. Cells were incubated in 100 µL of complete medium containing 40 µM of calpain inhibitor, and 10,000 viral particles/cell from full-strength AAV stocks. After 2 hrs, 400 µL of complete medium was added to each well, and incubated overnight. The medium was changed the following day, and cells were incubated for an additional 48 hrs.

ARPE19 cells (American Type Culture Collection, Manassas, Va., USA) were cultivated in DMEM/F-12 with 10% FBS and split into 24-well plates with glass coverslips. Cells were grown to confluency and then transduced in the same manner, as were the primary RPE cells.

MYO7A Expression Analysis by Western Blot and Immunofluorescence.

HEK293A and primary mouse RPE cells that were transduced with AAV-MYO7A were collected 3 days post-transduction. For western blot analyses, cells were collected and lysed in 20 mM TRIS, pH 7.4, 5 mM $MgCl_2$, 10 mM NaCl, 1 mM DTT and 1× protease inhibitor cocktail (Sigma-Aldrich Chemical Co., St. Louis, Mo., USA). Equivalent amounts of total protein were separated on a 7.5% SDS-PAGE gel. After transfer, blots were blocked with 5% non-fat milk, and probed with mouse anti-MYO7A antibody, generated against residues 927-1203 of human MYO7A (Developmental Studies Hybridoma Bank, Iowa City, Iowa USA) (Soni et al., 2005), and mouse anti-actin antibody (Sigma-Aldrich) as a loading control.

Immunofluorescence was performed with ARPE19 and mouse RPE primary cells, 3 days after infection. Cells were fixed in 4% formaldehyde, blocked with blocking solution (0.5% BSA/0.05% saponin in PBS), incubated with the mouse anti-MYO7A followed by goat anti-mouse Alexa-568 (Molecular Probes, Carlsbad, Calif., USA). Coverslips were mounted with mounting medium containing DAPI (Fluorogel II, Electron Microscopy Sciences, Hatfield, Pa., USA) and visualized on a Leica confocal system.

Protein Extraction and Immunoblotting.

Transfected and infected HEK293 cells were harvested and washed twice in PBS and processed as previously reported with minor modifications (Boye et al., 2012). The cells were lysed by 3×30 sec pulses of sonication in 200 µL of sucrose buffer (0.23 M sucrose, 2 mM EDTA, 5 mM Tris-HCl, pH 7.5) containing protease inhibitors (Roche, Mannheim, Germany). Unlysed cells and cell debris were removed by centrifugation at 14,000 rpm for 10 min. The protein concentration of the supernatant was measured with BCA (Thermo Fisher Scientific, Rockland, Ill., USA). Equal amounts of protein were then loaded on 7.5% sodium dodecyl sulfate polyacrylamide gel electrophoresis gels (BioRad, Hercules, Calif., USA) and transferred in CAPS buffer (pH 11) onto PVDF membranes (Millipore, Billerica, Mass.). Blots were then labeled with antibodies against MYO7A (monoclonal antibody raised against amino acids 11-70 of human MYO7A; Santa Cruz, Dallas, Tex., USA; 1:1000) or HA (MMS-101P; Covance, Gaithersburg, Md., USA; 1:500) and β-actin (ab 34731; Abcam, Cambridge, Mass., USA; 1:5000). For visualization with the Odyssey system (Li-Cor, Lincoln, Nebr., USA), an antimouse and an anti-rabbit secondary antibody conjugated with CW800 and IR680 dyes (Li-Cor), respectively, were used. Semiquatitative densitometric measurements were performed with Odyssey acquisition and analysis software (Li-Cor). The dual-color images were separated in their respective channels and converted to gray scale for presentation purposes. Size markers present in one channel of each blot were added to both channels for visualization of protein sizes.

Viral Delivery In Vivo.

Mice were anesthetized with 2.0-3.0% isoflurane inhalation. The pupils of the animals were dilated with 1% (wt./vol.) atropine sulfate and 2.5% phenylephrine. A local anesthetic (0.5% proparacaine hydrochloride) was also administered. A sclerotomy in the temporal limbus was performed with a 27-Ga needle. A 32-Ga blunt needle, attached to a microsyringe pump (WPI, Sarasota Fla., USA) was inserted and 1 µL of viral solution was injected into the ventral subretinal space of P14-P16 animals. Retinal detachment was visualized under a dissecting microscope, and registered as indication of a positive subretinal injection. One microliter of the following AAV8(Y733F)-based vectors was injected subretinally in one eye of C57BL/6 mice: single fAAV ($1\times10^{13}$ vg/mL), front and back half "hybrid" vectors combined equally (each vector=$1\times10^{13}$ vg/mL), or front and back half "simple overlap" vectors combined equally (each vector=$1\times10^{13}$ vg/mL). Subretinal injections were performed as previously described (Timmers et al., 2001). Further analysis was carried out only on animals that received comparable, successful injections (>60% retinal detachment with minimal surgical complications).

Light Microscopy and Immunoelectron Microscopy of Retinas.

Eyecups were processed for embedment in either LR White or Epon, and semithin and ultrathin sections were prepared. Semithin sections were stained with toluidine blue and visualized on a Leica confocal system. Ultrathin sections were labeled with purified MYO7A pAb 2.2 (Liu et al., 1997) and monoclonal anti-opsin (1D4, R. Molday), followed by gold-conjugated secondary antibodies (Electron Microscopy Sciences), as described previously (Lopes et al., 2011). Negative control sections processed at the same time included those from Myo7a-null retinas, and, as positive control, WT animals were used.

MYO7A immunogold density was determined on sections of age-matched WT, Myo7a-null retinas and retinas of Myo7a-null animals that had been injected with AAV-MYO7A at P14-16 and dissected three weeks later. For quantification of the immunolabel, all of the gold particles in a complete section of each RPE cell were counted. The area of each cell's profile was determined using ImageJ software. For background labeling, the concentration of label in sections of untreated Myo7a-null animals was measured. Data were expressed with this background labeling subtracted.

The concentration of MYO7A and opsin immunogold labeling in the connecting cilia of photoreceptor cells was determined by counting gold particles along longitudinal profiles of connecting cilia and measuring the length of each profile.

Analysis and quantifications were performed in a minimum of three different retinas, from three different animals. Statistical analysis was performed using one-tail Student's t-test.

Six weeks postinjection, C57BL/6 mice were enucleated and their eyes processed and immunostained as previously described (Boye et al., 2011) with minor modifications. Retinas were immunostained with an antibody specific for HA (monoclonal Ab clone 12CA5; Roche), counterstained with DAPI, and imaged with a spinning disk confocal microscope (Nikon Eclipse TE2000 microscope equipped with Perkin Elmer Ultraview Modular Laser System and Hamamatsu O-RCA-R2 camera). Images were obtained sequentially using a 20×(air) objective lens. All settings (exposure, gain, laser power) were identical across images. All image analysis was performed using Volocity 5.5 software (Perkin Elmer, Waltham, Mass., USA).

Results

AAV-MYO7A Single Vector Preparations.

Figure 10A:
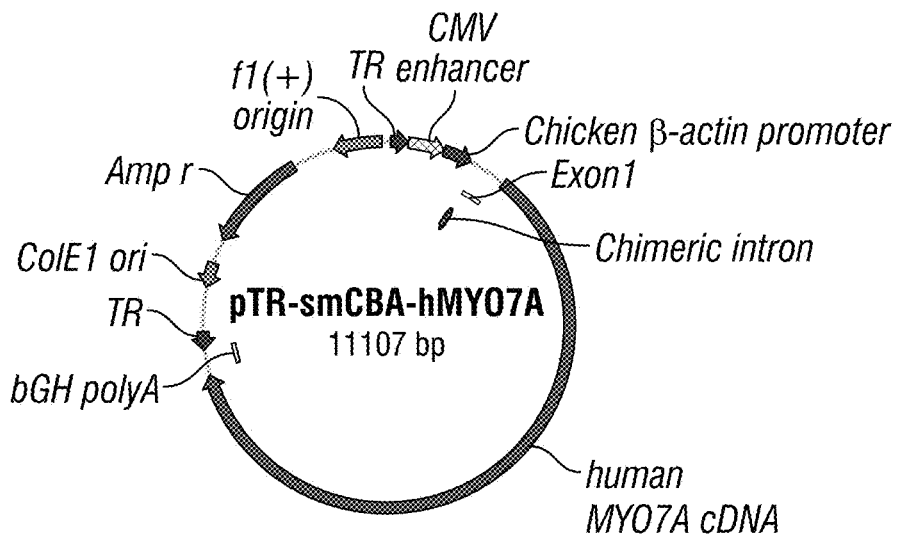
FIG. 10A, FIG. 10B, FIG. 10C, FIG. 10D, FIG. 10E, and FIG. 10F illustrate the expression of MYO7A from single AAV2 and AAV5 vectors in cultured cells.

AAV vector plasmid was engineered to contain a truncated chimeric CMV/chicken β-actin promoter, smCBA (Haire et al., 2006) and the 6.7-kb cDNA encoding the full-length isoform 2 of human MYO7A (NCBI # NM_001127180) (FIG. 10A). The smCBA promoter exhibits the same tropism and activity in mouse retinas as that of the full-length CBA promoter (Haire et al., 2006; Pang et al., 2008). Titers of $10^{12}$ to $10^{13}$ particles/mL were obtained for different lots of AAV2-MYO7A and AAV5-MYO7A. A concentration of $10^{12}$ particles/mL was regarded as the standard concentration (1×), from which dilutions were made. The experiments were performed with virus obtained from three separate preparations. No differences in expression or phenotype correction, as described below, were observed among the different lots for AAV2-MYO7A or AAV5-MYO7A at a given concentration.

MYO7A Expression in Cell Culture.

Figure 10B:
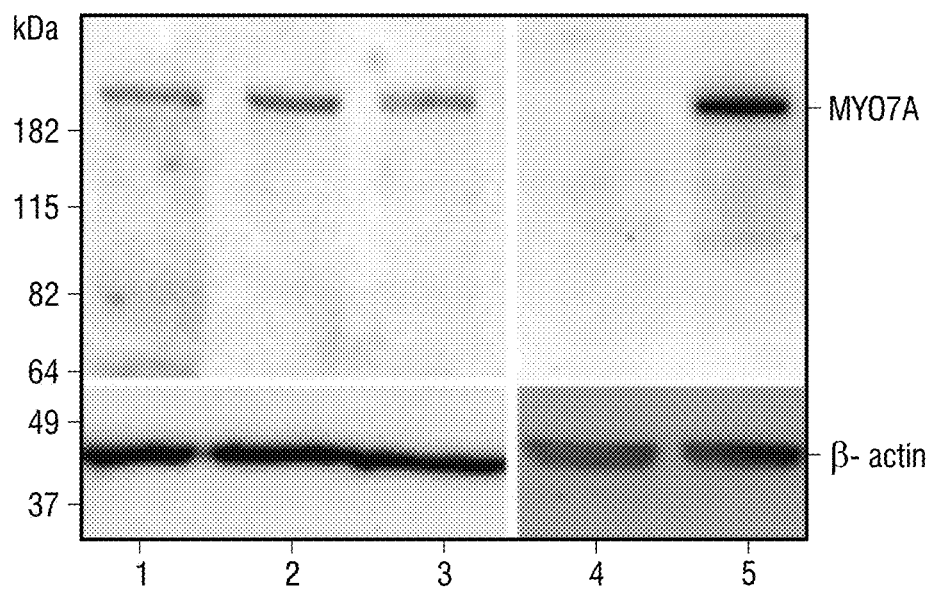
Figure 10C:
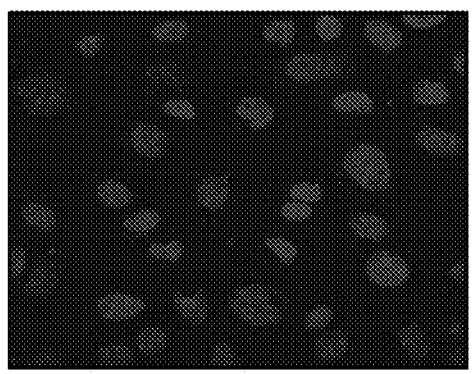
Figure 10D:
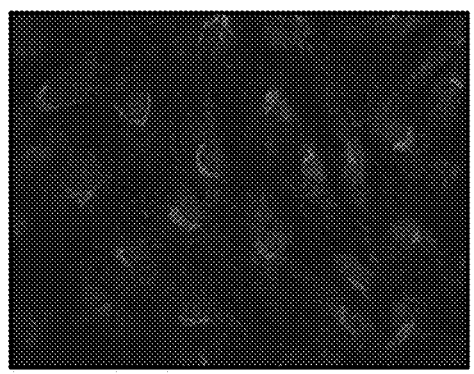
Figure 10E:
Figure 10F:
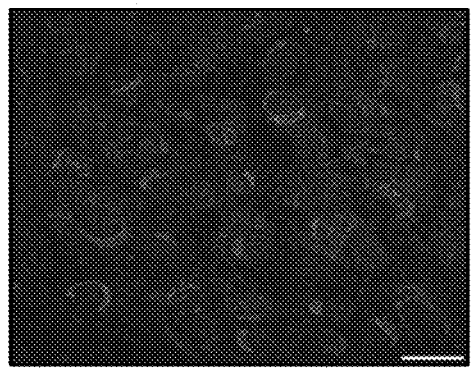

Transduction of primary cultures of Myo7a-null RPE cells with 1× single AAV2-MYO7A or AAV5-MYO7A resulted in the expression of a polypeptide that, by western blot analysis, had an apparent mass that was comparable to that of WT MYO7A protein, and was present at similar levels to that found in primary cultures of Myo7a$^{+/-}$ RPE cells (FIG. 10B). Likewise, a single band of appropriate size was detected on western blots of HEK293A cells. Immunofluorescence of the primary RPE cells showed that the MYO7A protein, resulting from 1× single AAV-MYO7A treatment of MYO7A-null cells, had a subcellular localization pattern that was comparable to that of endogenous MYO7A in control cells, indicating the generation of appropriately targeted protein (FIG. 10C, FIG. 10D, FIG. 10E, and FIG. 10F). ARPE19 cells were also infected with 1× or diluted (1:100) AAV2-MYO7A or AAV5-MYO7A, and compared with non-treated cells. An increase in MYO7A immunofluorescence was detected in the treated cells, and the intracellular localization of the label was comparable to that in untreated cells (FIG. 17A, FIG. 17B, FIG. 17C, FIG. 17D, FIG. 17E, and FIG. 17F).

Localization of MYO7A In Vivo.

Most retinal MYO7A is found in the RPE (Hasson et al., 1995), however, the protein is also present in the connecting cilium and pericilium of the photoreceptor cells (Liu et al., 1997; Williams, 2008). A diagram illustrating this distribution and the retinal functions of MYO7A has been published in a recent review (Williams and Lopes, 2011).

Three weeks following injection of 1×AAV-MYO7A or AAV5-MYO7A into the subretinal space of Myo7a-null mice, retinal tissue was examined by immunoelectron microscopy to test for MYO7A expression Immunogold label was evident in the photoreceptor cells, where it was localized in the connecting cilium and pericilium, comparable to that in WT retinas (FIG. 11A, FIG. 11B, FIG. 11C, FIG. 11D, and FIG. 11E). Label was also present throughout the RPE cells, particularly in the apical cell body region (FIG. 11F, FIG. 11F-1, FIG. 11G, and FIG. 11G-1; see FIG. 18A, FIG. 18B, FIG. 18C, and FIG. 18D for controls), as found in WT retinas (Gibbs et al., 2004; Liu et al., 1997).

Figure 11I:
Figure 11H:
Figure 11G:
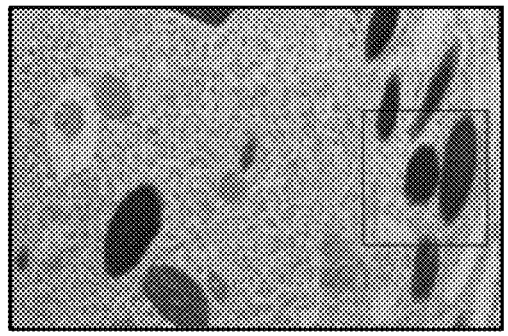
Figures 1, 11G:
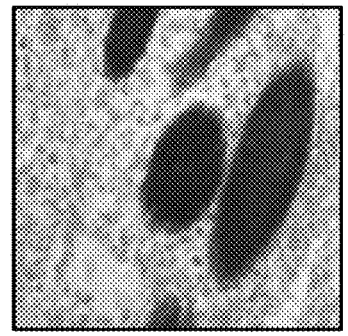
Figure 11F:
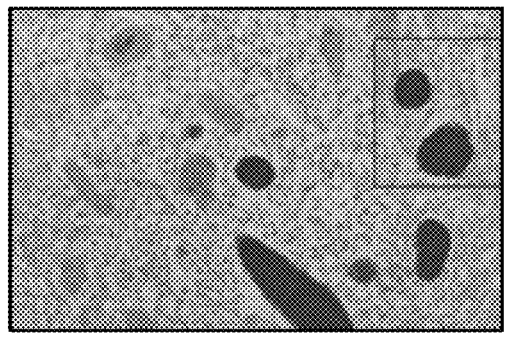
Figures 1, 11F:
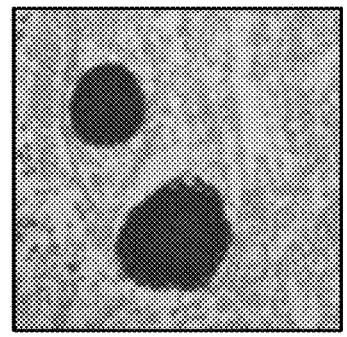

MYO7A has a similar distribution in both rod and cone photoreceptor cells (Liu et al., 1999). To test whether treatment with AAV-MYO7A also affected cone photoreceptor cells, it was determined whether MYO7A was also present in the ciliary region of cone photoreceptors. Double immunoEM of treated retinas was performed, using a MYO7A antibody together with an antibody specific for rod opsin. Although there are only a small number of cones with aligned connecting cilia found in each ultrathin section, MYO7A immunogold label was evident in the connecting cilium and periciliary region of these cones, which were identified by lack of rod opsin labeling in their outer segments (in contrast to the surrounding rod outer segments) (FIG. 11H and FIG. 11I). Hence, AAV2-MYO7A and AAV5-MYO7A can transduce cone as well as rod photoreceptor cells.

Dose-Dependent MYO7A Expression in Photoreceptor and RPE Cells.

To determine the levels of MYO7A expression following treatment with different concentrations of AAV2-MYO7A and AAV5-MYO7A (1×, 1:10 or 1:100 dilutions), MYO7A immunogold labeling was quantified in EM images, taken within 1.4 mm of the injection site. Reliable detection of MYO7A in the photoreceptor cells, where its distribution is limited to the connecting cilium and pericilium, requires the higher resolution provided by electron microscopy (Liu et al., 1997). Immunogold particle density was measured in images of the photoreceptor connecting cilium and pericilium, shown in complete longitudinal section (from the basal bodies to the base of the outer segment), and in images showing the RPE cells in apical to basal section. Particle density was expressed as particles per length of cilium for the photoreceptor cells (each connecting cilium is ~1.2 μm long), and as particles per area for the RPE cells (the entire area between the apical and basal surfaces was included). Particle density is dependent on exposure of epitopes on the surface of the section, and, as such, provides a relative linear measure of antigen density under the conditions used here (i.e., grids were etched and labeled in an identical manner, and the labeling was not so dense as to be affected by steric hindrance).

Figure 11J:
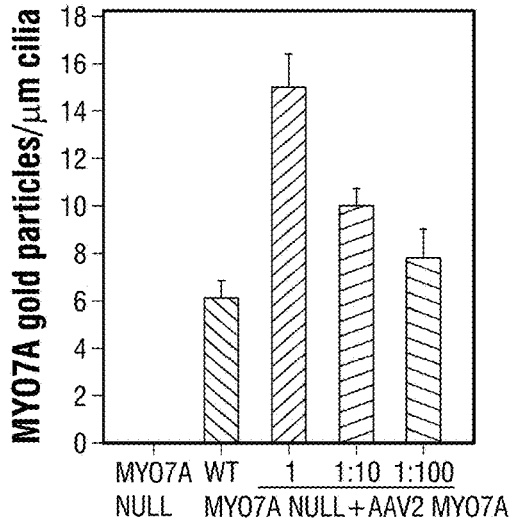
Figure 11K:
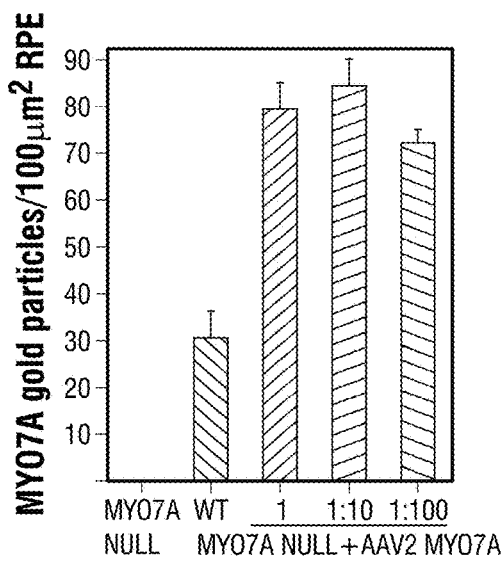
Figure 11L:
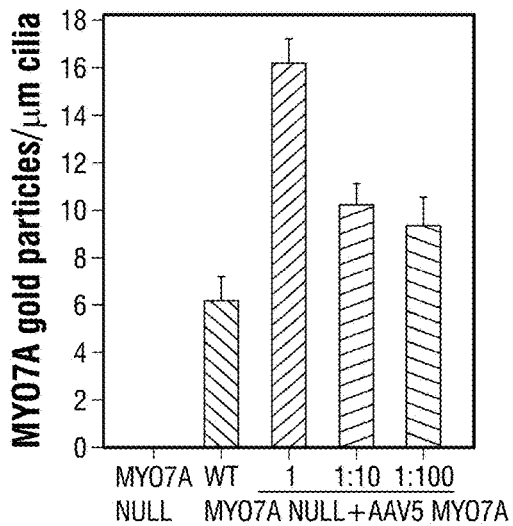
Figure 11M:
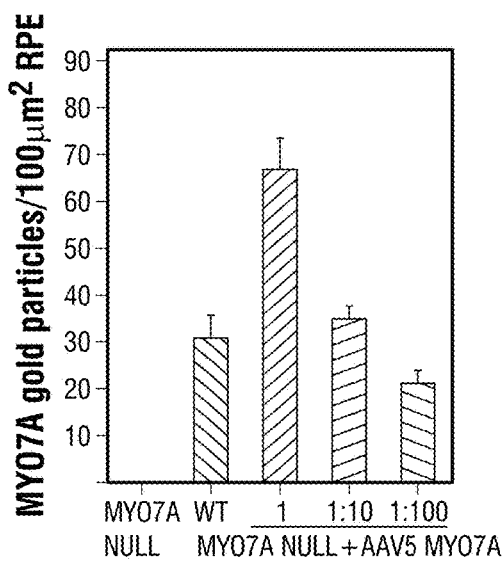

Treatment with 1×AAV2-MYO7A or AAV5-MYO7A resulted in 2.5-2.7 times the density of immunolabel in the photoreceptor cilium, compared with that found in WT retinas, while the 1:10 and 1:100 dilutions resulted in a density of immunolabel that was more comparable to WT levels (FIG. 11J, FIG. 11L, and FIG. 19). Quantification of immunogold label in the RPE showed that injection of AAV2-MYO7A resulted in 2.7 times more label than in WT, with the 1:10 and 1:100 dilutions showing no significant difference (FIG. 11K). In contrast, the level of MYO7A immunolabel in the RPE of retinas injected with AAV5-MYO7A varied in relation to virus titer, with the full dose virus effecting 2.2-fold more MYO7A than that found in WT RPE, the 1:10 dilution effecting WT levels, and the 1:100 dilution resulting, on average, ~60% of WT levels (FIG. 11M).

These counts of labeling density indicate that 1×AAV-MYO7A resulted in more than double the normal level of MYO7A expression in both the photoreceptor and RPE cells. The distribution of MYO7A was not affected by this overexpression in the photoreceptor cells. In the RPE cells, the overall distribution of MYO7A was comparable to WT, with a higher concentration in the apical cell body region. However, with 1×AAV2-MYO7A or 1×AAV5-MYO7A, the proportion of MYO7A that was associated with melanosomes was only 55% of that in WT RPE: This difference is possibly because the proteins that link MYO7A to the melanosomes, MYRIP and RAB27A (Klomp et al., 2007; Lopes et al., 2007), may have remained near WT levels, and thus limited the absolute amount of MYO7A that could associate with the melanosomes.

Despite the overexpression of MYO7A, no pathology was evident in retinas, up to 3 months after injection of 1× (or 1:10) AAV2-MYO7A. However, two out of six retinas injected with $10^{13}$ particles/mL of AAV5-MYO7A (i.e., 10×) showed evidence of photoreceptor cell loss across the retina after 3 weeks (AAV2-MYO7A was not tested at this titer) (FIG. 19).

Correction of Melanosome Localization in the RPE.

Figure 12A:
FIG. 12A, FIG. 12B, FIG. 12C, FIG. 12D, FIG. 12E, and FIG. 12F show correction of melanosome localization, following subretinal injections with AAV2-MYO7A or AAV5-MYO7A. Light micrographs showing the presence of melanosomes in the apical processes of the RPE in a WT retina (FIG. 12A) and retinas injected with AAV2-MYO7A (FIG. 12B) or AAV5-MYO7A (FIG. 12C). Further away from the injection site (FIG. 12D), melanosomes are present in the apical processes of some RPE cells, but not in others (arrows indicate apical melanosomes; white lines indicate regions where melanosomes are absent from the apical processes).
Figure 12B:
Figure 12C:
Figure 12D:
Figure 12E:
Figure 12F:
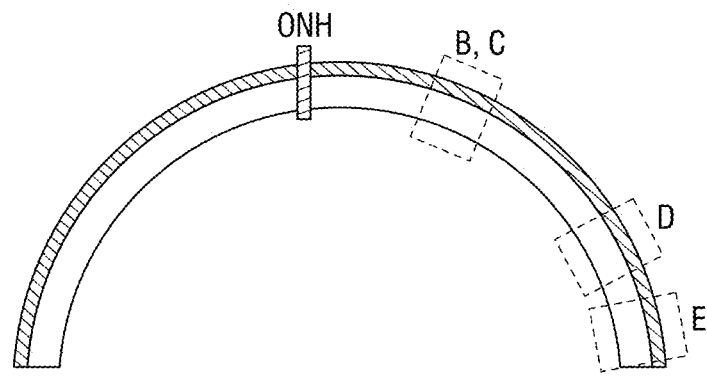

In Myo7a-mutant mice, melanosomes are absent from the apical processes of the RPE cells (Liu et al., 1998). This mutant phenotype is evident at all neonatal ages, and is due to loss of actin-based transport of the melanosomes by the myosin 7a motor (Gibbs et al., 2004). Three weeks following injection of 1×AAV2-MYO7A or AAV5-MYO7A into the subretinal space of Myo7a-null mice, melanosomes were observed to have a normal distribution in all RPE cells near the site of injection (within 1.4 mm) (n=10 each for AAV2-MYO7A and AAV5-MYO7A) (FIG. 12A, FIG. 12B, and FIG. 12C). Well away from the injection site, a mixture of corrected and uncorrected RPE cells was evident, while, at the periphery of the retina, the cells all exhibited the Myo7a-mutant phenotype, indicating lack of correction in this region (FIG. 12D, FIG. 12E, and FIG. 12F). The correction of melanosomes was still evident in retinas that were fixed 3 months after injection (FIG. 20). Correction was also observed in all eyes injected with 1:10 dilution AAV2-MYO7A (n=6) or AAV5-MYO7A (n=6), as well as in all eyes injected with 1:100 dilution AAV2-MYO7A (n=6) or AAV5-MYO7A (n=6), although with the 1:100 dilution some of the RPE cells near the site of injection were not corrected.

Correction of Opsin Distribution.

Figure 13:
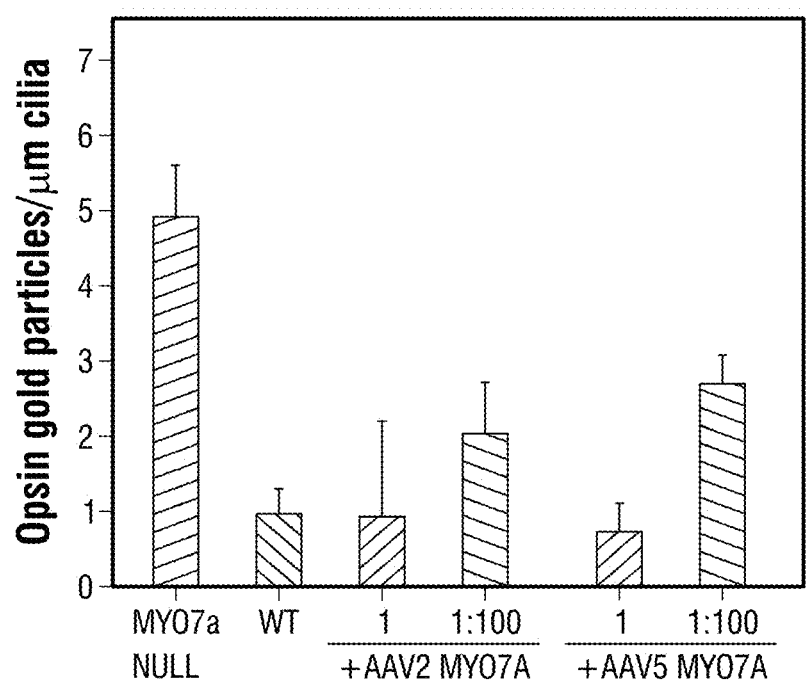
FIG. 13 shows the correction of abnormal levels of opsin in the connecting cilium and pericilium of rod photoreceptors, following subretinal injections with AAV2-MYO7A or AAV5-MYO7A. The bar graph shows opsin immunogold gold particle density along the length of the connecting cilium. Ultrathin sections of retinas from Myo7a-null and WT mice were stained with rod opsin antibody. The Myo7a-null retinas had been untreated, or treated with either 1× or 1:100 AAV2-MYO7A or AAV5-MYO7A. n=3 animals per condition. Bars indicate SEM.

Myo7a-mutant mice have an abnormal accumulation of opsin in the connecting cilia of the photoreceptor cells, a phenotype that is evident by immunoEM with opsin antibodies (Liu et al., 1999). This mutant phenotype suggested that myosin 7a functions in the vectorial delivery of opsin to the outer segment (Liu et al., 1999). Quantification of immunogold opsin labeling in the connecting cilia, demonstrated that this phenotype was corrected with 1×AAV2-MYO7A or AAV5-MYO7A (FIG. 13; FIG. 21A, FIG. 21B, FIG. 21C, and FIG. 21D). This analysis also showed phenotype correction with 1:100 dilutions, although the data indicated that a full WT phenotype was not achieved (FIG. 13), despite WT levels of MYO7A (FIG. 11J and FIG. 11L), suggesting that some of the MYO7A may not be fully functional.

AAV2 MYO7A Dual-Vector Preparations.

Figures 1, 14A:
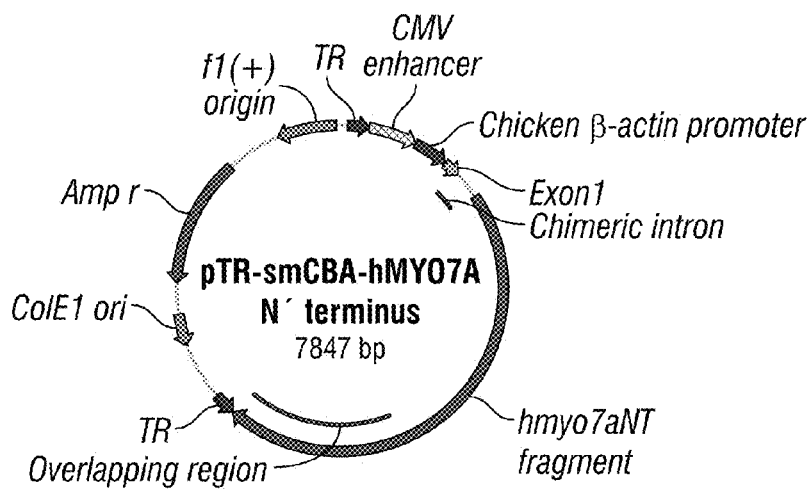
Figures 2, 14A:
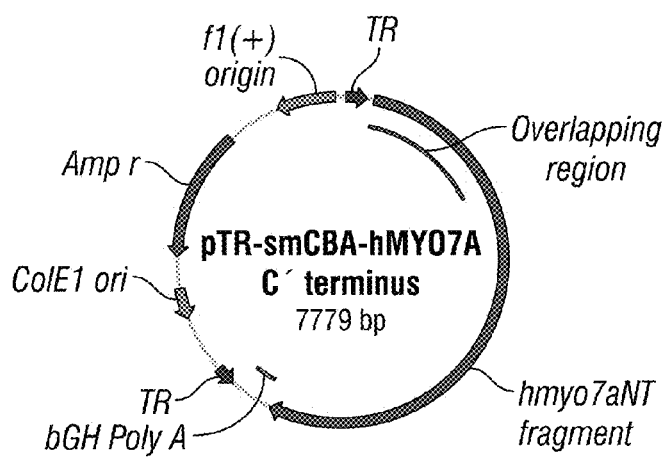

The preceding results demonstrate that a single AAV vector is capable of delivering functional MYO7A to the RPE and photoreceptor cells in vivo. Because the size of smCBA-MYO7A is ~2 kb larger than the nominal carrying capacity of an AAV (Grieger and Samulski, 2005), this transduction may involve undefined fragmentation of the smCBA-MYO7A cDNA followed by reassembly of plus and minus cDNA strands after delivery to the cell as shown for other large genes (Dong et al., 2010; Lai et al., 2010; Wu et al., 2010). To evaluate whether two AAV vectors containing defined, overlapping fragments of MYO7A cDNA (1365 bases) were also capable of mediating full-length MYO7A expression, an AAV2-based dual-vector system (FIG. 14A-1 and FIG. 14A-2) was developed. Two separate lots of the AAV2-MYO7A(dual vector) were prepared, each containing equal concentrations of AAV2-smCBA-MYO7A(5'-half) and AAV2-MYO7A(3'-half). The titer of the first lot contained $2.5 \times 10^{12}$ particles/mL of each vector, and the second lot contained $4 \times 10^{12}$ particles/mL.

MYO7A Expression with AAV2 Dual Vectors.

Figure 14B:
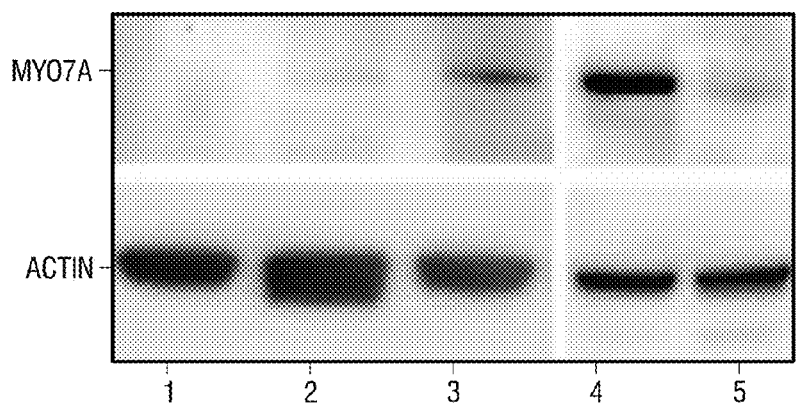

Western blot analysis of primary cultures of Myo7a-null RPE cells, infected with AAV2-MYO7A(dual vector) of either lot, showed that the cells expressed a MYO7A-immunolabeled polypeptide of comparable mass to that of WT MYO7A (FIG. 14B). However, the expression level of MYO7A in the Myo7a-null RPE cells was significantly less than that found in primary cultures of $Myo7a^{+/-}$ RPE cells (cf. lanes 2 and 3 in FIG. 14B), unlike that found for the single AAV2 or AAV5 vectors (FIG. 10B). Quantitative analysis of western blots showed that Myo7a-null RPE cells, transduced with the single vectors (1×), AAV2-MYO7A or AAV5-MYO7A, or with AAV2-MYO7A(dual vector), expressed MYO7A at levels that were 82%, 111%, and 10%, respectively, of the level of MYO7A in $Myo7a^{+/-}$ RPE cells.

Figure 16:
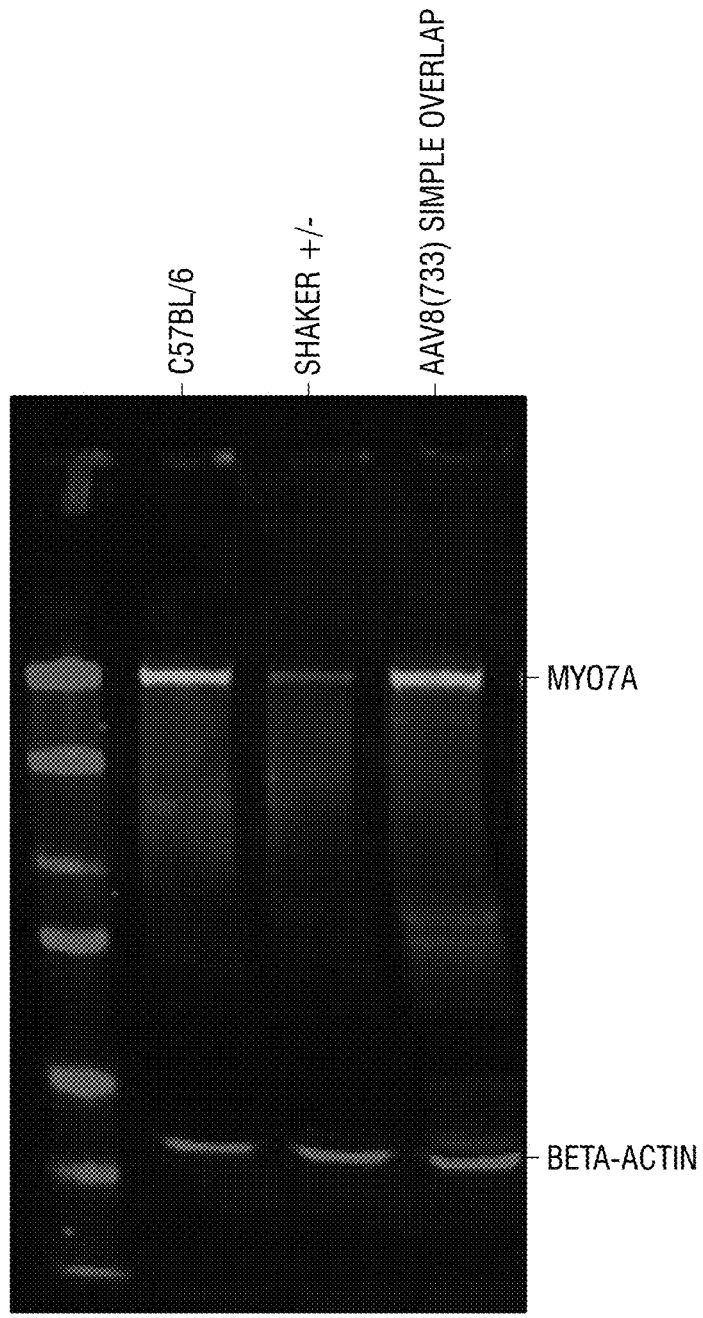
FIG. 16 shows the validation of dual AAV vectors for delivery of full-length MYO7A in vivo. Immunoblot showing expression of MYO7A (green) in retinas of wild type (C57BL/6) mice (lane 1), heterozygous shaker-1$^{+/-}$ mice (lane 2) and shaker-1$^{-/-}$ mice injected with 'simple overlap' Myo7a vectors packaged in AAV8(733) vectors. Both N-terminal and C-terminal vectors of the 'simple overlap' system were injected at a concentration of 3×10$^{10}$ vector genomes/ μL. Dual AAV vectors mediated expression of a MYO7A that was identical in size to that found in WT and shaker-1$^{+/-}$ mice. β-actin (visualized here in red) was used as a loading control to validate that equal amounts of protein were loaded in each well.

FIG. 16 is a Western blot using the same dual-vector system as above except in an AAV8 serotype. FIG. 16 shows expression level of myo7A using the dual-vector system that was nearly equivalent to the wild type myo7A expression level. While the reasons for the discrepancy are unclear, much better results were obtained by the inventors using the dual-vector systems than were obtained by several outside collaborators. Wild type like levels of MYO7A expression was observed in shaker-1 retinas following injection with dual-AAV8(Y733F) vectors. Thus, very good expression of MYO7A with the dual AAV platform has been achieved.

Figure 14G:
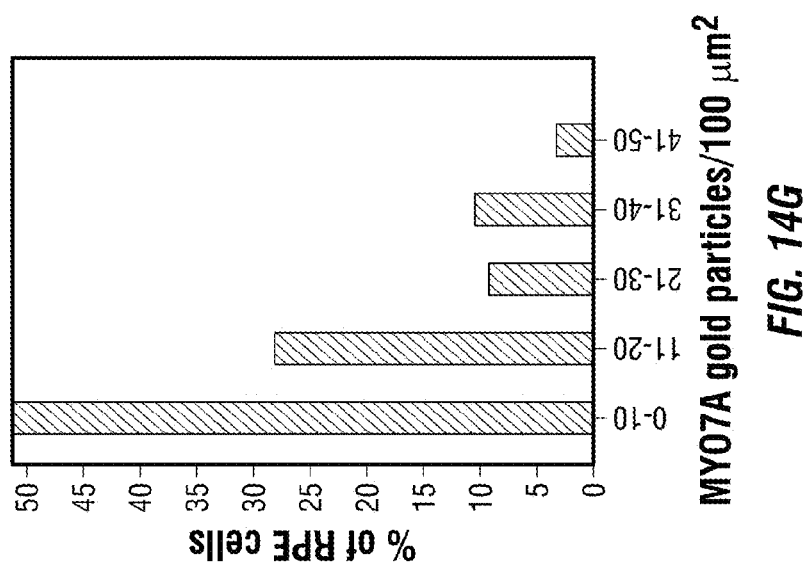
Figure 14C:
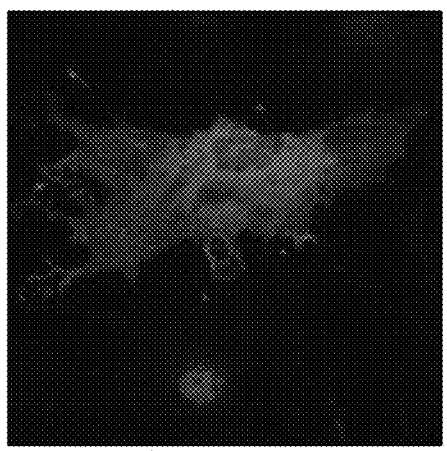
Figure 14D:
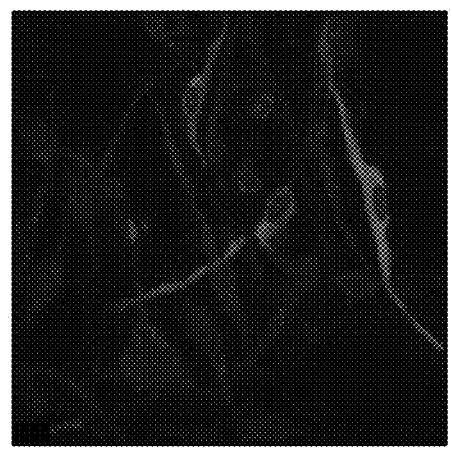
Figure 14E:
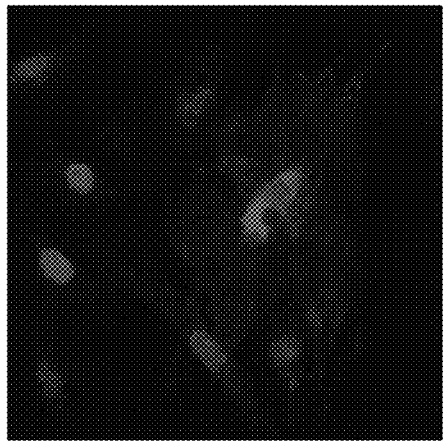
Figure 14F:
Figure 17A:
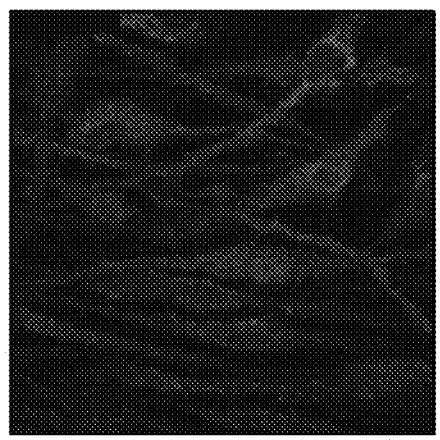
FIG. 17A, FIG. 17B, FIG. 17C, FIG. 17D, FIG. 17E, and FIG. 17F show AAV-mediated MYO7A expression in ARPE-19. Cells were transduced with 1×AAV2-MYO7A (FIG. 17A), AAV5-MYO7A (FIG. 17B), 1/100 dilutions thereof (FIG. 17C and FIG. 17D) and AAV2-MYO7A (dual) (FIG. 17F). Non-transduced cells were used as a control (FIG. 17E); Red, MYO7A; Blue, DAPI. Scale=10 μm.
Figure 17B:
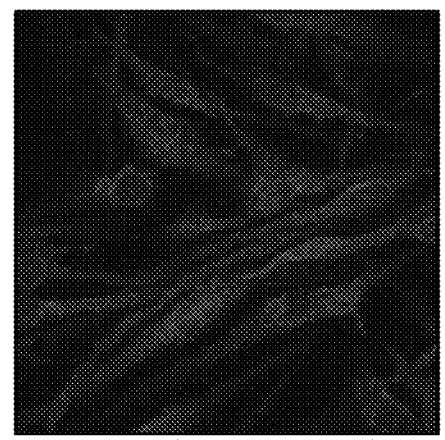
Figure 17C:
Figure 17D:
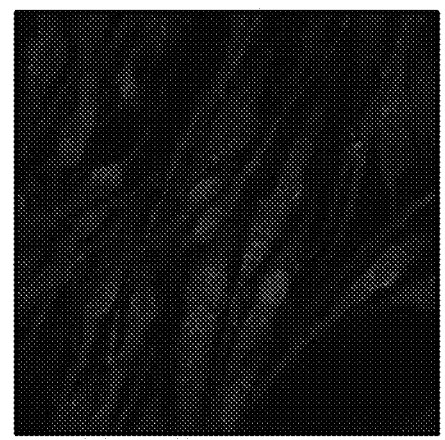
Figure 17E:
Figure 17F:
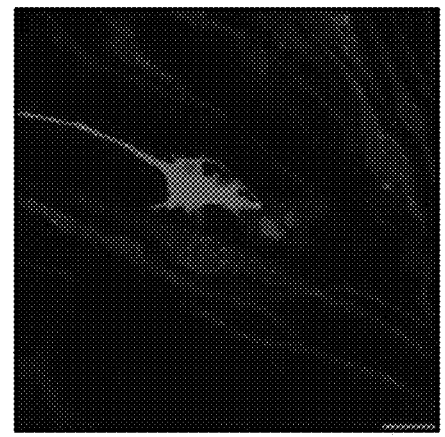

Immunofluorescence of primary Myo7a-null RPE cells, infected with AAV2-MYO7A(dual vector), showed that a few cells scattered throughout the culture exhibited very high levels of MYO7A, but all other cells contained insignificant levels (FIG. 14C, FIG. 14D, and FIG. 14E). The cells overexpressing MYO7A typically had altered morphology, suggesting that the high levels of MYO7A may be toxic. Similarly, immunofluorescence of ARPE19 cells, infected with AAV2-MYO7A(dual vector), resulted in a minority of cells that were labeled intensely with MYO7A antibody, with most of the cells appearing to express only endogenous levels of MYO7A (FIG. 14F and FIG. 17F).

Immunolabeling of retinas, prepared 3 weeks after subretinal injection with AAV2-MYO7A(dual vector) of either lot, also showed only a few RPE cells and photoreceptor cells with clear MYO7A expression, although significant overexpression was not evident in this in vivo experiment Immunogold particle counts from images of ultrathin sections were used to quantify the level of MYO7A expression in Myo7a-null retinas that were treated with the second lot of AAV2-MYO7A(dual vector). Within 1.4 mm of the injection site, MYO7A immunolabeling of the connecting cilium and pericilium of the photoreceptor cells was a mean of 48% of that in WT retinas: 2.8 particles/μm (n=3 retinas) compared with 6.5 particles/μm for WT (n=3 retinas). The mean label density in apical-basal sections of the RPE was 35% of that in WT retinas: 11 particles/100 µm² compared with 31 particles/100 µm² for WT. However, it was clear that these lower means were achieved by some cells expressing near normal amounts of MYO7A and the majority expressing very little; over half the cells had fewer than 10 particles/100 µm² (FIG. 14G).

Correction of Myo7a-Mutant Phenotypes with AAV2 Dual Vectors.

Figure 15A:
FIG. 15A, FIG. 15B, FIG. 15C, FIG. 15D, FIG. 15E, FIG. 15F, and FIG. 15G illustrate correction of mutant phenotypes, following subretinal injections with AAV2-MYO7A (dual).
Figure 15B:
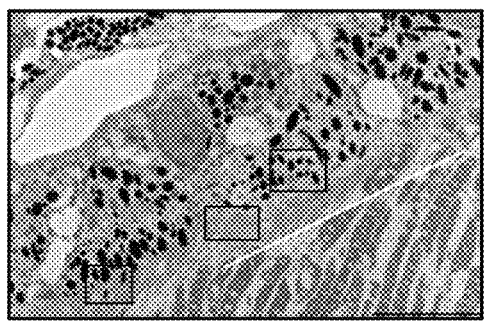
Figure 15C:
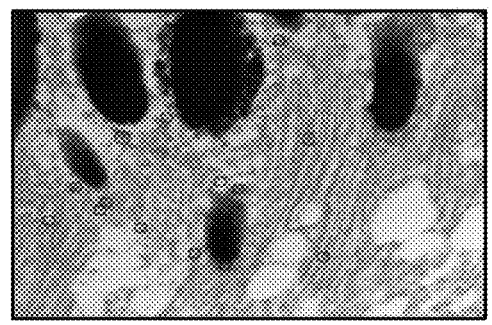
Figure 15D:
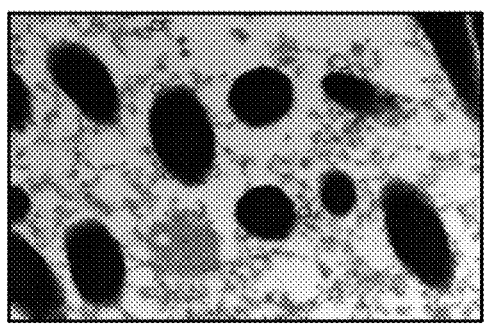
Figure 15E:
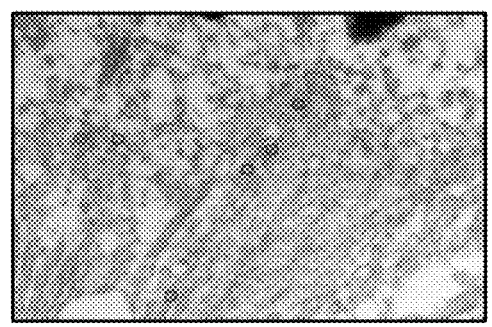

Eyes were analyzed for correction of melanosome localization and ciliary opsin distribution within 1.4 mm of the injection site. With either lot of AAV2-MYO7A(dual vector), some RPE cells (29% for lot 1 treatment [n=6 retinas], 35% for lot 2 treatment [n=9 retinas]) were observed to have a normal apical melanosome distribution, but most of the cells in this region retained the Myo7a-mutant phenotype, resulting in a mosaic effect (FIG. 15A) that contained a much lower proportion of corrected cells than that observed with a 1:100 dilution of either of the single vectors. The only correction observed in 3 eyes injected with a 1:10 dilution of AAV2-MYO7A(dual vector) (first lot), was in 18% of the RPE cells in one of the retinas. With full-strength of AAV2-MYO7A(dual vector) (second lot), opsin immunogold density averaged 3.2±0.4 particles/µm of cilium length, which was reduced from untreated retinas (4.2±0.8 particles/µm; p=0.003), but still greater than WT levels (1.1±0.2 particles/µm), suggesting that most cells were not corrected.

Figure 15F:
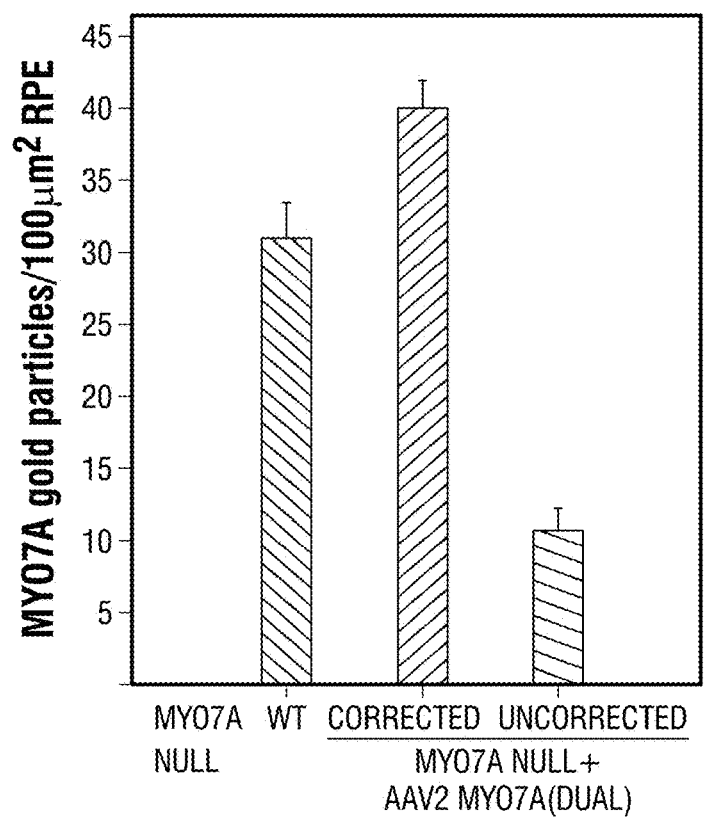
Figure 15G:
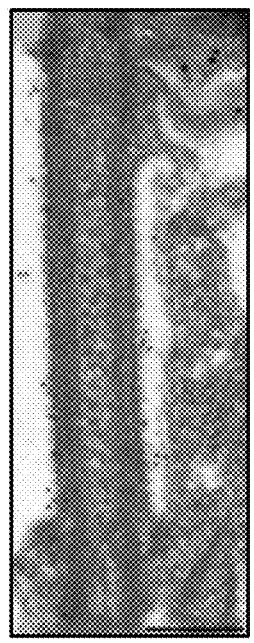

Using immunoelectron microscopy, a correlation between phenotype correction and the expression level of MYO7A was identified (determined by the mean concentration of immunogold particles in an apical-basal section of each RPE cell) (FIG. 15B, FIG. 15C, FIG. 15D, and FIG. 15E). From the eyes injected with AAV2-MYO7A(dual vector) (second lot), it was shown that the corrected RPE cells contained a mean of 108% of the WT level of MYO7A (the minimum level was 82%). RPE cells that were not corrected contained a mean of 26% of the WT level of MYO7A (the maximum level was 92%). While these data showed that higher expression of MYO7A is correlated with phenotype correction (FIG. 15F), it also indicated that some of the labeled MYO7A protein was not functional, given that melanosomes are localized normally in mice that are heterozygous for the Myo7a-null allele and have only ~50% of the WT level of MYO7A.

Expression of MYO7A with Simple Overlap Vectors.

Figure 23A:
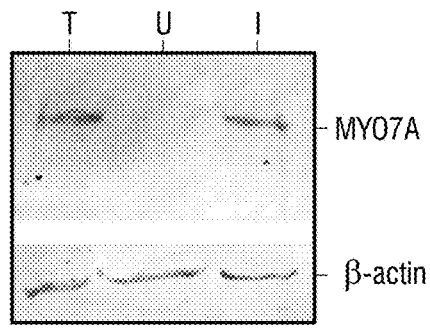
FIG. 23A, FIG. 23B, and FIG. 23C show human embryonic kidney (HEK293) cells express human MYO7A after infection with simple overlap vectors (MOI of 10,000 for both vectors) packaged in AAV2(tripleY-F). Equal amounts of protein were separated on 7.5% sodium dodecyl sulfate (SDS) polyacrylamide gel electrophoresis (PAGE) and stained for MYO7A.
Figure 23B:
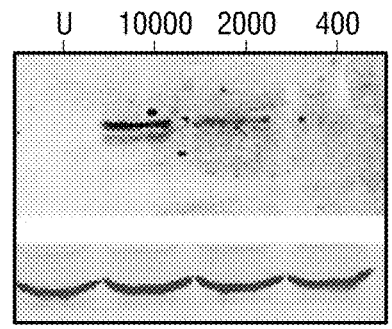
Figure 23C:
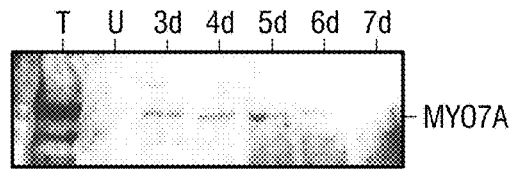

AAV2-based simple overlap vectors were evaluated in vitro at a variety of MOIs to evaluate how the concentration of vector pairs related to MYO7A expression. How levels of MYO7A changed over time was also evaluated in infected cells. HEK293 cells were infected with simple overlap vector pairs packaged in AAV2(tripleY-F) vector (FIG. 23A). A preliminary co-infection with AAV2(tripleY-F) simple overlap vectors (MOI of 10,000 for each vector) indicated that MYO7A is expressed, and that migration of the protein on gel is identical to a full-length transfection control (FIG. 23A). Coinfection at MOIs of 400, 2000, and 10,000 of each vector shows that the efficiency of the simple overlap system is proportional to the amount of 5' and 3' vectors used (FIG. 23B). MYO7A expression increased as a function of incubation time up to 5 days postinjection in HEK293 cells (FIG. 23C). The visible expression decline was because of a reduction of viable cells in the culture vessel at the later times.

Comparison of fAAV-MYO7A to Dual-AAV-MYO7A Expression and Evaluation of AAV Serotype Efficiency.

Figure 24:
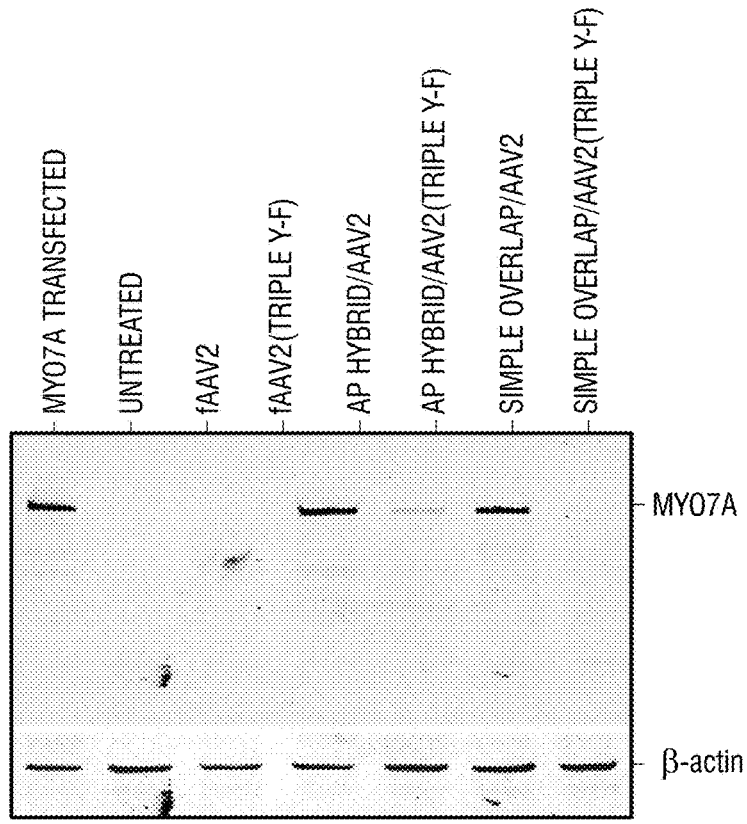
FIG. 24 shows the comparison of AAV2 and AAV2 (tripleY→F mutant capsid)-based vectors in HEK293 cells. Cells were infected with single fAAV, AP hybrid, and simple overlap MYO7A dual-vector platforms packaged in AAV2 or AAV2(tripleY→F mutant capsid) at an MOI of 10,000. HEK293 cells transfected with MYO7A plasmid were used as a positive control.

Previously, it was shown that fAAV-MYO7A was able to ameliorate the retinal phenotype of the shaker1 mouse (Colella et al., 2013; Lopes et al., 2013; Trapani et al., 2013). To provide a basis for comparison dual-AAV-vector expression was evaluated relative to fAAV in vitro. After infection in HEK293 cells, all dual-vector systems expressed MYO7A more efficiently than fAAV (FIG. 24). The AP hybrid platform showed the strongest expression, followed by the simple overlap system.

Other studies have shown, in the context of a conventionally sized DNA payload, that the transduction efficiency and kinetics of AAV2(tripleY-F) vectors are increased relative to standard AAV2 both in vitro and in vivo (Li et al., 2010; Markusic et al., 2010; Ryals et al., 2011). The efficiency of AAV2 versus AAV2(tripleY-F) dual vectors was directly compared in HEK293 cells. Surprisingly, standard AAV2-mediated MYO7A expression was higher than that seen with titer-matched AAV2(tripleY-F) (FIG. 24). Identical results were obtained when comparing different AAV2 and AAV2(tripleY-F) dual-vector preparation packaged with identical vector plasmid.

Comparison of Relative Efficiencies and Specificity of Full-Length MYO7A Expression.

Figure 25A:
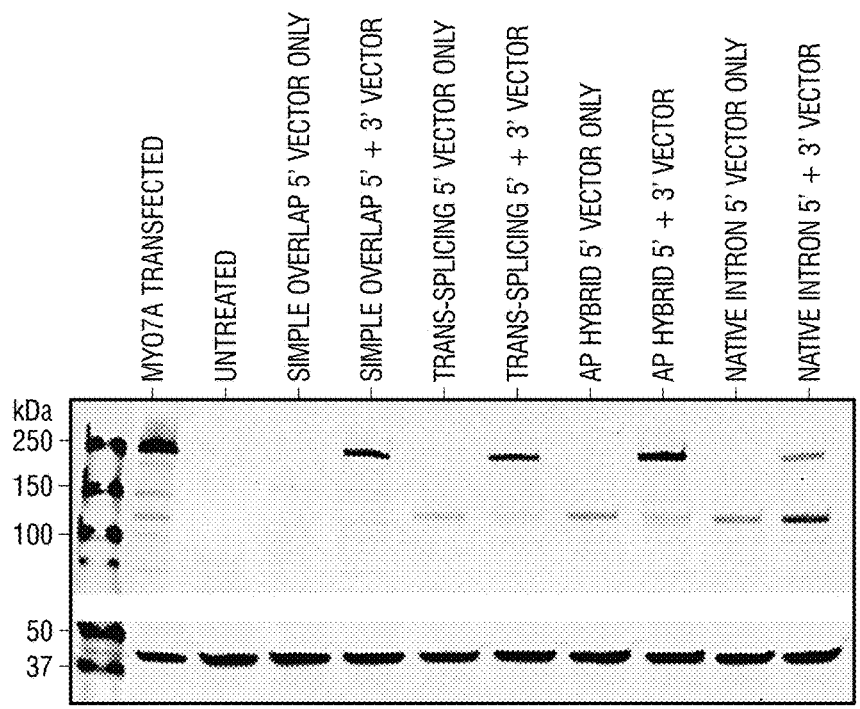
FIG. 25A, FIG. 25B, and FIG. 25C show human MYO7A expressed in HEK293 cells. Cells were infected with AAV2-based vector platforms. For each of the dual-vector systems, the corresponding 5' and 3' vectors (or the 5' vector alone) were used for infection. HEK293 cells transfected with MYO7A plasmid were used as a positive control. Cells were infected with the MYO7A dual-vector pairs at an MOI of 10,000 for each vector. Protein samples were analyzed on Western blot with an antibody against MYO7A (FIG. 25A). Each platform's relative ability to promote reconstitution was compared by quantifying the amount of 5' vector-mediated truncated protein product in the presence or absence of the respective 3' vector (FIG. 25B). Full-length MYO7A expression mediated by dual vectors was quantified relative to transfection control (FIG. 25C)
Figure 25B:
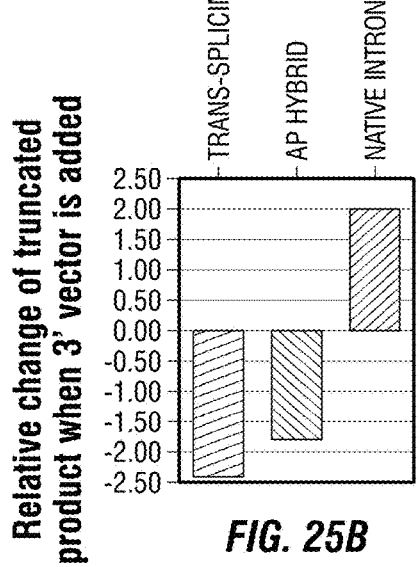
Figure 25C:
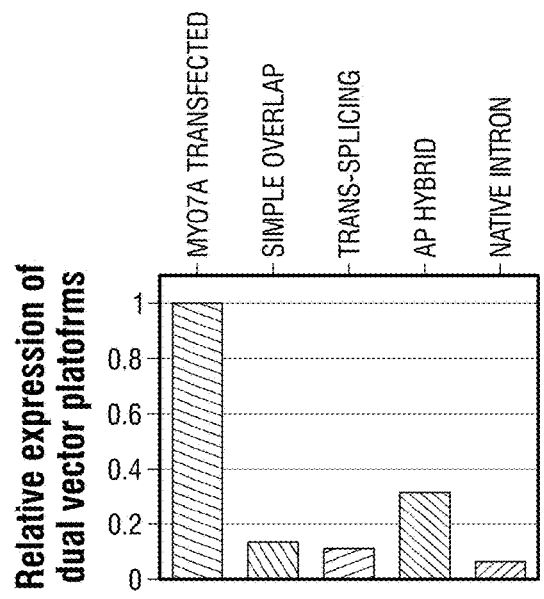

To quantitatively evaluate the relative expression efficiencies of the dual-vector platforms and to assess specificity of full-length protein, HEK293 cells were infected with either the 5' and 3' AAV2-based vector pairs combined or the corresponding 5' vector alone. An additional hybrid vector pair was included that incorporated native MYO7A intronic sequence (intron 23) that served as overlapping sequence and provided appropriate splicing signals. All 5' vectors produced low amounts of a defined, less than full-length peptide detectable on Western blot with the exception of the simple overlap vector (FIG. 25A). However, the trans-splicing and the AP hybrid platforms revealed a distinct decrease of this undesired product when the 3' vector was added to the sample (FIG. 25A). The native intron hybrid platform also showed this secondary band on Western blots, again suggestive of a truncated protein originating from the 5' vector alone. In contrast to all other platforms tested, this band intensity increased with the addition of the 3' vector. Each platform's relative ability to promote reconstitution was compared by quantifying the amount of 5' vector-mediated truncated protein product in the presence or absence of the respective 3' vector (FIG. 25B). Full-length MYO7A expression on Western blot was then quantified relative to transfection control (FIG. 25C). AP hybrid-mediated MYO7A was the strongest followed by simple overlap, trans-splicing, and native intron hybrid (FIG. 25C).

Characterization of the Overlap/Splice Region of the Expressed MYO7A.

Figure 26A:
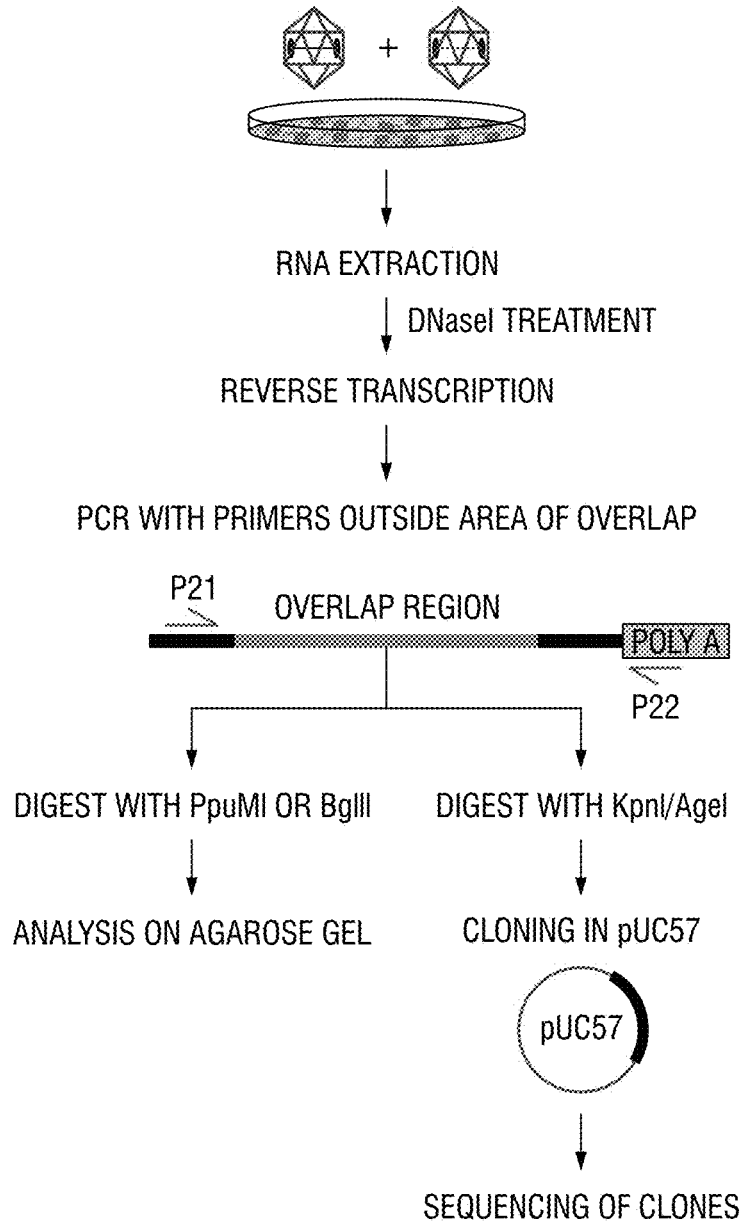
Figure 27A:
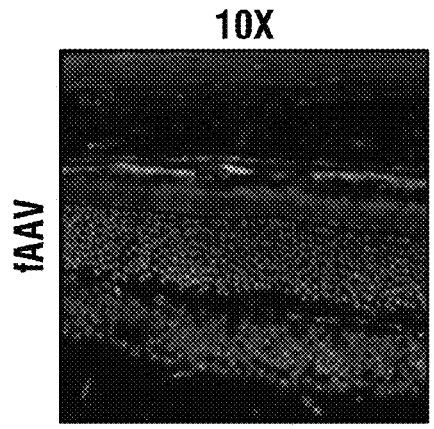
FIG. 27A, FIG. 27B, FIG. 27C, FIG. 27D, FIG. 27E, FIG. 27F, FIG. 27G, and FIG. 27H show the dual vector-mediated MYO7A(HA) expression in vivo. C57BL/6J mice were injected subretinally with AAV2-based dual vectors containing a C' terminal HA tag. Retinal protein expression was analyzed four weeks later by immunohistochemistry and western blot. Ten-micron frozen retinal cross sections were imaged at 10× (FIG. 27A, FIG. 27C, and FIG. 27E) and 60× (FIG. 27B, FIG. 27D, and FIG. 27F). Equal amounts of protein were separated on a 4-15% polyacrylamide gel and stained with an HA antibody (FIG. 27H). For comparison, endogenous MYO7A from C57BL/6J retina (FIG. 27G) was probed with an antibody against MYO7A to confirm that HA-tagged MYO7A migrated at the appropriate size. RPE—retinal pigment epithelium, IS—inner segments, OS—outer segments, ONL—outer nuclear layer, INL—inner nuclear layer, GCL—ganglion cell layer, PR—photoreceptors.
Figure 27B:
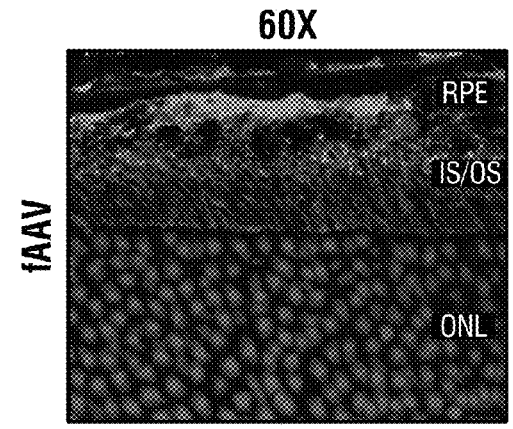
Figure 27C:
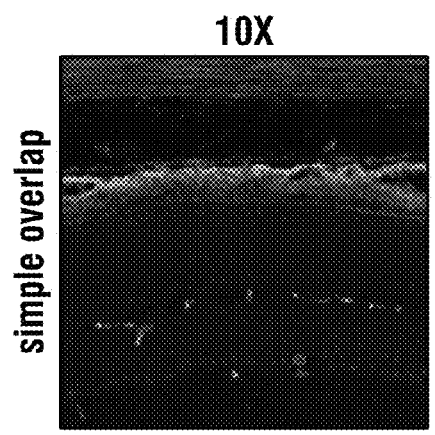
Figure 27D:
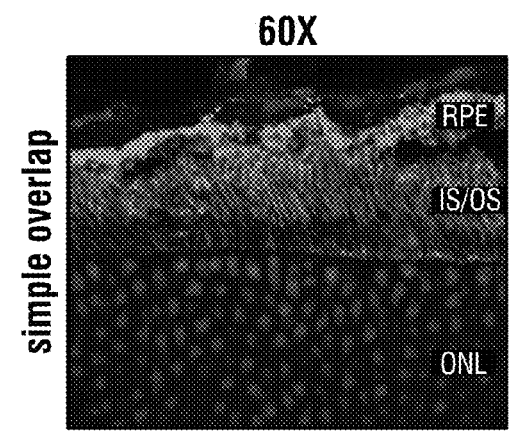
Figure 27E:
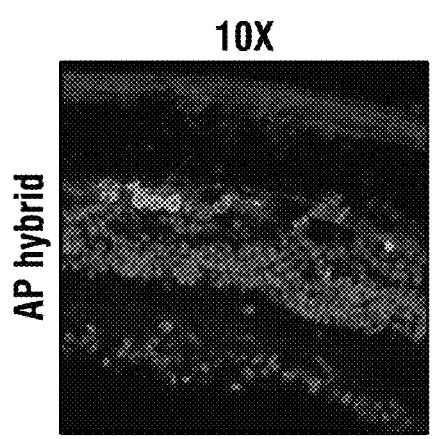
Figure 27F:
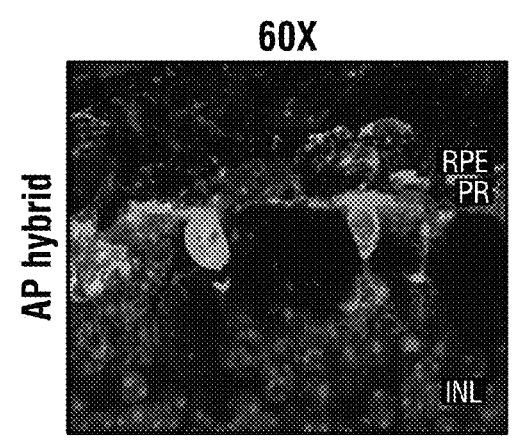
Figure 27G:
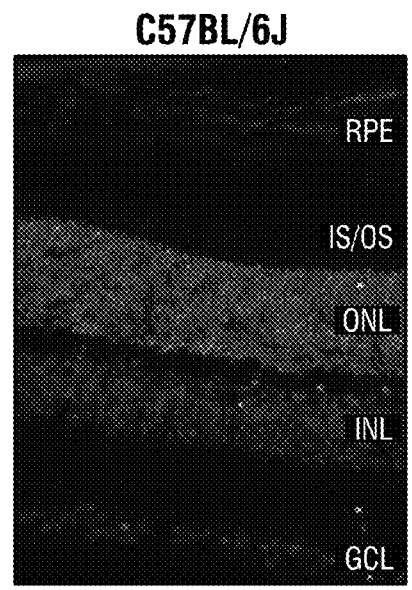
Figure 27H:
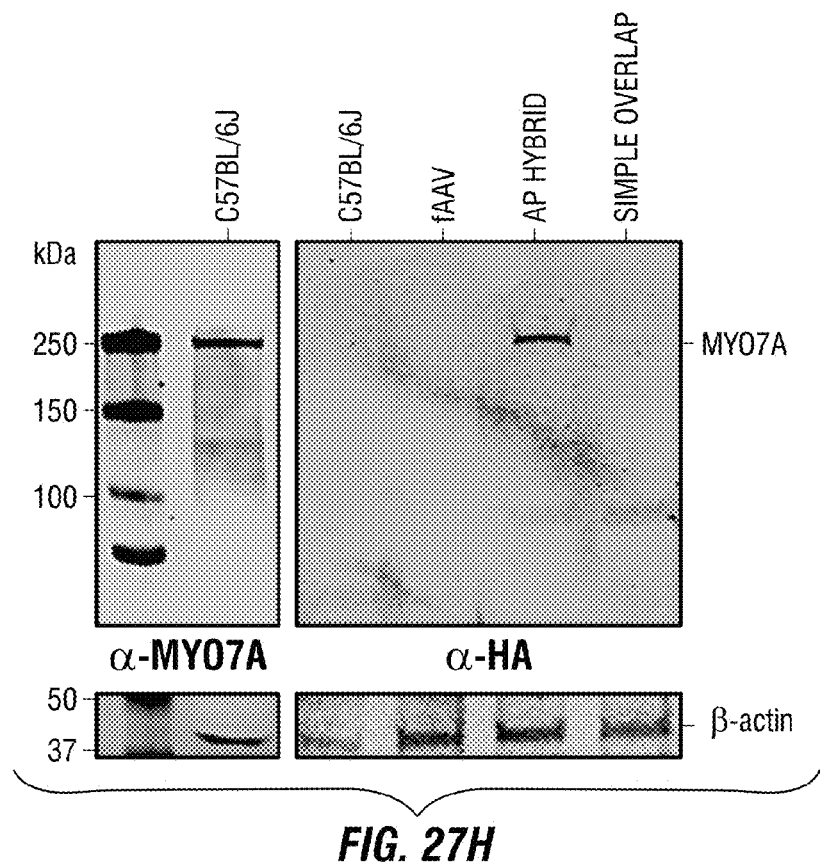

To characterize the fidelity of the mRNA arising from dual vectors, HEK293 cells were infected with dual vectors and RNA extracted, reverse transcribed, and subjected to PCR utilizing primers binding upstream of the overlap region and in the bGH polyA signal region producing a 4.5 kb PCR fragment (FIG. 26A). An identically treated sample not containing reverse transcriptase was used as control for chromosomal DNA contamination. Plasmid containing the full-length MYO7A coding sequence was used as positive control for PCR. A preliminary screen of AAV-mediated MYO7A mRNA was performed by analyzing the pattern of fragment migration on agarose gel following restriction endonuclease digests with PpuMI and BglII (FIG. 26A). Identical banding patterns, consistent with the predicted pattern (PpuMI: 1591, 876, 556, 548, 541, 238, 168, 42, and 36 bp; BglII 1335, 1074, 827, 583, 360, 272, and 146 bp), were observed following digests of amplicons from each dual-vector platform tested, indicating that no gross alterations (deletions/insertions) occurred as a consequence of either homologous recombination of vector pairs and/or RNA splicing (FIG. 26B). To further characterize the fidelity of the overlap region, a fragment containing the complete overlap area (1829 bp) was restricted and cloned into pUC57 (FIG. 26A). Sequencing results of 10 clones picked at random per vector platform revealed that the overlap region was 100% identical to the consensus/predicted MYO7A sequence (FIG. 26C). This indicated that, in the context of the simple overlap platform, homologous recombination was accurate. Additionally, in the context of trans-splicing vectors, accurate splicing occurred. Finally, for the AP hybrid vectors, a combination of accurate homologous recombination and/or splicing took place. To determine whether this protocol was capable of detecting aberrant sequence in reconstituted MYO7A, a sequence that contained either an insertion of a HindIII recognition site (TAGC) at position 2635 or a point mutation (T-C) at position 2381 was also generated.

MYO7A Expression Mediated by Dual Vectors in Mouse Retina.

To investigate the expression of MYO7A from the two best performing dual-vector platforms in vivo, C57BL/6J mice were subretinally injected with $1 \times 10^{10}$ vector genomes per eye of simple overlap and AP hybrid systems packaged in AAV8(733) and analyzed 4 weeks later by Western blot and immunohistochemistry. AAV8(733)-fAAV-MYO7A vector was also injected to provide a basis for comparison. To distinguish between endogenous MYO7A and exogenous expression mediated by vectors, sequence coding for an HA tag was added to the C' terminus of the MYO7A cDNA in all constructs. Resulting retinas were immunostained for HA to reveal that fAAV vector along with both dual-vector platforms mediated expression of MYO7A in photoreceptors and RPE. A recent report concluded that simple overlap vectors were more efficient for gene transfer to the RPE than photoreceptors (Trapani et al., 2013). Simple overlap-mediated MYO7A expression was observed in both RPE and photoreceptors. In contrast to previous results showing "spotty" MYO7A expression mediated by AAV2-based simple overlap vectors (Lopes et al., 2013), it was found, when packaged in AAV8(733), that simple overlap vectors mediated MYO7A expression in the majority of RPE and photoreceptor cells. Photoreceptor degeneration/outer nuclear layer thinning was apparent in eyes injected with the AP hybrid vector system. Despite the observed degeneration, AP hybrid-mediated MYO7A was clearly detected in residual PR cell bodies and RPE and was sufficient to be detected by immunoblot. By Western blot analysis using HA antibody, simple overlap-mediated MYO7A was present in just detectable amounts. In contrast, fAAV-mediated protein levels were insufficient to be detected in this assay. Using an antibody against MYO7A, immunoblot of WT mouse retina revealed that both endogenous MYO7A and dual-vector-mediated, HA-tagged MYO7A migrated similarly.

DISCUSSION

In this example, it was shown that dual AAV vectors with defined genetic payloads can be used to deliver a large transgene in vitro and in vivo. The initial experiments using the simplest of all dual-vector platforms revealed that efficiency of AAV2-based simple overlap vectors is proportional to the amount of 5' and 3' vectors used and that MYO7A expression mediated by this system increased as a function of incubation time in HEK293 cells. Next, three distinct dual-vector platforms were evaluated and compared to single, fragmented fAAV vector in vitro. All dual vectors analyzed drove higher levels of MYO7A expression than fAAV. Of all platforms tested, a hybrid vector system containing overlapping, recombinogenic sequence and splice donor/acceptor sites from the AP gene (AP hybrid) was the most efficient.

Regarding the specificity with which the dual-vector platforms express the correct-sized gene product, it was noted in vitro that trans-splicing and hybrid dual-vector platforms generated an additional band of lower molecular weight as detected by immunoblot (monoclonal antibody used was raised against the amino terminus MYO7A). The expression of this truncated product was much more pronounced for infections with 5' vectors alone. What might account for this additional band? After entry into the host cell, the virus capsid is removed and the single-stranded DNA payload is released. The ITRs carried by the single strand serve as primer for DNA polymerases to produce a double strand. The resulting circular intermediates consist mainly of monomers that, over time, convert into multimeric concatemers through intermolecular recombination (Duan et al., 1998; Yang et al., 1999). The dual-vector systems created in this study utilize this strategy to achieve full-length protein expression. A limiting factor lies in the fact that the highly recombinogenic ITRs flanking the expression cassettes are identical in nature leading to a random recombination and consequently a random orientation of the vector parts relative to each other. This random recombination inevitably results in reduced efficiency because only concatemers that have the two vector parts in 5'-3' orientation are able to express the full-length protein. This concatemerization over time is consistent with the observation that the amount of single-vector product is reduced in favor of the full-length protein when both 5' and 3' vectors are combined. Interestingly, the simple overlap system does not generate truncated product, even when only the 5' vector is used for infections. In contrast to the trans-splicing and hybrid vectors, there is virtually no intervening sequence between the end of the MYO7A coding sequence and the right-hand ITR. It may be that splice donor sequences enhance the likelihood of truncated product through some as-yet-to-be-determined mechanism.

A number of strategies have been devised to overcome the issue of random concatemerization and thereby increase specificity as well as efficiency of these dual-vector platforms. First, the addition of a highly-recombinogenic sequence such as that used in the AP hybrid vector here has resulted in significantly increased protein expression compared with the trans-splicing system. Ghosh et al. (2011) provide a detailed analysis of the 270-bp AP sequence used in this study as well as other sequences derived from AP that direct recombination and lead to significant improvement over trans-splicing vectors. The finding that AP hybrid vectors are more efficient than trans-splicing vectors supports that the AP sequence directs at least some of the concatemerization events toward the proper orientation with recombination then occurring via this sequence or via the ITRs. Regardless, with more concatemers properly aligned, the AP hybrid system mediates a more-efficient expression of MYO7A. Another approach for directing concatemerization is the use of single-strand oligonucleotides that are capable of tethering the back end of the 5' vector and the front end of the 3' vector together (Hirsch et al., 2009). However, this strategy requires efficient delivery of the oligonucleotide to the nucleus of the target cells timed with the dual vectors. Finally, dual vectors utilizing mismatched ITRs can be used to direct concatemerization in a head-totail orientation (Yan et al., 2005), although the process may require further optimization of the AAV packaging machinery.

Notably, in this study, it was found that the sequence in the overlap region of all dual vectors tested in vitro was 100% identical to the consensus/predicted MYO7A sequence. This indicates that homologous recombination and/or splicing was accurate in each dual-vector platform.

Similar to the in vitro results, the highest levels of MYO7A expression was found in retinas of mice subretinally injected with AAV8-based AP hybrid vectors (as assessed by probing for HA on Western blot). Notably, no truncated proteins were evident in retinas expressing either simple overlap or AP-hybrid mediated MYO7A. The reason for this observed difference remains to be elucidated but may involve differences in the DNA repair machinery that mediate recombination in actively dividing cells versus post-mitotic photoreceptors/RPE (Hirsch et al., 2013). Dual-vector-mediated MYO7A-HA expression was observed in the photoreceptors and RPE of WT mice, locations where MYO7A is thought to have a functional role (Williams and Lopes, 2011). In eyes injected with AP hybrid vectors, marked thinning of the outer nuclear layer was observed. It has previously been shown that vector-mediated overexpression of MYO7A leads to retinal toxicity (Hashimoto et al. 2007). Taken together with the high efficiency of transduction observed in vitro for the AP hybrid platform, the most likely explanation for the observed pathology is excessive production of MYO7A. Despite the marked degeneration, significant amounts of AP hybrid-mediated, full-length MYO7A-HA were detected on Western blot. As high concentrations of vectors were used in these experiments, a simple solution to circumvent toxicity could be to reduce vector genomes injected or replace the strong, ubiquitous smCBA promoter with an endogenous or homologous promoter, and/or a promoter with attenuated strength. An alternative explanation for toxicity of the strong AP hybrid platform is expression of undesired products, like the observed protein expressed from the 5' vectors alone in vitro. However, it was noted that only full-size MYO7A-HA was apparent on Western blot of the AP hybrid-treated retina.

With the goal of developing an AAV-based treatment for USH1B, animal models of this disease have provided an abundance of useful information. Similar to previous observations that fAAV-MYO7A and simple-overlap, dual-vectors were capable of restoring melanosome migration and opsin localization in the shaker1 mouse (Lopes et al., 2013), a recent study by an independent lab confirmed the usefulness of the vectors disclosed herein, when it was reported that they were capable of restoring the ultrastructural retinal phenotypes in the animal model. Notably, shaker1 mice lack retinal degeneration, and the severe functional abnormalities seen in USH1B patients (Liu et al., 1997). This fact renders in vivo analysis of therapeutic outcomes in the shaker1 retina problematic. Alternative animal models for evaluating a treatment for this devastating disease may be useful in adaptation of the present methods to human clinical use.

These results presented here also demonstrated that MYO7A can be efficiently expressed using dual-AAV-vector systems. The platforms containing overlapping elements, namely, the simple overlap system, and the AP hybrid system were both highly efficient. AP hybrid vectors showed the strongest expression of all systems tested, with little observable truncated protein in vitro and none observed in vivo. Simple overlap vectors showed good expression and were the most specific (no truncated protein products were observed) even when the 5'-only vector was used to infect cells. AAV has emerged as the preferred clinical vector and it efficiently transduces both photoreceptors and RPE. Because it has now been demonstrated that MYO7A sequence fidelity is preserved following recombination and/or splicing of dual-AAV-vector platforms and because only full-length MYO7A was detectable in mouse retinas injected with dual vectors, the dual-AAV-vector strategy presented herein represents a valid option for the treatment of retinal disorders associated with mutations in large genes such as USH1B.

REFERENCES

The following references, to the extent that they provide exemplary procedural or other details supplementary to those set forth herein, are specifically incorporated herein by reference:

U.S. Pat. No. 6,204,251.
U.S. Pat. No. 6,461,606.
U.S. Pat. No. 6,106,826.
U.S. Pat. No. 8,137,962.
U.S. Pat. No. 6,967,018.
U.S. Pat. No. 8,298,818.
Allocca, M et al., "Serotype-dependent packaging of large genes in adeno-associated viral vectors results in effective gene delivery in mice," *J. Clin. Invest.*, 118(5):1955-1964 (2008).
Altschul, S F et al., "Basic local alignment search tool," *J. Mol. Biol.*, 215:403-410 (1990).
Altschul, S F et al., "Gapped BLAST and PSI-BLAST: A new generation of protein database search programs," *Nucl. Acids Res.*, 25:3389-3402 (1997).
Astuto, L M et al., "Genetic heterogeneity of Usher syndrome: analysis of 151 families with Usher type 1," *Am. J. Hum. Genet.*, 67:1569-1574 (2000).
Bainbridge, J W et al., "Effect of gene therapy on visual function in Leber's congenital amaurosis," *N. Engl. J. Med.*, 358:2231-7739 (2008).
Beltz, G A et al., "Isolation of multigene families and determination of homologies by filter hybridization methods," *Meth. Enzymol.*, 100:266-285 (1983).
Bharadwaj, A K et al., "Evaluation of the myosin VILA gene and visual function in patients with Usher syndrome type I," *Exp. Eye Res.*, 71:173-181 (2000).
Bowles, D E et al., "Phase I gene therapy for Duchenne muscular dystrophy using a translational optimized AAV vector," *Mol. Ther.*, 20:443-455 (2012).
Boye, S E et al., "A comprehensive review of retinal gene therapy," *Mol. Ther.*, 21:509-519 (2013).
Boye, S L et al., "AAV-mediated gene therapy in the guanylate cyclase (RetGC1/RetGC2) double knockout mouse model of Leber congenital amaurosis," *Hum. Gene Ther.*, 24:189-202 (2012).
Boye, S L et al., "Long-term preservation of cone photoreceptors and restoration of cone function by gene therapy in the guanylate cyclase-1 knockout (GCIKO) mouse," *Invest. Ophthalmol. Vis. Sci.*, 52:7098-7108 (2011).
Chen, Z Y et al., "Molecular cloning and domain structure of human myosin-VIIa, the gene product defective in Usher syndrome 1B," *Genomics*, 36:440-448 (1996).
Cideciyan, A V et al., "Human RPE65 gene therapy for Leber congenital amaurosis: persistence of early visual improvements and safety at 1 year," *Hum. Gene Ther.*, 20:999-1004 (2009),
Dong, B et al., "Characterization of genome integrity for oversized recombinant AAV vector," *Mol. Ther.*, 18(1): 87-92 (2010).

Duan, D et al., "Circular intermediates of recombinant adeno-associated virus have defined structural characteristics responsible for long-term episomal persistence in muscle tissue," *J. Virol.*, 72:8.5684577 (1998).

Duan, D et al., "Expanding AAV packaging capacity with trans-splicing or overlapping vectors: a quantitative comparison," *Mol. Ther.*, 4:383-391 (2001).

Duan, D et al., "Trans-splicing vectors expand the packaging limits of adeno-associated virus for gene therapy applications," *Methods Mol. Med.*, 76:287-307 (2003).

Dyka, F M et al., "Dual adeno-associated virus vectors result in efficient in vitro and in vivo expression of an oversized gene, MYO7A," *Hum. Gene Ther. Methods*, 25(2):166-177 (2014).

Esumi, N et al., "Analysis of the VMD2 promoter and implication of E-box binding factors in its regulation," *J. Biol. Chem.*, 279:19064-19073 (2004).

Felgner, P L et al., "Lipofection: a highly efficient, lipid-mediated DNA-transfection procedure," *Proc. Nat'l. Acad. Sci. USA*, 84(21):7413-7417 (1987).

Flotte, T R et al., "Phase 2 clinical trial of a recombinant adeno-associated viral vector expressing alpha1-antitrypsin: interim results," *Hum. Gene Ther.*, 22:1239-1247 (2011),

*Gene Therapy: Principles and Applications*, Blankenstein, T. (Ed.), Birkhauser-Verlag, Basel, Switzerland (1999).

Ghosh, A et al., "A hybrid vector system expands adeno-associated viral vector packaging capacity in a transgene-independent manner," *Mol. Ther.*, 16:124-130 (2008).

Ghosh, A et al., "Efficient transgene reconstitution with hybrid dual AAV vectors carrying the minimized bridging sequences," *Hum. Gene Ther.*, 22:77-83 (2011).

Gibbs, D and Williams, D S, "Isolation and culture of primary mouse retinal pigmented epithelial cells," *Adv. Exp. Med. Biol.*, 533:347-352 (2003b).

Gibbs, D et al., "Abnormal phagocytosis by retinal pigmented epithelium that lacks myosin VIIa, the Usher syndrome 1B protein," *Proc. Nat'l. Acad. Sci. USA*, 100:6481-6486 (2003a).

Gibbs, D et al., "Role of myosin VIIa and Rab27a in the motility and localization of RPE melanosomes," *J. Cell Sci.*, 117:6473-6483 (2004).

Gibson, F et al., "A type VII myosin encoded by mouse deafness gene shaker-1," *Nature*, 374:62-64 (1995).

Grieger, J C and Samulski, R J, "Packaging capacity of adeno-associated virus serotypes: impact of larger genomes on infectivity and postentry steps," *J. Virol.*, 79:9933-9944 (2005).

Haire, S E et al., "Light-driven cone arrestin translocation in cones of postnatal guanylate cyclase-1 knockout mouse retina treated with AAV-GC1," *Invest. Ophthalmol. Vis. Sci.*, 47:3745-3753 (2006).

Halbert, C L et al., "Efficient mouse airway transduction following recombination between AAV vectors carrying parts of a larger gene," *Nat. Biotechnol.*, 20:697-701 (2002).

Hashimoto, T et al., "Lentiviral gene replacement therapy of retinas in a mouse model for Usher syndrome type 1B," *Gene Ther.*, 14(7):584-594 (2007).

Hasson, T et al., "Effects of shaker-1 mutations on myosin-VIIa protein and mRNA expression," *Cell Motil. Cytoskeleton*, 37:127-138 (1997).

Hasson, T et al., "Expression in cochlea and retina of myosin VIIa, the gene product defective in Usher syndrome type 1B," *Proc. Nat'l. Acad. Sci. USA*, 92:9815-9819 (1995).

Hauswirth, W W et al., "Treatment of Leber congenital amaurosis due to RPE65 mutations by ocular subretinal injection of adeno-associated virus gene vector: short-term results of a phase I trial," *Hum. Gene Ther.*, 19:979-990 (2008).

Hirsch, M L et al., "AAV recombineering with single strand oligonucleotides," *PLoS One* 4:e7705 (2009).

Hirsch, M L et al., "Little vector, big gene transduction: fragmented genome reassembly of adeno-associated virus," *Mol. Ther.*, 18(1):6-8 (2010).

Hirsch, M L et al., "Oversized AAV transduction. is mediated via a DNA-PKcs-independent, Rad51C-dependent repair pathway," *Mol. Ther.*, 21:2205-2216 (2013).

Jacobson, S G et al., "Retinal disease course in Usher syndrome 1B due to MYO7A mutations," *Invest. Ophthalmol. Vis. Sci.*, 52:7924-7936 (2011).

Jacobson, S G et al., "Safety of recombinant adeno-associated virus type 2-RPE65 vector delivered by ocular subretinal injection," *Molec. Ther.*, 13:1074-1084 (2006).

Jacobson, S G et al., "Usher syndromes due to MYO7A, PCDH L5, USH2A or GPR98 mutations share retinal disease mechanism," *Hum. Mol. Genet.*, 17:2405-2415 (2008).

Kapranov, P et al., "Native molecular state of adeno-associated viral vectors revealed by single-molecule sequencing," *Hum. Gene Ther.*, 23:46-55 (2012).

Karlin, S and Altschul, S F "Applications and statistics for multiple high-scoring segments in molecular sequences," *Proc. Nat'l. Acad. Sci. USA*, 90:5873-5877 (1993).

Karlin, S and Altschul, S F, "Methods for assessing the statistical significance of molecular sequence features by using general scoring schemes," *Proc. Nat'l. Acad. Sci. USA*, 87:2264-2268 (1990).

Keats, B J and Corey, D P "The usher syndromes," *Am. J. Med. Genet.*, 89:158-166 (1999).

Klomp, A E et al., "Analysis of the linkage of MYRIP and MYO7A to melanosomes by RAB27A in retinal pigment epithelial cells," *Cell Motil. Cytoskeleton*, 64:474-487 (2007).

Lai, Y et al., "Design of trans-splicing adeno-associated viral vectors for Duchenne muscular dystrophy gene therapy," *Methods Mol. Biol.*, 433:259-275 (2008).

Lai, Y et al., "Efficient in vivo gene expression by trans-splicing adeno-associated viral vectors," *Nat. Biotechnol.*, 23:1435-1439 (2005).

Lai, Y et al., "Evidence for the failure of adeno-associated virus serotype 5 to package a viral genome ≥8.2 kb," *Mol. Ther.*, 18(1):75-79 (2010).

Lai, Y et al., "Synthetic intron improves transduction efficiency of trans-splicing adeno-associated viral vectors," *Hum. Gene Ther.*, 17:1036-1042 (2006).

Li, M et al., "High-efficiency transduction of fibroblasts and mesenchymal stem cells by tyrosine-mutant AAV2 vectors for their potential use in cellular therapy," *Hum. Gene Ther.*, 21:1527-1543 (2010).

Liu, X et al., "Mutant myosin VIIa causes defective melanosome distribution in the RPE of shaker-1 mice," *Nat. Genet.*, 19:117-118 (1998).

Liu, X et al., "Myosin VIIa participates in opsin transport through the photoreceptor cilium," *J. Neurosci.*, 19:6267-6274 (1999).

Liu, X et al., "Myosin VIIa, the product of the Usher 1B syndrome gene, is concentrated in the connecting cilia of photoreceptor cells," *Cell Motil. Cytoskel.*, 37:240-252 (1997).

Liu, X Z et al., "Mutations in the myosin VIIA gene cause non-syndromic recessive deafness," *Nat. Genet.*, 16:188-190 (1997), Lopes, V S et al., "Retinal gene therapy with a large MYO7A cDNA using adeno-associated virus," *Gene Ther.*, 20:824433 (2013).

Lopes, V S et al., "The ternary Rab27a-Myrip-Myosin VIIa complex regulates melanosome motility in the retinal pigment epithelium," *Traffic*, 8:486-499 (2007).

Lopes, V S et al., "The Usher 1B protein, MYO7A, is required for normal localization and function of the visual retinoid cycle enzyme, RPE65," *Hum. Mol. Genet.*, 20(13):2560-2570 (2011).

Lostal, W et al., "Efficient recovery of dysferlin deficiency by dual adeno-associated vector-mediated gene transfer," *Hum. Mol. Genet.*, 19:1897-1907 (2010).

Maguire, A M et al., "Age-dependent effects of RPE65 gene therapy for Leber's congenital amaurosis: a phase 1 dose-escalation trial," *Lancet*, 374:1597-1605 (2009).

Markusic, D M et al., "High-efficiency transduction and correction of murine hemophilia B using AAV2 vectors devoid of multiple surface-exposed tyrosines," *Mol. Ther.* 18:2048-2056 (2010).

*Molecular Cloning: A Laboratory Manual*, (Maniatis, T, Fritsch, E F, and Sambrook, J), Cold Spring Harbor Laboratory, Cold Spring Harbor, N.Y. (1982).

Nathwani, A C et "Adenovirus-associated virus vector-mediated gene transfer in hemophilia B," *N. Engl. J. Med.*, 365:2357-2365 (2011).

Ouyang, X M et al., "Characterization of Usher syndrome type I gene mutations in an Usher syndrome patient population," *Hum. Genet*, 116:292-299 (2005).

Pang, J J et al., "Comparative analysis of in vivo and in vitro AAV vector transduction in the neonatal mouse retina: effects of serotype and site of administration," *Vision Res.*, 48:377-385 (2008).

Petrs Suva H et al, "High-efficiency transduction of the mouse retina by tyrosine-mutant AAV serotype vectors," *Mol. Ther.* 17:461-471 (2009).

Petrs-Silva, H et al., "Novel properties of tyrosine-mutant AAV2 vectors in the mouse retina," *Mol. Ther.*, 19:293-301 (2011).

Ryals, R C et al., "Quantifying transduction efficiencies of unmodified and tyrosine capsid mutant AAV vectors in vitro using two ocular cell lines," *Mol. Vis.*, 17:1090-1102 (2011), Sahly, I et al, "Localization of Usher 1 proteins to the photoreceptor calyceal processes, which are absent from mice," *J. Cell Biol.*, 199:381-399 (2012).

Saihan, Z et al., "Update on Usher syndrome," *Curr. Opin. Neurol.* 22:19-27 (2009).

Simonelli, F et al., "Gene therapy for Leber's congenital amaurosis is safe and effective through 1.5 years after vector administration," *Mol. Ther.*, 18:643-650 (2010).

Smith, R J et al., "Clinical diagnosis of the Usher syndromes," *Usher Syndrome Consortium. Am. J. Med. Genet.*, 50:32-38 (1994).

Soni, L E et al., "The unconventional myosin-VIIa associates with lysosomes," *Cell Motil. Cytoskeleton*, 62:13-26 (2005).

Timmers, A M et of, "Subretinal injections in rodent eyes: effects on electrophysiology and histology of rat retina," *Mol. Vis.*, 7:131-137 (2001).

Trapani, I et al., "Effective delivery of large, genes to the retina by dual AAV vectors," *EMBO Mol. Med.*, 6:194-211 (2013), Weil, D et al., "Defective myosin VIIA gene responsible for Usher syndrome type 1B," *Nature*, 374:60-61 (1995).

Weil, D et al., "Human myosin VIIA responsible for the Usher 1B syndrome: a predicted membrane-associated motor protein expressed in developing sensory epithelia," *Proc. Nat'l. Acad. Sci. USA*, 93:3232-3237 (1996).

Williams, D S and Lopes, V S "The many different cellular functions of MYO7A in the retina," *Biochem. Soc. Trans.*, 39:1207-1210 (2011).

Williams, D S, "Usher syndrome: Animal models, retinal function of Usher proteins, and prospects for gene therapy," *Vision Res.*, 48:433-441 (2008).

Wolfrum, U et al., "Myosin VIIa as a common component of cilia and microvilli," *Cell Motil. Cytoskeleton*, 40:261-271 (1998).

Wu, Z et al., "Effect of genome size on AAV vector packaging," *Mol. Ther.*, 18(1):80-86 (2010).

Yan, Z et al., "Inverted terminal repeat sequences are important for intermolecular recombination and circularization of adeno-associated virus genomes," *J. Virol.*, 79:364-379 (2005).

Yan, Z et al., "Recombinant AAV-mediated gene delivery using dual vector heterodimerization," *Methods Enzymol.*, 346:334-357 (2002).

Yan, Z et al., "Trans-splicing vectors expand the utility of adeno-associated virus for gene therapy," *Proc. Nat'l. Acad. Sci. USA*, 97:6716-6721 (2000).

Yang, J. et al., "Concatamerization of adeno-associated virus circular genomes occurs through intermolecular recombination," *J. Virol.*, 73:9468-9477 (1999).

Zhang, Y and Duan, D "Novel mini-dystrophin gene dual adeno-associated virus vectors restore neuronal nitric oxide synthase expression at the sarcolemma," *Hum. Gene Ther.*, 23:98-103 (2012).

Zhong, L et al., "Next generation of adeno-associated virus 2 vectors: point mutations in tyrosines lead to high-efficiency transduction at lower doses," *Proc. Nat'l. Acad. Sci. USA*, 105(22):7827-7832 (2008).

Zolotukhin, S et al., "Production and purification of serotype 1, 2, and 5 recombinant adeno-associated viral vectors," *Methods*, 28:158-167 (2002).

It should be understood that the examples and embodiments described herein are for illustrative purposes only and that various modifications or changes in light thereof will be suggested to persons skilled in the art and are to be included within the spirit and purview of this application and the scope of the appended claims.

All references cited herein (including publications, patent applications and patents) are incorporated by reference to the same extent as if each reference was individually and specifically incorporated by reference, and was set forth in its entirety herein.

Recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order, unless otherwise indicated herein, or unless otherwise clearly contradicted by context.

The use of any examples, or exemplary language (e.g., "such as") provided herein, is intended merely to better illustrate the invention and does not pose a limitation on the scope of the invention unless otherwise indicated. No language in the specification should be construed as indicating any element is essential to the practice of the invention unless as much is explicitly stated.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

All of the compositions and methods disclosed and claimed herein can be made and executed without undue experimentation in light of the present disclosure. While the compositions and methods of this invention have been described in terms of preferred embodiments, it will be apparent to those of ordinary skill in the art that variations may be applied to the compositions and/or methods disclosed herein, and/or to the steps or the sequence of steps of the methods described herein without departing from the concept, spirit and/or scope of the invention. More specifically, it will be apparent that certain agents that are chemically- and/or physiologically-related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A polynucleotide vector system comprising i) a first AAV vector polynucleotide comprising an inverted terminal repeat at each end of the polynucleotide, and between the inverted terminal repeats a promoter followed by a partial coding sequence that encodes an N-terminal part of a selected full-length polypeptide, and ii) a second AAV vector polynucleotide comprising an inverted terminal repeat at each end of the polynucleotide, and between the inverted terminal repeats a partial coding sequence that encodes a C-terminal part of the selected full-length polypeptide, and optionally followed by a polyadenylation (pA) signal sequence, wherein the polynucleotide sequence encoding the polypeptide sequence in the first and second AAV vectors comprises polynucleotide sequence that overlaps, wherein the encoded polypeptide is human myosin VIIa, and wherein the first AAV vector polynucleotide comprises the nucleotide sequence of SEQ ID NO:1, and the second AAV vector polynucleotide comprises the nucleotide sequence of SEQ ID NO:2.

2. A virus or an infectious viral particle comprising the first AAV vector polynucleotide or the second AAV vector polynucleotide of claim 1.

3. The virus or virion of claim 2, characterized as an adeno-associated virus (AAV) or an infectious AAV viral particle.

4. The virus or virion of claim 2, comprising one or more tyrosine-to-phenylalanine (Y→F) mutations in a capsid protein of the virus or virion.

5. The virus or virion of claim 3, comprising one or more tyrosine-to-phenylalanine (Y→F) mutations in a capsid protein of the virus or virion at amino acid position 710, or 733, respectively in an AAV2 or AAV8 capsid.

6. An isolated host cell comprising the polynucleotide vector system of claim 1.

7. The isolated host cell of claim 6, wherein the cell is a photoreceptor cell, a cone cell, a rod cell, a retinal cell, or any combination thereof.

* * * * *

UNITED STATES PATENT AND TRADEMARK OFFICE
CERTIFICATE OF CORRECTION

PATENT NO. : 10,214,572 B2
APPLICATION NO. : 14/279142
DATED : February 26, 2019
INVENTOR(S) : Boye et al.

It is certified that error appears in the above-identified patent and that said Letters Patent is hereby corrected as shown below:

In the Specification

At Column 1, Lines 19-22, the text:
This invention was made with government support under grant numbers EY00331 and EY021721 awarded by the National Institutes of Health. The government has certain rights in the invention.

Should be replaced with the text:
--This invention was made with government support under grant number EY021721 awarded by the National Institutes of Health. The government has certain rights in the invention.--

Signed and Sealed this
Fourteenth Day of May, 2019

Andrei Iancu
*Director of the United States Patent and Trademark Office*

```
                        SEQUENCE LISTING

<160> NUMBER OF SEQ ID NOS: 30

<210> SEQ ID NO 1
<211> LENGTH: 7847
<212> TYPE: DNA
<213> ORGANISM: Artificial sequence
<220> FEATURE:
<223> OTHER INFORMATION: the nucleotide of an "hMyo7a coding overlap
      vector A" of the subject invention
<220> FEATURE:
<221> NAME/KEY: exon
<222> LOCATION: (1164)..(1178)

<400> SEQUENCE: 1
cgccaggctg caggggggg gggggggggg ttggccactc cctctctgcg cgctcgctcg        60
ctcactgagg ccgggcgacc aaaggtcgcc cgacgcccgg gctttgcccg ggcggcctca       120
gtgagcgagc gagcgcgcag agagggagtg gccaactcca tcactagggg ttcctcagat       180
ctggcgcgcc caattcggta ccctagttat taatagtaat caattacggg gtcattagtt       240
catagcccat atatggagtt ccgcgttaca taacttacgg taaatggccc gcctggctga       300
ccgcccaacg accccgccc attgacgtca ataatgacgt atgttcccat agtaacgcca       360
atagggactt tccattgacg tcaatgggtg gactatttac ggtaaactgc ccacttggca       420
gtacatcaag tgtatcatat gccaagtacg cccctattg acgtcaatga cggtaaatgg       480
cccgcctggc attatgccca gtacatgacc ttatgggact ttcctacttg gcagtacatc      540
tacgtattag tcatcgctat taccatggtc gaggtgagcc ccacgttctg cttcactctc      600
cccatctccc cccctcccc accccaatt ttgtatttat ttattttta attattttgt        660 gcagcgatgg ggcggggg gggggggggg cgcgcgccag gcggggcggg gcggggcgag       720
gggcggggcg gggcgaggcg gagaggtgcg gcggcagcca atcagagcgg cgcgctccga       780
aagtttcctt ttatggcgag gcggcggcgg cggcggccct ataaaaagcg aagcgcgcgg       840
cgggcgggag tcgctgcgac gctgccttcg ccccgtgccc cgctccgccg ccgcctcgcg       900
ccgcccgccc cggctctgac tgaccgcgtt actcccacag gtgagcgggc gggacggccc       960
ttctcctccg ggctgtaatt agcgcttggt ttaatgacgg cttgtttctt ttctgtggct      1020
gcgtgaaagc cttgagggc tccgggagct agagcctctg ctaaccatgt tcatgccttc     1080 ttcttttcc tacagctcct gggcaacgtg ctggttattg tgctgtctca tcatttggc       1140 aaagaattct agcggccgcc acc atg gtg att ctt cag caggggacc                 1188
                           Met Val Ile Leu Gln
                             1               5 atgtgtggat ggacctgaga ttggggcagg agttcgacgt gcccatcggg gcggtggtga      1248
agctctgcga ctctgggcag gtccaggtgg tggatgatga agacaatgaa cactggatct      1308
```

```
ctccgcagaa cgcaacgcac atcaagccta tgcaccccac gtcggtccac ggcgtggagg    1368
acatgatccg cctggggac ctcaacgagg cgggcatctt gcgcaacctg cttatccgct     1428
accgggacca cctcatctac acgtatacgg gctccatcct ggtggctgtg aaccctacc     1488
agctgctctc catctactcg ccagagcaca tccgccagta taccaacaag aagattgggg    1548
agatgcccc ccacatcttt gccattgctg acaactgcta cttcaacatg aaacgcaaca     1608
gccgagacca gtgctgcatc atcagtgggg aatctgggc cgggaagacg gagagcacaa     1668
agctgatcct gcagttcctg gcagccatca gtgggcagca ctcgtggatt gagcagcagg    1728
tcttggaggc caccccatt ctggaagcat ttgggaatgc caagaccatc cgcaatgaca     1788
actcaagccg tttcggaaag tacatcgaca tccacttcaa caagcggggc gccatcgagg    1848
gcgcgaagat tgagcagtac ctgctggaaa agtcacgtgt ctgtcgccag gccctggatg    1908
aaaggaacta ccacgtgttc tactgcatgc tggagggtat gagtgaggat cagaagaaga    1968
agctgggctt gggccaggcc tctgactaca actacttggc catgggtaac tgcataacct    2028
gtgagggccg ggtggacagc caggagtacg ccaacatccg ctccgccatg aaggtgctca    2088
tgttcactga caccgagaac tgggagatct cgaagctcct ggctgccatc ctgcacctgg    2148
gcaacctgca gtatgaggca cgcacatttg aaaacctgga tgcctgtgag gttctcttct    2208
ccccatcgct ggccacagct gcatccctgc ttgaggtgaa ccccccagac ctgatgagct    2268
gcctgactag ccgcacccctc atcacccgcg gggagacggt gtccaccca ctgagcaggg     2328
aacaggcact ggacgtgcgc gacgccttcg taaagggat ctacgggcgg ctgttcgtgt     2388
ggattgtgga caagatcaac gcagcaattt acaagcctcc ctcccaggat gtgaagaact    2448
ctcgcaggtc catcggcctc ctggacatct ttgggtttga aactttgct gtgaacagct     2508
ttgagcagct ctgcatcaac ttcgccaatg agcacctgca gcagttcttt gtgcggcacg    2568
tgttcaagct ggagcaggag gaatatgacc tggagagcat tgactggctg cacatcgagt    2628
tcactgacaa ccaggatgcc ctggacatga ttgccaacaa gcccatgaac atcatctccc    2688
tcatcgatga ggagagcaag ttccccaagg gcacagacac caccatgtta cacaagctga    2748
actcccagca caagctcaac gccaactaca tcccccccaa gaacaaccat gagacccagt    2808
ttggcatcaa ccattttgca ggcatcgtct actatgagac ccaaggcttc ctggagaaga    2868
accgagacac cctgcatggg gacattatcc agctggtcca ctcctccagg aacaagttca    2928
tcaagcagat cttccaggcc gatgtcgcca tgggcgccga gaccaggaag cgctcgccca    2988
cacttagcag ccagttcaag cggtcactgg agctgctgat gcgcacgctg ggtgcctgcc    3048
agccccttctt tgtgcgatgc atcaagccca atgagttcaa gaagcccatg ctgttcgacc     3108
ggcacctgtg cgtgcgccag ctgcggtact caggaatgat ggagaccatc cgaatccgcc    3168
gagctggcta ccccatccgc tacagcttcg tagagtttgt ggagcggtac cgtgtgctgc    3228
tgccaggtgt gaagccggcc tacaagcagg gcgacctccg cgggacttgc agcgcatgg     3288
ctgaggctgt gctgggcacc cacgatgact ggcagatagg caaaaccaag atctttctga    3348
aggaccacca tgacatgctg ctggaagtgg agcgggacaa agccatcacc gacagagtca    3408
tcctccttca gaaagtcatc cggggattca agacaggtc taactttctg aagctgaaga     3468
acgctgccac actgatccag aggcactggc ggggtcacaa ctgtaggaag aactacgggc    3528
tgatgcgtct gggcttcctg cggctgcagg ccctgcaccg ctcccggaag ctgcaccagc    3588
agtaccgcct ggcccgccag cgcatcatcc agttccaggc ccgctgccgc gcctatctgg    3648
tgcgcaaggc cttccgccac cgcctctggg ctgtgctcac cgtgcaggcc tatgcccggg    3708
```

```
gcatgatcgc cgcaggctg caccaacgcc tcagggctga gtatctgtgg cgcctcgagg    3768
ctgagaaaat gcggctggcg gaggaagaga agcttcggaa ggagatgagc gccaagaagg    3828
ccaaggagga ggccgagcgc aagcatcagg agcgcctggc ccagctggct cgtgaggacg    3888
ctgagcggga gctgaaggag aaggaggccg ctcggcggaa aaggagctc ctggagcaga    3948 tggaaagggc ccgccatgag cctgtcaatc actcagacat ggtggacaag atgtttggct    4008
tcctggggac ttcaggtggc ctgccaggcc aggagggcca ggcacctagt ggctttgagg    4068
acctggagcg agggcggagg gagatggtgg aggaggacct ggatgcagcc ctgcccctgc    4128
ctgacgagga tgaggaggac ctctctgagt ataaatttgc caagttcgcg gccacctact    4188
tccaggggac aaccacgcac tcctacaccc ggcggccact caaacagcca ctgctctacc    4248
atgacgacga gggtgaccag ctggcagccc tggcggtctg gatcaccatc ctccgcttca    4308
tgggggacct ccctgagccc aagtaccaca cagccatgag tgatggcagt gagaagatcc    4368
ctgtgatgac caagatttat gagaccctgg gcaagaagac gtacaagagg gagctgcagg    4428
ccctgcaggg cgagggcgag gcccagctcc ccgagggcca gaagaagagc agtgtgaggc    4488
acaagctggt gcatttgact ctgaaaaaga agtccaagct cacagaggag gtgaccaaga    4548
ggctgcatga cggggagtcc acagtgcagg gcaacagcat gctggaggac cggcccacct    4608
ccaacctgga gaagctgcac ttcatcatcg gcaatgcat cctgcggcca gcactccggg    4668
acgagatcta ctgccagatc agcaagcagc tgacccacaa ccctccaag agcagctatg    4728 cccgggctg gattctcgtg tctctctgcg tgggctgttt cgcccctcc gagaagtttg    4788 tcaagtacct gcggaacttc gctagcgggc actagtccgt cgactgttaa ttaagcatgc    4848
tggggagaga tctaggaacc cctagtgatg gagttggcca ctccctctct gcgcgctcgc    4908
tcgctcactg aggccgcccg ggcaaagccc gggcgtcggg cgaccttggg tcgcccggcc    4968
tcagtgagcg agcgagcgcg cagagaggga gtggccaacc cccccccccc cccccctgca    5028
gccctgcatt aatgaatcgg ccaacgcgcg gggagaggcg gtttgcgtat tgggcgctct    5088
tccgcttcct cgctcactga ctcgctgcgc tcggtcgttc ggctgcggcg agcggtatca    5148
gctcactcaa aggcggtaat acggttatcc acagaatcag gggataacgc aggaaagaac    5208
atgtgagcaa aaggccagca aaaggccagg aaccgtaaaa aggccgcgtt gctggcgttt    5268
ttccataggc tccgcccccc tgacgagcat cacaaaaatc gacgctcaag tcagaggtgg    5328
cgaaacccga caggactata agataccagg cgtttcccc ctggaagctc cctcgtgcgc    5388
tctcctgttc cgaccctgcc gcttaccgga tacctgtccg cctttctccc ttcgggaagc    5448
gtggcgcttt ctcaatgctc acgctgtagg tatctcagtt cggtgtaggt cgttcgctcc    5508
aagctgggct gtgtgcacga accccccgtt cagcccgacc gctgcgcctt atccggtaac    5568
tatcgtcttg agtccaaccc ggtaagacac gacttatcgc cactggcagc agccactggt    5628
aacaggatta gcagagcgag gtatgtaggc ggtgctacag agttcttgaa gtggtggcct    5688
aactacggct acactagaag gacagtattt ggtatctgcg ctctgctgaa gccagttacc    5748
ttcggaaaaa gagttggtag ctcttgatcc ggcaaacaaa ccaccgctgg tagcggtggt    5808
ttttttgttt gcaagcagca gattacgcgc agaaaaaaag gatctcaaga agatcctttg    5868
atcttttcta cggggtctga cgctcagtgg aacgaaaact cacgttaagg gattttggtc    5928
atgagattat caaaaaggat cttcacctag atccttttaa attaaaaatg aagttttaaa    5988
tcaatctaaa gtatatatga gtaaacttgg tctgacagtt accaatgctt aatcagtgag    6048
```

-continued

| | | |
|---|---|---|
| gcacctatct cagcgatctg tctatttcgt tcatccatag ttgcctgact ccccgtcgtg | 6108 | |
| tagataacta cgatacggga gggcttacca tctggcccca gtgctgcaat gataccgcga | 6168 | |
| gacccacgct caccggctcc agatttatca gcaataaacc agccagccgg aagggccgag | 6228 | |
| cgcagaagtg gtcctgcaac tttatccgcc tccatccagt ctattaattg ttgccgggaa | 6288 | |
| gctagagtaa gtagttcgcc agttaatagt ttgcgcaacg ttgttgccat tgctacaggc | 6348 | |
| atcgtggtgt cacgctcgtc gtttggtatg gcttcattca gctccggttc caacgatca | 6408 | |
| aggcgagtta catgatcccc catgttgtgc aaaaaagcgg ttagctcctt cggtcctccg | 6468 | |
| atcgttgtca gaagtaagtt ggccgcagtg ttatcactca tggttatggc agcactgcat | 6528 | |
| aattctctta ctgtcatgcc atccgtaaga tgcttttctg tgactggtga gtactcaacc | 6588 | |
| aagtcattct gagaatagtg tatgcggcga ccgagttgct cttgcccggc gtcaatacgg | 6648 | |
| gataataccg cgccacatag cagaacttta aaagtgctca tcattggaaa acgttcttcg | 6708 | |
| gggcgaaaac tctcaaggat cttaccgctg ttgagatcca gttcgatgta acccactcgt | 6768 | |
| gcacccaact gatcttcagc atcttttact ttcaccagcg tttctgggtg agcaaaaaca | 6828 | |
| ggaaggcaaa atgccgcaaa aaagggaata agggcgacac ggaaatgttg aatactcata | 6888 | |
| ctcttccttt ttcaatatta ttgaagcatt tatcagggtt attgtctcat gagcggatac | 6948 | |
| atatttgaat gtatttagaa aaataaacaa ataggggttc cgcgcacatt tccccgaaaa | 7008 | |
| gtgccacctg acgtctaaga aaccattatt atcatgacat taacctataa aataggcgt | 7068 | |
| atcacgaggc cctttcgtct cgcgcgtttc ggtgatgacg gtgaaaacct ctgacacatg | 7128 | |
| cagctcccgg agacggtcac agcttgtctg taagcggatg ccgggagcag acaagcccgt | 7188 | |
| cagggcgcgt cagcgggtgt tggcgggtgt cggggctggc ttaactatgc ggcatcagag | 7248 | |
| cagattgtac tgagagtgca ccatatgcgg tgtgaaatac cgcacagatg cgtaaggaga | 7308 | |
| aaataccgca tcaggaaatt gtaaacgtta atattttgtt aaaattcgcg ttaaattttt | 7368 | |
| gttaaatcag ctcatttttt aaccaatagg ccgaaatcgg caaaatccct tataaatcaa | 7428 | |
| aagaatagac cgagataggg ttgagtgttg ttccagtttg gaacaagagt ccactattaa | 7488 | |
| agaacgtgga ctccaacgtc aaagggcgaa aaaccgtcta tcagggcgat ggcccactac | 7548 | |
| gtgaaccatc accctaatca agttttttgg ggtcgaggtg ccgtaaagca ctaaatcgga | 7608 | |
| accctaaagg gagcccccga tttagagctt gacggggaaa gccggcgaac gtggcgagaa | 7668 | |
| aggaagggaa gaaagcgaaa ggagcgggcg ctagggcgct ggcaagtgta gcggtcacgc | 7728 | |
| tgcgcgtaac caccacaccc gccgcgctta atgcgccgct acagggcgcg tcgcgccatt | 7788 | |
| cgccattcag gctacgcaac tgttgggaag ggcgatcggt gcgggcctct tcgctatta | 7847 | |

<210> SEQ ID NO 2
<211> LENGTH: 7779
<212> TYPE: DNA
<213> ORGANISM: Artificial sequence
<220> FEATURE:
<223> OTHER INFORMATION: the nucleotide of an "hMyo7a coding overlap
      vector B" of the subject invention

<400> SEQUENCE: 2

| | | |
|---|---|---|
| agggggggggg gggggggggt tggccactcc ctctctgcgc gctcgctcgc tcactgaggc | 60 | |
| cgggcgacca aagtcgcccg acgcccggg ctttgcccgg gcggcctcag tgagcgagcg | 120 | |
| agcgcgcaga gagggagtgg ccaactccat cactaggggt tcctcagatc tggcgcgccc | 180 | |
| aattggcttc gaattctagc ggccgctgct taagcaggtc taacttttctg aagctgaaga | 240 | |

-continued

```
acgctgccac actgatccag aggcactggc ggggtcacaa ctgtaggaag aactacgggc    300
tgatgcgtct gggcttcctg cggctgcagg ccctgcaccg ctcccggaag ctgcaccagc    360
agtaccgcct ggcccgccag cgcatcatcc agttccaggc ccgctgccgc gcctatctgg    420
tgcgcaaggc cttccgccac cgcctctggg ctgtgctcac cgtgcaggcc tatgcccggg    480
gcatgatcgc ccgcaggctg caccaacgcc tcagggctga gtatctgtgg cgcctcgagg    540
ctgagaaaat gcggctggcg gaggaagaga agcttcggaa ggagatgagc gccaagaagg    600
ccaaggagga ggccgagcgc aagcatcagg agcgcctggc ccagctggct cgtgaggacg    660
ctgagcggga gctgaaggag aaggaggccg ctcggcggaa aaggagctc ctggagcaga    720 tggaaagggc ccgccatgag cctgtcaatc actcagacat ggtggacaag atgtttggct    780
tcctggggac ttcaggtggc ctgccaggcc aggagggcca ggcacctagt ggctttgagg    840
acctggagcg agggcggagg gagatggtgg aggaggacct ggatgcagcc ctgcccctgc    900
ctgacgagga tgaggaggac ctctctgagt ataaatttgc caagttcgcg gccacctact    960 tccagggac aaccacgcac tcctacaccc ggcggccact caaacagcca ctgctctacc   1020
atgacgacga gggtgaccag ctggcagccc tggcggtctg gatcaccatc ctccgcttca   1080
tgggggacct ccctgagccc aagtaccaca cagccatgag tgatggcagt gagaagatcc   1140
ctgtgatgac caagatttat gagaccctgg gcaagaagac gtacaagagg gagctgcagg   1200
ccctgcaggg cgagggcgag gcccagctcc ccgagggcca agaagagc agtgtgaggc   1260 acaagctggt gcatttgact ctgaaaaaga agtccaagct cacagaggag gtgaccaaga   1320
ggctgcatga cggggagtcc acagtgcagg gcaacagcat gctggaggac cggcccacct   1380
ccaacctgga gaagctgcac ttcatcatcg gcaatggcat cctgcggcca gcactccggg   1440
acgagatcta ctgccagatc agcaagcagc tgacccacaa cccctccaag agcagctatg   1500 cccgggggctg gattctcgtg tctctctgcg tgggctgttt cgccccctcc gagaagtttg   1560
tcaagtacct gcggaacttc atccacgggg gcccgcccgg ctacgccccg tactgtgagg   1620
agcgcctgag aaggaccttt gtcaatggga cacggacaca gccgcccagc tggctggagc   1680
tgcaggccac caagtccaag aagccaatca tgttgcccgt gacattcatg gatgggacca   1740
ccaagaccct gctgacggac tcggcaacca cggccaagga gctctgcaac gcgctggccg   1800
acaagatctc tctcaaggac cggttcgggt tctccctcta cattgccctg tttgacaagg   1860
tgtcctccct gggcagcggc agtgaccacg tcatggacgc catctcccag tgcgagcagt   1920
acgccaagga gcagggcgcc caggagcgca acgcccctg gaggctcttc ttccgcaaag   1980
aggtcttcac gccctggcac agcccctccg aggacaacgt ggccaccaac ctcatctacc   2040
agcaggtggt gcgaggagtc aagtttgggg agtacaggtg tgagaaggag gacgacctgg   2100
ctgagctggc ctcccagcag tactttgtag actatggctc tgagatgatc ctggagcgcc   2160
tcctgaacct cgtgcccacc tacatccccg accgcgagat cacgcccctg aagacgctgg   2220
agaagtgggc ccagctggcc atcgccgccc acaagaaggg gatttatgcc cagagagaa   2280 ctgatgccca gaaggtcaaa gaggatgtgg tcagttatgc ccgcttcaag tggcccttgc   2340
tcttctccag gttttatgaa gcctacaaat tctcaggccc cagtctcccc aagaacgacg   2400
tcatcgtggc cgtcaactgg acgggtgtgt actttgtgga tgagcaggag caggtacttc   2460
tggagctgtc cttcccagag atcatggccg tgtccagcag caggggagcg aaaacgacgg   2520
cccccagctt cacgctggcc accatcaagg gggacgaata caccttcacc tccagcaatg   2580
ctgaggacat tcgtgacctg gtggtcacct tcctagaggg gctccggaag agatctaagt   2640
```

```
atgttgtggc cctgcaggat aaccccaacc ccgcaggcga ggagtcaggc ttcctcagct    2700
ttgccaaggg agacctcatc atcctggacc atgacacggg cgagcaggtc atgaactcgg    2760
gctgggccaa cggcatcaat gagaggacca agcagcgtgg ggacttcccc accgacagtg    2820
tgtacgtcat gcccactgtc accatgccac cgcgggagat tgtggccctg gtcaccatga    2880
ctcccgatca gaggcaggac gttgtccggc tcttgcagct gcgaacggcg gagcccgagg    2940
tgcgtgccaa gccctacacg ctggaggagt tttcctatga ctacttcagg cccccaccca    3000
agcacacgct gagccgtgtc atggtgtcca aggcccgagg caaggaccgg ctgtggagcc    3060
acacgcggga accgctcaag caggcgctgc tcaagaagct cctgggcagt gaggagctct    3120
cgcaggaggc ctgcctggcc ttcattgctg tgctcaagta catgggcgac tacccgtcca    3180
agaggacacg ctccgtcaac gagctcaccg accagatctt tgagggtccc ctgaaagccg    3240
agcccctgaa ggacgaggca tatgtgcaga tcctgaagca gctgaccgac aaccacatca    3300
ggtacagcga ggagcggggt tgggagctgc tctggctgtg cacgggcctt ttcccaccca    3360
gcaacatcct cctgccccac gtgcagcgct tcctgcagtc ccgaaagcac tgcccactcg    3420
ccatcgactg cctgcaacgg ctccagaaag ccctgagaaa cgggtcccgg aagtaccctc    3480
cgcacctggt ggaggtggag gccatccagc acaagaccac ccagattttc cacaaagtct    3540
acttccctga tgacactgac gaggccttcg aagtggagtc cagcaccaag gccaaggact    3600
tctgccagaa catcgccacc aggctgctcc tcaagtcctc agagggattc agcctctttg    3660
tcaaaattgc agacaaggtc atcagcgttc tgagaatga cttcttcttt gactttgttc    3720
gacacttgac agactggata agaaagctc ggcccatcaa ggacggaatt gtgccctcac    3780
tcacctacca ggtgttcttc atgaagaagc tgtggaccac cacggtgcca gggaaggatc    3840
ccatggccga ttccatcttc cactattacc aggagttgcc caagtatctc cgaggctacc    3900
acaagtgcac gcgggaggag gtgctgcagc tgggggcgct gatctacagg gtcaagttcg    3960
aggaggacaa gtcctacttc cccagcatcc ccaagctgct gcgggagctg gtgccccagg    4020
accttatccg gcaggtctca cctgatgact ggaagcggtc catcgtcgcc tacttcaaca    4080
agcacgcagg gaagtccaag gaggaggcca agctggcctt cctgaagctc atcttcaagt    4140
ggcccacctt tggctcagcc ttcttcgagg tgaagcaaac tacggagcca aacttccctg    4200
agatcctcct aattgccatc aacaagtatg gggtcagcct catcgatccc aaaacgaagg    4260
atatcctcac cactcatccc ttcaccaaga tctccaactg gagcagcggc aacacctact    4320
tccacatcac cattgggaac ttggtgcgcg ggagcaaact gctctgcgag acgtcactgg    4380
gctacaagat ggatgacctc ctgacttcct acattagcca gatgctcaca gccatgagca    4440
aacagcgggc tccaggagc ggcaagtgag gtaccaaggg cgaattctgc agtcgactag    4500
agctcgctga tcagcctcga ctgtgccttc tagttgccag ccatctgttg tttgcccctc    4560
ccccgtgcct tccttgaccc tggaaggtgc cactcccact gtcctttcct aataaaatga    4620
ggaaattgca tcgcattgtc tgagtaggtg tcattctatt ctggggggtg gggtggggca    4680
ggacagcaag ggggaggatt gggaagacaa tagcaggcat gctggggaga gatctgagga    4740
ctagtccgtc gactgttaat taagcatgct ggggagagat ctaggaaccc ctagtgatgg    4800
agttggccac tccctctctg cgcgctcgct cgctcactga ggccgcccgg gcaaagcccg    4860
ggcgtcgggc gacctttggt cgcccggcct cagtgagcga gcgagcgcgc agagagggag    4920
tggccaaccc cccccccccc cccctgcag ccctgcatta atgaatcggc caacgcgcgg    4980
```

```
ggagaggcgg tttgcgtatt gggcgctctt ccgcttcctc gctcactgac tcgctgcgct    5040
cggtcgttcg gctgcggcga gcggtatcag ctcactcaaa ggcggtaata cggttatcca    5100
cagaatcagg ggataacgca ggaaagaaca tgtgagcaaa aggccagcaa aaggccagga    5160
accgtaaaaa ggccgcgttg ctggcgtttt tccataggct ccgcccccct gacgagcatc    5220
acaaaaatcg acgctcaagt cagaggtggc gaaacccgac aggactataa agataccagg    5280
cgtttccccc tggaagctcc ctcgtgcgct ctcctgttcc gaccctgccg cttaccggat    5340
acctgtccgc ctttctccct tcgggaagcg tggcgctttc tcaatgctca cgctgtaggt    5400
atctcagttc ggtgtaggtc gttcgctcca agctgggctg tgtgcacgaa ccccccgttc    5460
agcccgaccg ctgcgcctta tccggtaact atcgtcttga gtccaacccg gtaagacacg    5520
acttatcgcc actggcagca gccactggta acaggattag cagagcgagg tatgtaggcg    5580
gtgctacaga gttcttgaag tggtggccta actacggcta cactagaagg acagtatttg    5640
gtatctgcgc tctgctgaag ccagttacct tcggaaaaag agttggtagc tcttgatccg    5700
gcaaacaaac caccgctggt agcggtggtt tttttgtttg caagcagcag attacgcgca    5760
gaaaaaaagg atctcaagaa gatcctttga tcttttctac ggggtctgac gctcagtgga    5820
acgaaaactc acgttaaggg attttggtca tgagattatc aaaaaggatc ttcacctaga    5880
tccttttaaa ttaaaaatga agttttaaat caatctaaag tatatatgag taaacttggt    5940
ctgacagtta ccaatgctta atcagtgagg cacctatctc agcgatctgt ctatttcgtt    6000
catccatagt tgcctgactc cccgtcgtgt agataactac gatacgggag ggcttaccat    6060
ctggccccag tgctgcaatg ataccgcgag acccacgctc accggctcca gatttatcag    6120
caataaacca gccagccgga agggccgagc gcagaagtgg tcctgcaact ttatccgcct    6180
ccatccagtc tattaattgt tgccgggaag ctagagtaag tagttcgcca gttaatagtt    6240
tgcgcaacgt tgttgccatt gctacaggca tcgtggtgtc acgctcgtcg tttggtatgg    6300
cttcattcag ctccggttcc caacgatcaa ggcgagttac atgatccccc atgttgtgca    6360
aaaaagcggt tagctccttc ggtcctccga tcgttgtcag aagtaagttg gccgcagtgt    6420
tatcactcat ggttatggca gcactgcata attctcttac tgtcatgcca tccgtaagat    6480
gcttttctgt gactggtgag tactcaacca agtcattctg agaatagtgt atgcggcgac    6540
cgagttgctc ttgcccggcg tcaatacggg ataataccgc gccacatagc agaactttaa    6600
aagtgctcat cattggaaaa cgttcttcgg ggcgaaaact ctcaaggatc ttaccgctgt    6660
tgagatccag ttcgatgtaa cccactcgtg cacccaactg atcttcagca tcttttactt    6720
tcaccagcgt ttctgggtga gcaaaaacag gaaggcaaaa tgccgcaaaa aagggaataa    6780
gggcgacacg gaaatgttga atactcatac tcttcctttt tcaatattat tgaagcattt    6840
atcagggtta ttgtctcatg agcggataca tatttgaatg tatttagaaa aataaacaaa    6900
taggggttcc gcgcacattt ccccgaaaag tgccacctga cgtctaagaa accattatta    6960
tcatgacatt aacctataaa aataggcgta tcacgaggcc ctttcgtctc gcgcgtttcg    7020
gtgatgacgg tgaaaacctc tgacacatgc agctcccgga gacggtcaca gcttgtctgt    7080
aagcggatgc cgggagcaga caagcccgtc agggcgcgtc agcgggtgtt ggcgggtgtc    7140
ggggctggct taactatgcg gcatcagagc agattgtact gagagtgcac catatgcggt    7200
gtgaaatacc gcacagatgc gtaaggagaa aataccgcat caggaaattg taaacgttaa    7260
tattttgtta aaattcgcgt taaatttttg ttaaatcagc tcattttttta accaataggc    7320 cgaaatcggc aaaatccctt ataaatcaaa agaatagacc gagataggt tgagtgttgt    7380
```

| | |
|---|---|
| tccagtttgg aacaagagtc cactattaaa gaacgtggac tccaacgtca aagggcgaaa | 7440 |
| aaccgtctat cagggcgatg gcccactacg tgaaccatca ccctaatcaa gttttttggg | 7500 |
| gtcgaggtgc cgtaaagcac taaatcggaa ccctaaaggg agcccccgat ttagagcttg | 7560 |
| acggggaaag ccggcgaacg tggcgagaaa ggaagggaag aaagcgaaag gagcgggcgc | 7620 |
| tagggcgctg gcaagtgtag cggtcacgct gcgcgtaacc accacacccg ccgcgcttaa | 7680 |
| tgcgccgcta cagggcgcgt cgcgccattc gccattcagg ctacgcaact gttgggaagg | 7740 |
| gcgatcggtg cgggcctctt cgctattacg ccaggctgc | 7779 |

<210> SEQ ID NO 3
<211> LENGTH: 7405
<212> TYPE: DNA
<213> ORGANISM: Artificial sequence
<220> FEATURE:
<223> OTHER INFORMATION: the nucleotide of an "hMyo7a intron 23 splicing vector A" of the subject invention
<220> FEATURE:
<221> NAME/KEY: exon
<222> LOCATION: (1153)..(1167)

<400> SEQUENCE: 3

| | |
|---|---|
| agggggggggg ggggggggggt tggccactcc ctctctgcgc gctcgctcgc tcactgaggc | 60 |
| cgggcgacca aggtcgccc gacgcccggg ctttgcccgg gcggcctcag tgagcgagcg | 120 |
| agcgcgcaga gagggagtgg ccaactccat cactaggggt tcctcagatc tggcgcgccc | 180 |
| aattcggtac cctagttatt aatagtaatc aattacgggg tcattagttc atagcccata | 240 |
| tatggagttc cgcgttacat aacttacggt aaatggcccg cctggctgac cgcccaacga | 300 |
| ccccccgccca ttgacgtcaa taatgacgta tgttcccata gtaacgccaa tagggacttt | 360 |
| ccattgacgt caatgggtgg actatttacg gtaaactgcc cacttggcag tacatcaagt | 420 |
| gtatcatatg ccaagtacgc cccctattga cgtcaatgac ggtaaatggc ccgcctggca | 480 |
| ttatgcccag tacatgacct tatgggactt tcctacttgg cagtacatct acgtattagt | 540 |
| catcgctatt accatggtcg aggtgagccc cacgttctgc ttcactctcc ccatctcccc | 600 |
| cccctcccca ccccccaattt tgtatttatt tattttttaa ttattttgtg cagcgatggg | 660 |
| ggcgggggggg ggggggggggc gcgcgccagg cggggcgggg cggggcgagg ggcggggcgg | 720 |
| ggcgaggcgg agaggtgcgg cggcagccaa tcagagcggc gcgctccgaa agtttccttt | 780 |
| tatggcgagg cggcggcggc ggcggcccta taaaaagcga agcgcgcggc gggcgggagt | 840 |
| cgctgcgacg ctgccttcgc cccgtgcccc gctccgccgc cgcctcgcgc cgcccgcccc | 900 |
| ggctctgact gaccgcgtta ctcccacagg tgagcgggcg ggacggccct tctcctccgg | 960 |
| gctgtaatta gcgcttggtt taatgacggc ttgtttcttt tctgtggctg cgtgaaagcc | 1020 |
| ttgaggggct ccgggagcta gagcctctgc taaccatgtt catgccttct tctttttcct | 1080 |
| acagctcctg ggcaacgtgc tggttattgt gctgtctcat catttttggca aagaattcta | 1140 |
| gcggccgcca cc atg gtg att ctt cag caggggggacc atgtgtggat | 1187 |
|           Met Val Ile Leu Gln | |
|            1           5 | |
| ggacctgaga ttggggcagg agttcgacgt gcccatcggg gcggtggtga agctctgcga | 1247 |
| ctctgggcag gtccaggtgg tggatgatga agacaatgaa cactggatct ctccgcagaa | 1307 |
| cgcaacgcac atcaagccta tgcacccac gtcggtccac ggcgtggagg acatgatccg | 1367 |
| cctgggggac ctcaacgagg cggccatctt gcgcaacctg cttatccgct accgggacca | 1427 |

```
cctcatctac acgtatacgg gctccatcct ggtggctgtg aaccccctacc agctgctctc     1487
catctactcg ccagagcaca tccgccagta taccaacaag aagattgggg agatgccccc     1547
ccacatcttt gccattgctg acaactgcta cttcaacatg aaacgcaaca gccgagacca     1607
gtgctgcatc atcagtgggg aatctggggc cgggaagacg gagagcacaa agctgatcct     1667
gcagttcctg gcagccatca gtgggcagca ctcgtggatt gagcagcagg tcttggaggc     1727
caccccatt ctggaagcat ttgggaatgc caagaccatc cgcaatgaca actcaagccg      1787
tttcggaaag tacatcgaca tccacttcaa caagcggggc gccatcgagg gcgcgaagat     1847
tgagcagtac ctgctggaaa agtcacgtgt ctgtcgccag gccctggatg aaaggaacta     1907
ccacgtgttc tactgcatgc tggagggtat gagtgaggat cagaagaaga agctgggctt     1967
gggccaggcc tctgactaca actacttggc catgggtaac tgcataaccct gtgagggccg     2027
ggtggacagc caggagtacg ccaacatccg ctccgccatg aaggtgctca tgttcactga     2087
caccgagaac tgggagatct cgaagctcct ggctgccatc ctgcacctgg gcaacctgca     2147
gtatgaggca cgcacatttg aaaacctgga tgcctgtgag gttctcttct ccccatcgct     2207
ggccacagct gcatccctgc ttgaggtgaa cccccccagac ctgatgagct gcctgactag     2267
ccgcacccctc atcacccgcg gggagacggt gtccaccccca ctgagcaggg aacaggcact     2327
ggacgtgcgc gacgccttcg taaaggggat ctacgggcgg ctgttcgtgt ggattgtgga     2387
caagatcaac gcagcaattt acaagcctcc ctcccaggat gtgaagaact ctcgcaggtc     2447
catcggcctc ctggacatct ttgggtttga aactttgct gtgaacagct ttgagcagct      2507
ctgcatcaac ttcgccaatg agcacctgca gcagttcttt gtgcggcacg tgttcaagct     2567
ggagcaggag gaatatgacc tggagagcat tgactggctg cacatcgagt tcactgacaa     2627
ccaggatgcc ctggacatga ttgccaacaa gcccatgaac atcatctccc tcatcgatga     2687
ggagagcaag ttccccaagg gcacagacac caccatgtta cacaagctga actcccagca     2747
caagctcaac gccaactaca tcccccccaa gaacaaccat gagacccagt ttggcatcaa     2807
ccattttgca ggcatcgtct actatgagac ccaaggcttc ctggagaaga accgagacac     2867
cctgcatggg gacattatcc agctggtcca ctcctccagg aacaagttca tcaagcagat     2927
cttccaggcc gatgtcgcca tgggcgccga gaccaggaag cgctcgccca cacttagcag     2987
ccagttcaag cggtcactgg agctgctgat gcgcacgctg ggtgcctgcc agcccttctt     3047
tgtgcgatgc atcaagccca tgagttcaa gaagcccatg ctgttcgacc ggcacctgtg      3107
cgtgcgccag ctgcgggtact caggaatgat ggagaccatc cgaatccgcc gagctggcta     3167
ccccatccgc tacagcttcg tagagtttgt ggagcggtac cgtgtgctgc tgccaggtgt     3227
gaagccggcc tacaagcagg cgacctccg cgggacttgc cagcgcatgg ctgaggctgt      3287
gctgggcacc cacgatgact ggcagatagg caaaaccaag atctttctga aggaccacca     3347
tgacatgctg ctggaagtgg agcgggacaa agccatcacc gacagagtca tcctccttca     3407
gaaagtcatc cggggattca agacaggtc taactttctg aagctgaaga acgctgccac      3467
actgatccag aggcactggc ggggtcacaa ctgtaggaag aactacgggc tgatgcgtct     3527
gggcttcctg cggctgcagg ccctgcaccg ctcccggaag ctgcaccagc agtaccgcct     3587
ggcccgccag cgcatcatcc agttccaggc ccgctgccgc gcctatctgg tgcgcaaggc     3647
cttccgccac cgcctctggg ctgtgctcac cgtgcaggcc tatgcccggg gcatgatcgc     3707
ccgcaggctg caccaacgcc tcagggctga gtatctgtgg cgcctcgagg ctgagaaaat     3767
gcggctggcg gaggaagaga agcttcggaa ggagatgagc gccaagaagg ccaaggagga     3827
```

```
ggccgagcgc aagcatcagg agcgcctggc ccagctggct cgtgaggacg ctgagcggga    3887
gctgaaggag aaggaggccg ctcggcggaa gaaggagctc ctggagcaga tggaaagggc    3947
ccgccatgag cctgtcaatc actcagacat ggtggacaag atgtttggct tcctggggac    4007
ttcaggtggc ctgccaggcc aggagggcca ggcacctagt ggctttgagg taccaggcta    4067
gggacagggg ctccagaggc ccacacacac cgcttgtgtt gatcctccct ccttctgtgc    4127
ccttggcctt aaagcccacc cagtccctct gaacagtggg gagcagagat gaactgggtc    4187
cgggctgcag gtcccaggtc ctgtccctct ccaacgccct tctcaagttt tttttttgt    4247 ttttttttt ttttttttt ttgagatggg gtcgtaccct gttgctcagg ctggagtgca    4307
gtagcgtgat cacagctcac tgcagccttg aacttctggg ctcaggcggc tagcgggcac    4367
tagtccgtcg actgttaatt aagcatgctg gggagagatc taggaacccc tagtgatgga    4427
gttggccact ccctctctgc gcgctcgctc gctcactgag gccgcccggg caaagcccgg    4487
gcgtcgggcg acctttggtc gcccggcctc agtgagcgag cgagcgcgca gagagggagt    4547
ggccaacccc cccccccccc cccctgcagc cctgcattaa tgaatcggcc aacgcgcggg    4607
gagaggcggt ttgcgtattg ggcgctcttc cgcttcctcg ctcactgact cgctgcgctc    4667
ggtcgttcgg ctgcggcgag cggtatcagc tcactcaaag gcggtaatac ggttatccac    4727
agaatcaggg gataacgcag gaaagaacat gtgagcaaaa ggccagcaaa aggccaggaa    4787
ccgtaaaaag gccgcgttgc tggcgttttt ccataggctc cgcccccctg acgagcatca    4847
caaaaatcga cgctcaagtc agaggtggcg aaacccgaca ggactataaa gataccaggc    4907
gtttccccct ggaagctccc tcgtgcgctc tcctgttccg accctgccgc ttaccggata    4967
cctgtccgcc tttctccctt cgggaagcgt ggcgctttct caatgctcac gctgtaggta    5027
tctcagttcg gtgtaggtcg ttcgctccaa gctgggctgt gtgcacgaac cccccgttca    5087
gcccgaccgc tgcgccttat ccggtaacta tcgtcttgag tccaacccgg taagacacga    5147
cttatcgcca ctggcagcag ccactggtaa caggattagc agagcgaggt atgtaggcgg    5207
tgctacagag ttcttgaagt ggtggcctaa ctacggctac actagaagga cagtatttgg    5267
tatctgcgct ctgctgaagc cagttacctt cggaaaaaga gttggtagct cttgatccgg    5327
caaacaaacc accgctggta gcggtggttt ttttgtttgc aagcagcaga ttacgcgcag    5387
aaaaaaagga tctcaagaag atcctttgat cttttctacg gggtctgacg ctcagtggaa    5447
cgaaaactca cgttaaggga ttttggtcat gagattatca aaaaggatct tcacctagat    5507
ccttttaaat taaaaatgaa gttttaaatc aatctaaagt atatatgagt aaacttggtc    5567
tgacagttac caatgcttaa tcagtgaggc acctatctca gcgatctgtc tatttcgttc    5627
atccatagtt gcctgactcc ccgtcgtgta gataactacg atacgggagg gcttaccatc    5687
tggccccagt gctgcaatga taccgcgaga cccacgctca ccggctccag atttatcagc    5747
aataaaccag ccagccggaa gggccgagcg cagaagtggt cctgcaactt tatccgcctc    5807
catccagtct attaattgtt gccgggaagc tagagtaagt agttcgccag ttaatagttt    5867
gcgcaacgtt gttgccattg ctacaggcat cgtggtgtca cgctcgtcgt ttggtatggc    5927
ttcattcagc tccggttccc aacgatcaag gcgagttaca tgatccccca tgttgtgcaa    5987
aaaagcggtt agctccttcg gtcctccgat cgttgtcaga agtaagttgg ccgcagtgtt    6047
atcactcatg gttatggcag cactgcataa ttctcttact gtcatgccat ccgtaagatg    6107
cttttctgtg actggtgagt actcaaccaa gtcattctga gaatagtgta tgcggcgacc    6167
```

```
gagttgctct tgcccggcgt caatacggga taataccgcg ccacatagca gaactttaaa      6227
agtgctcatc attggaaaac gttcttcggg gcgaaaactc tcaaggatct taccgctgtt      6287
gagatccagt tcgatgtaac ccactcgtgc acccaactga tcttcagcat cttttacttt      6347
caccagcgtt tctgggtgag caaaaacagg aaggcaaaat gccgcaaaaa agggaataag      6407
ggcgacacgg aaatgttgaa tactcatact cttcctttttt caatattatt gaagcattta      6467
tcagggttat tgtctcatga gcggatacat atttgaatgt atttagaaaa ataaacaaat      6527
aggggttccg cgcacatttc cccgaaaagt gccacctgac gtctaagaaa ccattattat      6587
catgacatta acctataaaa ataggcgtat cacgaggccc tttcgtctcg cgcgtttcgg      6647
tgatgacggt gaaaacctct gacacatgca gctcccggag acggtcacag cttgtctgta      6707
agcggatgcc gggagcagac aagcccgtca gggcgcgtca gcgggtgttg gcgggtgtcg      6767
gggctggctt aactatgcgg catcagagca gattgtactg agagtgcacc atatgcggtg      6827
tgaaataccg cacagatgcg taaggagaaa ataccgcatc aggaaattgt aaacgttaat      6887
attttgttaa aattcgcgtt aaattttttgt taaatcagct cattttttaa ccaataggcc      6947
gaaatcggca aaatccctta taatcaaaa gaatagaccg atagggtt gagtgttgtt       7007 ccagtttgga acaagagtcc actattaaag aacgtggact ccaacgtcaa agggcgaaaa      7067
accgtctatc agggcgatgg cccactacgt gaaccatcac cctaatcaag ttttttgggg      7127
tcgaggtgcc gtaaagcact aaatcggaac cctaaaggga gcccccgatt tagagcttga      7187
cggggaaagc cggcgaacgt ggcgagaaag gaagggaaga agcgaaagg agcgggcgct      7247 agggcgctgg caagtgtagc ggtcacgctg cgcgtaacca ccacacccgc cgcgcttaat      7307
gcgccgctac agggcgcgtc gcgccattcg ccattcaggc tacgcaactg ttgggaaggg      7367
cgatcggtgc gggcctcttc gctattacgc caggctgc                            7405
```

<210> SEQ ID NO 4
<211> LENGTH: 7477
<212> TYPE: DNA
<213> ORGANISM: Artificial sequence
<220> FEATURE:
<223> OTHER INFORMATION: the nucleotide of an "hMyo7a intron 23 splicing vector B" of the subject invention

<400> SEQUENCE: 4

```
cgccaggctg caggggggggg ggggggggggg ttggccactc cctctctgcg cgctcgctcg        60
ctcactgagg ccgggcgacc aaaggtcgcc cgacgcccgg gctttgcccg gcggcctca         120 gtgagcgagc gagcgcgcag agagggagtg gccaactcca tcactagggg ttcctcagat        180
ctggcgcgcc caattggctt cgaattctag cggccgctgc ttaagcaccg cttgtgttga        240 tcctcccctcc ttctgtgccc ttggccttaa agcccaccca gtccctctga acagtgggga        300
gcagagatga actgggtccg ggctgcaggt cccaggtcct gtccctctcc aacgcccttc        360
tcaagttttt ttttttgttt tttttttttt tttttttttt gagatggggt cgtaccctgt        420
tgctcaggct ggagtgcagt agcgtgatca cagctcactg cagccttgaa cttctgggct        480
caggcgatcc tcccacctga gcttcctgag tagctgggac tccagggcat acctcttgtc        540
tccttcagga cctggagcga gggcggaggg agatggtgga ggaggacctg gatgcagccc        600 tgccccctgcc tgacgaggat gaggaggacc tctctgagta taaatttgcc aagttcgcgg        660
ccacctactt ccaggggaca accacgcact cctacccccg gcggcactc aaacagccac         720 tgctctacca tgacgacgag ggtgaccagc tggcagccct ggcggtctgg atcaccatcc        780
```

```
tccgcttcat gggggacctc cctgagccca agtaccacac agccatgagt gatggcagtg    840
agaagatccc tgtgatgacc aagatttatg agaccctggg caagaagacg tacaagaggg    900
agctgcaggc cctgcagggc gagggcgagg cccagctccc cgagggccag aagaagagca    960
gtgtgaggca aagctggtg catttgactc tgaaaaagaa gtccaagctc acagaggagg    1020
tgaccaagag gctgcatgac ggggagtcca cagtgcaggg caacagcatg ctggaggacc    1080
ggcccacctc caacctggag aagctgcact tcatcatcgg caatggcatc ctgcggccag    1140
cactccggga cgagatctac tgccagatca gcaagcagct gacccacaac ccctccaaga    1200
gcagctatgc ccggggctgg attctcgtgt ctctctgcgt gggctgtttc gcccctccg     1260
agaagtttgt caagtacctg cggaacttca tccacggggg cccgcccggc tacgcccgt     1320
actgtgagga gcgcctgaga aggacctttg tcaatgggac acggacacag ccgcccagct    1380
ggctggagct gcaggccacc aagtccaaga agccaatcat gttgcccgtg acattcatgg    1440
atgggaccac caagaccctg ctgacggact cggcaaccac ggccaaggag ctctgcaacg    1500
cgctggccga caagatctct ctcaaggacc ggttcgggtt ctccctctac attgccctgt    1560
ttgacaaggt gtcctccctg ggcagcggca gtgaccacgt catggacgcc atctcccagt    1620
gcgagcagta cgccaaggag cagggcgccc aggagcgcaa cgcccctgg aggctcttct     1680
tccgcaaaga ggtcttcacg ccctggcaca gcccctccga ggacaacgtg gccaccaacc    1740
tcatctacca gcaggtggtg cgaggagtca agtttgggga gtacaggtgt gagaaggagg    1800
acgacctggc tgagctggcc tcccagcagt actttgtaga ctatggctct gagatgatcc    1860
tggagcgcct cctgaacctc gtgcccacct acatccccga ccgcgagatc acgcccctga    1920
agacgctgga gaagtgggcc cagctggcca tcgccgccca caagaagggg atttatgccc    1980
agaggagaac tgatgcccag aaggtcaaag aggatgtggt cagttatgcc cgcttcaagt    2040
ggccttgct cttctccagg tttatgaag cctacaaatt ctcaggcccc agtctcccca     2100
agaacgacgt catcgtggcc gtcaactgga cgggtgtgta ctttgtggat gagcaggagc    2160
aggtacttct ggagctgtcc ttcccagaga tcatggccgt gtccagcagc aggggagcga    2220
aaacgacggc cccagcttc acgctggcca ccatcaaggg ggacgaatac accttcacct     2280
ccagcaatgc tgaggacatt cgtgacctgg tggtcacctt cctagagggg ctccggaaga    2340
gatctaagta tgttgtggcc ctgcaggata accccaaccc cgcaggcgag gagtcaggct    2400
tcctcagctt tgccaaggga gacctcatca tcctggacca tgacacgggc gagcaggtca    2460
tgaactcggg ctgggccaac ggcatcaatg agaggaccaa gcagcgtggg gacttcccca    2520
ccgacagtgt gtacgtcatg cccactgtca ccatgccacc gcgggagatt gtggccctgg    2580
tcaccatgac tcccgatcag aggcaggacg ttgtccggct cttgcagctg cgaacgcgg     2640
agcccgaggt gcgtgccaag ccctacacgc tggaggagtt ttcctatgac tacttcaggc    2700
ccccaccccaa gcacacgctg agccgtgtca tggtgtccaa ggcccgaggc aaggaccggc    2760
tgtggagcca cacgcgggaa ccgctcaagc aggcgctgct caagaagctc ctgggcagtg    2820
aggagctctc gcaggaggcc tgcctggcct tcattgctgt gctcaagtac atgggcgact    2880
acccgtccaa gaggacacgc tccgtcaacg agctcaccga ccagatcttt gagggtcccc    2940
tgaaagccga gcccctgaag gacgaggcat atgtgcagat cctgaagcag ctgaccgaca    3000
accacatcag gtacagcgag gagcggggtt gggagctgct ctggctgtgc acgggccttt    3060
tcccacccaa caacatcctc ctgccccacg tgcagcgctt cctgcagtcc cgaaagcact    3120
gcccactcgc catcgactgc ctgcaacggc tccagaaagc cctgagaaac gggtcccgga    3180
```

```
agtaccctcc gcacctggtg gaggtggagg ccatccagca caagaccacc cagattttcc    3240
acaaagtcta cttccctgat gacactgacg aggccttcga agtggagtcc agcaccaagg    3300
ccaaggactt ctgccagaac atcgccacca ggctgctcct caagtcctca gagggattca    3360
gcctctttgt caaaattgca gacaaggtca tcagcgttcc tgagaatgac ttcttctttg    3420
actttgttcg acacttgaca gactggataa agaaagctcg gcccatcaag gacggaattg    3480
tgccctcact cacctaccag gtgttcttca tgaagaagct gtggaccacc acggtgccag    3540
ggaaggatcc catggccgat tccatcttcc actattacca ggagttgccc aagtatctcc    3600
gaggctacca caagtgcacg cgggaggagg tgctgcagct gggggcgctg atctacaggg    3660
tcaagttcga ggaggacaag tcctacttcc ccagcatccc caagctgctg cgggagctgg    3720
tgccccagga ccttatccgg caggtctcac ctgatgactg gaagcggtcc atcgtcgcct    3780
acttcaacaa gcacgcaggg aagtccaagg aggaggccaa gctggccttc ctgaagctca    3840
tcttcaagtg gccccacctt tggctcagcct tcttcgaggt gaagcaaact acggagccaa    3900
acttccctga gatcctccta attgccatca acaagtatgg ggtcagcctc atcgatccca    3960
aaacgaagga tatcctcacc actcatccct tcaccaagat ctccaactgg agcagcggca    4020
acacctactt ccacatcacc attgggaact tggtgcgcgg gagcaaactg ctctgcgaga    4080
cgtcactggg ctacaagatg gatgacctcc tgacttccta cattagccag atgctcacag    4140
ccatgagcaa acagcggggc tccaggagcg gcaagtgagg taccaagggc gaattctgca    4200
gtcgactaga gctcgctgat cagcctcgac tgtgccttct agttgccagc catctgttgt    4260
ttgcccctcc cccgtgcctt ccttgaccct ggaaggtgcc actcccactg tcctttccta    4320
ataaaatgag gaaattgcat cgcattgtct gagtaggtgt cattctattc tggggggtgg    4380
ggtggggcag gacagcaagg gggaggattg ggaagacaat agcaggcatg ctggggagag    4440
atctgaggac tagtccgtcg actgttaatt aagcatgctg gggagagatc taggaacccc    4500
tagtgatgga gttggccact ccctctctgc gcgctcgctc gctcactgag gccgcccggg    4560
caaagcccgg gcgtcgggcg acctttggtc gcccggcctc agtgagcgag cgagcgcgca    4620
gagagggagt ggccaacccc cccccccccc ccctgcagc cctgcattaa tgaatcggcc    4680
aacgcgcggg gagaggcggt ttgcgtattg ggcgctcttc cgcttcctcg ctcactgact    4740
cgctgcgctc ggtcgttcgg ctgcggcgag cggtatcagc tcactcaaag gcggtaatac    4800
ggttatccac agaatcaggg gataacgcag gaaagaacat gtgagcaaaa ggccagcaaa    4860
aggccaggaa ccgtaaaaag gccgcgttgc tggcgttttt ccataggctc cgcccccctg    4920
acgagcatca aaaaatcga cgctcaagtc agaggtggcg aaacccgaca ggactataaa    4980
gataccaggc gtttccccct ggaagctccc tcgtgcgctc tcctgttccg accctgccgc    5040
ttaccggata cctgtccgcc tttctccctt cgggaagcgt ggcgctttct caatgctcac    5100
gctgtaggta tctcagttcg gtgtaggtcg ttcgctccaa gctgggctgt gtgcacgaac    5160 ccccccgttca gcccgaccgc tgcgccttat ccggtaacta tcgtcttgag tccaacccgg    5220
taagacacga cttatcgcca ctggcagcag ccactggtaa caggattagc agagcgaggt    5280
atgtaggcgg tgctacagag ttcttgaagt ggtggcctaa ctacggctac actagaagga    5340
cagtatttgg tatctgcgct ctgctgaagc cagttacctt cggaaaaaga gttggtagct    5400
cttgatccgg caaacaaacc accgctggta gcggtggttt ttttgtttgc aagcagcaga    5460
ttacgcgcag aaaaaaagga tctcaagaag atcctttgat cttttctacg gggtctgacg    5520
```

```
ctcagtggaa cgaaaactca cgttaaggga ttttggtcat gagattatca aaaggatct    5580
tcacctagat cctttaaat taaaaatgaa gttttaaatc aatctaaagt atatatgagt    5640
aaacttggtc tgacagttac caatgcttaa tcagtgaggc acctatctca gcgatctgtc    5700
tatttcgttc atccatagtt gcctgactcc ccgtcgtgta gataactacg atacgggagg    5760
gcttaccatc tggccccagt gctgcaatga taccgcgaga cccacgctca ccggctccag    5820
atttatcagc aataaaccag ccagccggaa gggccgagcg cagaagtggt cctgcaactt    5880
tatccgcctc catccagtct attaattgtt gccgggaagc tagagtaagt agttcgccag    5940
ttaatagttt gcgcaacgtt gttgccattg ctacaggcat cgtggtgtca cgctcgtcgt    6000
ttggtatggc ttcattcagc tccggttccc aacgatcaag gcgagttaca tgatccccca    6060
tgttgtgcaa aaaagcggtt agctccttcg gtcctccgat cgttgtcaga agtaagttgg    6120
ccgcagtgtt atcactcatg gttatggcag cactgcataa ttctcttact gtcatgccat    6180
ccgtaagatg cttttctgtg actggtgagt actcaaccaa gtcattctga aatagtgta    6240
tgcggcgacc gagttgctct tgcccggcgt caatacggga taataccgcg ccacatagca    6300
gaactttaaa agtgctcatc attggaaaac gttcttcggg gcgaaaactc tcaaggatct    6360
taccgctgtt gagatccagt tcgatgtaac ccactcgtgc acccaactga tcttcagcat    6420
cttttacttt caccagcgtt tctgggtgag caaaaacagg aaggcaaaat gccgcaaaaa    6480
agggaataag ggcgacacgg aaatgttgaa tactcatact cttcctttt caatattatt    6540
gaagcattta tcagggttat tgtctcatga gcggatacat atttgaatgt atttagaaaa    6600
ataaacaaat aggggttccg cgcacatttc cccgaaaagt gccacctgac gtctaagaaa    6660
ccattattat catgacatta acctataaaa ataggcgtat cacgaggccc tttcgtctcg    6720
cgcgtttcgg tgatgacggt gaaaacctct gacacatgca gctcccggag acggtcacag    6780
cttgtctgta agcggatgcc gggagcagac aagcccgtca gggcgcgtca gcgggtgttg    6840
gcgggtgtcg ggctggctt aactatgcgg catcagagca gattgtactg agagtgcacc    6900
atatgcggtg tgaaataccg cacagatgcg taaggagaaa ataccgcatc aggaaattgt    6960
aaacgttaat attttgttaa aattcgcgtt aaattttgt taaatcagct cattttttaa    7020
ccaataggcc gaaatcggca aaatccctta taaatcaaaa gaatagaccg agatagggtt    7080
gagtgttgtt ccagtttgga acaagagtcc actattaaag aacgtggact ccaacgtcaa    7140
agggcgaaaa accgtctatc agggcgatgg cccactacgt gaaccatcac cctaatcaag    7200
ttttttgggg tcgaggtgcc gtaaagcact aaatcggaac cctaaaggga gccccccgatt    7260
tagagcttga cggggaaagc cggcgaacgt ggcgagaaag gaagggaaga agcgaaagg    7320
agcgggcgct agggcgctgg caagtgtagc ggtcacgctg cgcgtaacca ccacacccgc    7380
cgcgcttaat gcgccgctac agggcgcgtc gcgccattcg ccattcaggc tacgcaactg    7440
ttgggaaggg cgatcggtgc gggcctcttc gctatta                          7477
```

<210> SEQ ID NO 5
<211> LENGTH: 7465
<212> TYPE: DNA
<213> ORGANISM: Homo sapiens

<400> SEQUENCE: 5

```
gctctgggca ggagagagag tgagagacaa gagacacaca cagagagacg gcgaggaagg     60
gaaagaccca gagggacgcc tagaacgaga cttggagcca gacagaggaa gagggggacgt   120
gtgtttgcag actggctggg cccgtgaccc agcttcctga gtcctccgtg caggtggcag    180
```

```
ctgtaccagg ctggcaggtc actgagagtg ggcagctggg ccccagaact gtgcctggcc      240
cagtgggcag caggagctcc tgacttggga ccatggtgat tcttcagcag ggggaccatg      300
tgtggatgga cctgagattg gggcaggagt tcgacgtgcc catcggggcg gtggtgaagc      360
tctgcgactc tgggcaggtc caggtggtgg atgatgaaga caatgaacac tggatctctc      420
cgcagaacgc aacgcacatc aagcctatgc accccacgtc ggtccacggc gtggaggaca      480
tgatccgcct gggggacctc aacgaggcgg gcatcttgcg caacctgctt atccgctacc      540
gggaccacct catctacacg tatacgggct ccatcctggt ggctgtgaac ccctaccagc      600
tgctctccat ctactcgcca gagcacatcc gccagtatac caacaagaag attggggaga      660
tgccccccca catctttgcc attgctgaca actgctactt caacatgaaa cgcaacagcc      720
gagaccagtg ctgcatcatc agtggggaat ctggggccgg aagacggag agcacaaagc      780 tgatcctgca gttcctggca gccatcagtg ggcagcactc gtggattgag cagcaggtct      840
tggaggccac ccccattctg gaagcatttg gaatgccaa gaccatccgc aatgacaact      900
caagccgttt cggaaagtac atcgacatcc acttcaacaa gcgggcgcc atcgagggcg      960 cgaagattga gcagtacctg ctggaaaagt cacgtgtctg tcgccaggcc ctggatgaaa      1020
ggaactacca cgtgttctac tgcatgctgg agggtatgag tgaggatcag aagaagaagc      1080
tgggcttggg ccaggcctct gactacaact acttggccat gggtaactgc ataacctgtg      1140
agggccgggt ggacagccag gagtacgcca acatccgctc cgccatgaag gtgctcatgt      1200
tcactgacac cgagaactgg gagatctcga agctcctggc tgccatcctg cacctgggca      1260
acctgcagta tgaggcacgc acatttgaaa acctggatgc ctgtgaggtt ctcttctccc      1320
catcgctggc cacagctgca tccctgcttg aggtgaaccc cccagacctg atgagctgcc      1380
tgactagccg caccctcatc acccgcgggg agacggtgtc caccccactg agcagggaac      1440
aggcactgga cgtgcgcgac gccttcgtaa aggggatcta cggcggctg ttcgtgtgga      1500 ttgtggacaa gatcaacgca gcaatttaca agcctccctc ccaggatgtg aagaactctc      1560
gcaggtccat cggcctcctg gacatctttg ggtttgagaa cttttgctgtg aacagctttg      1620 agcagctctg catcaacttc gccaatgagc acctgcagca gttctttgtg cggcacgtgt      1680
tcaagctgga gcaggaggaa tatgacctgg agagcattga ctggctgcac atcgagttca      1740
ctgacaacca ggatgccctg gacatgattg ccaacaagcc catgaacatc atctccctca      1800
tcgatgagga gagcaagttc cccaagggca cagacaccac catgttacac aagctgaact      1860
cccagcacaa gctcaacgcc aactacatcc ccccaagaa caaccatgag cccagtttg      1920 gcatcaacca tttttgcagg catcgtctact atgagaccca aggcttcctg gagaagaacc      1980
gagacaccct gcatggggac attatccagc tggtccactc ctccaggaac aagttcatca      2040
agcagatctt ccaggccgat gtcgccatgg gcgccgagac caggaagcgc tcgcccacac      2100
ttagcagcca gttcaagcgg tcactggagc tgctgatgcg cacgctgggt gcctgccagc      2160
ccttctttgt gcgatgcatc aagcccaatg agttcaagaa gcccatgctg ttcgaccggc      2220
acctgtgcgt gcgccagctg cggtactcag gaatgatgga gaccatccga atccgccgag      2280
ctggctaccc catccgctac agcttcgtag agtttgtgga gcggtaccgt gtgctgctgc      2340
caggtgtgaa gccggcctac aagcagggcg acctccgcgg gacttgccag cgcatggctg      2400
aggctgtgct gggcacccac gatgactggc agataggcaa aaccaagatc tttctgaagg      2460
accaccatga catgctgctg gaagtggagc gggacaaagc catcaccgac agagtcatcc      2520
```

```
tccttcagaa agtcatccgg ggattcaaag acaggtctaa ctttctgaag ctgaagaacg    2580
ctgccacact gatccagagg cactggcggg gtcacaactg taggaagaac tacgggctga    2640
tgcgtctggg cttcctgcgg ctgcaggccc tgcaccgctc ccggaagctg caccagcagt    2700
accgcctggc ccgccagcgc atcatccagt tccaggcccg ctgccgcgcc tatctggtgc    2760
gcaaggcctt ccgccaccgc ctctgggctg tgctcaccgt gcaggcctat gcccggggca    2820
tgatcgcccg caggctgcac caacgcctca gggctgagta tctgtggcgc ctcgaggctg    2880
agaaaatgcg gctggcggag gaagagaagc ttcggaagga gatgagcgcc aagaaggcca    2940
aggaggaggc cgagcgcaag catcaggagc gcctggccca gctggctcgt gaggacgctg    3000
agcgggagct gaaggagaag gaggccgctc ggcggaagaa ggagctcctg gagcagatgg    3060
aaagggcccg ccatgagcct gtcaatcact cagacatggt ggacaagatg tttggcttcc    3120
tggggacttc aggtggcctg ccaggccagg agggccaggc acctagtggc tttgaggacc    3180
tggagcgagg gcggagggag atggtggagg aggacctgga tgcagccctg cccctgcctg    3240
acgaggatga ggaggacctc tctgagtata aatttgccaa gttcgcggcc acctacttcc    3300
aggggacaac cacgcactcc tacacccggc ggccactcaa acagccactg ctctaccatg    3360
acgacgaggg tgaccagctg gcagccctgg cggtctggat caccatcctc cgcttcatgg    3420
gggacctccc tgagcccaag taccacacag ccatgagtga tggcagtgag aagatccctg    3480
tgatgaccaa gatttatgag accctgggca agaagacgta caagagggag ctgcaggccc    3540
tgcagggcga gggcgaggcc cagctccccg agggccagaa gaagagcagt gtgaggcaca    3600
agctggtgca tttgactctg aaaaagaagt ccaagctcac agaggaggtg accaagaggc    3660
tgcatgacgg ggagtccaca gtgcagggca acagcatgct ggaggaccgg cccacctcca    3720
acctggagaa gctgcacttc atcatcggca atggcatcct gcggcagca ctccgggacg    3780
agatctactg ccagatcagc aagcagctga cccacaaccc ctccaagagc agctatgccc    3840
ggggctggat tctcgtgtct ctctgcgtgg gctgtttcgc cccctccgag aagtttgtca    3900
agtacctgcg gaacttcatc cacgggggcc cgccggcta cgccccgtac tgtgaggagc    3960
gcctgagaag gacctttgtc aatgggacac ggacacagcc gcccagctgg ctggagctgc    4020
aggccaccaa gtccaagaag ccaatcatgt tgcccgtgac attcatggat gggaccacca    4080
agaccctgct gacggactcg gcaaccacgg ccaaggagct ctgcaacgcg ctggccgaca    4140
agatctctct caaggaccgg ttcggggttct ccctctacat tgccctgttt gacaaggtgt    4200
cctccctggg cagcggcagt gaccacgtca tggacgccat ctcccagtgc gagcagtacg    4260
ccaaggagca gggcgcccag gagcgcaacg cccctggag gctcttcttc cgcaaagagg    4320
tcttcacgcc ctggcacagc ccctccgagg acaacgtggc caccaacctc atctaccagc    4380
aggtggtgcg aggagtcaag tttggggagt acaggtgtga aaggaggag gacctggctg    4440
agctggcctc ccagcagtac tttgtagact atggctctga gatgatcctg agcgcctcc    4500
tgaacctcgt gcccacctac atccccgacc gcgagatcac gccctgaag acgctggaga    4560
agtgggccca gctggccatc gccgcccaca gaagggat ttatgcccag aggagaactg    4620
atgcccagaa ggtcaagag gatgtggtca gttatgcccg cttcaagtgg cccttgctct    4680
tctccaggtt ttatgaagcc tacaaattct caggcccag tctccccaag aacgacgtca    4740
tcgtggccgt caactggacg ggtgtgtact ttgtggatga gcaggagcag gtacttctgg    4800
agctgtcctt cccagagatc atggccgtgt ccagcagcag ggagtgccgt gtctggctct    4860
cactgggctg ctctgatctt ggctgtgctg cgcctcactc aggctgggca ggactgaccc    4920
```

```
cggcggggcc ctgttctccg tgttggtcct gcagggagc gaaaacgacg gcccccagct   4980
tcacgctggc caccatcaag ggggacgaat acaccttcac ctccagtaat gctgaggaca   5040
ttcgtgacct ggtggtcacc ttcctagagg ggctccggaa gagatctaag tatgttgtgg   5100
ccctgcagga taaccccaac cccgcaggcg aggagtcagg cttcctcagc tttgccaagg   5160
gagacctcat catcctggac catgacacgg gcgagcaggt catgaactcg ggctgggcca   5220
acggcatcaa tgagaggacc aagcagcgtg gggacttccc caccgactgt gtgtacgtca   5280
tgcccactgt caccatgcca ccgcgggaga ttgtggccct ggtcaccatg actcccgatc   5340
agaggcagga cgttgtccgg ctcttgcagc tgcgaacggc ggagcccgag gtgcgtgcca   5400
agccctacac gctggaggag ttttcctatg actacttcag gccccaccc aagcacacgc   5460 tgagccgtgt catggtgtcc aaggcccgag gcaaggaccg gctgtggagc cacacgcggg   5520
aaccgctcaa gcaggcgctg ctcaagaagc tcctgggcag tgaggagctc tcgcaggagg   5580
cctgcctggc cttcattgct gtgctcaagt acatgggcga ctacccgtcc aagaggacac   5640
gctccgtcaa cgagctcacc gaccagatct ttgagggtcc cctgaaagcc gagcccctga   5700
aggacgaggc atatgtgcag atcctgaagc agctgaccga caaccacatc aggtacagcg   5760
aggagcgggg ttgggagctg ctctggctgt gcacgggcct ttcccaccc agcaacatcc   5820 tcctgcccca cgtgcagcgc ttcctgcagt cccgaaagca ctgccactc gccatcgact   5880 gcctgcaacg gctccagaaa gccctgagaa acgggtcccg gaagtaccct ccgcacctgg   5940
tggaggtgga ggccatccag cacaagacca cccagatttt ccacaaggtc tacttccctg   6000
atgacactga cgaggccttc gaagtggagt ccagcaccaa ggccaaggac ttctgccaga   6060
acatcgccac caggctgctc ctcaagtcct cagagggatt cagcctcttt gtcaaaattg   6120
cagacaaggt catcagcgtt cctgagaatg acttcttctt tgactttgtt cgacacttga   6180
cagactggat aaagaaagct cggcccatca aggacggaat tgtgccctca ctcacctacc   6240
aggtgttctt catgaagaag ctgtggacca ccacggtgcc agggaaggat cccatggccg   6300
attccatctt ccactattac caggagttgc ccaagtatct ccgaggctac cacaagtgca   6360
cgcgggagga ggtgctgcag ctgggggcgc tgatctacag ggtcaagttc gaggaggaca   6420
agtcctactt ccccagcatc cccaagctgc tgcgggagct ggtgcccag gaccttatcc   6480 ggcaggtctc acctgatgac tggaagcggt ccatcgtcgc ctacttcaac aagcacgcag   6540
ggaagtccaa ggaggaggcc aagctggcct tcctgaagct catcttcaag tggcccacct   6600
ttggctcagc cttcttcgag gtgaagcaaa ctacggagcc aaacttccct gagatcctcc   6660
taattgccat caacaagtat ggggtcagcc tcatcgatcc caaaacgaag gatatcctca   6720
ccactcatcc cttcaccaag atctccaact ggagcagcgg caacacctac ttccacatca   6780
ccattgggaa cttggtgcgc gggagcaaac tgctctgcga cgtcactg ggctacaaga   6840 tggatgacct cctgacttcc tacattagcc agatgctcac agccatgagc aaacagcggg   6900
gctccaggag cggcaagtga acagtcacgg ggaggtgctg gttccatgcc tgctctcgag   6960
gcagcagtgg gttcaggccc atcagctacc cctgcagctg gggaagactt atgccatccc   7020
ggcagcgagg ctgggctggc cagccaccac tgactatacc aactgggcct ctgatgttct   7080
tccagtgagg catctctctg ggatgcagaa cttccctcca tccacccctc tggcacctgg   7140
gttggtctaa tccagttttg ctgtggcctt cccggttgtg agagcctgtg atccttagat   7200
gtgtctcctg tttcagacca gccccaccat gcaacttcct ttgactttct gtgtaccact   7260
```

-continued

```
gggatagagg aatcaagagg acaatctagc tctccatact ttgaacaacc aaatgtgcat      7320
tgaatactct gaaaccgaag ggactggatc tgcaggtggg atgagggaga cagaccactt      7380
ttctatattg cagtgtgaat gctgggcccc tgctcaagtc taccctgatc acctcagggc      7440
ataaagcatg tttcattctc tgaaa                                            7465
```

<210> SEQ ID NO 6
<211> LENGTH: 2215
<212> TYPE: PRT
<213> ORGANISM: Homo sapiens

<400> SEQUENCE: 6

```
Met Val Ile Leu Gln Gln Gly Asp His Val Trp Met Asp Leu Arg Leu
1               5                   10                  15

Gly Gln Glu Phe Asp Val Pro Ile Gly Ala Val Val Lys Leu Cys Asp
                20                  25                  30

Ser Gly Gln Val Gln Val Val Asp Asp Glu Asp Asn Glu His Trp Ile
            35                  40                  45

Ser Pro Gln Asn Ala Thr His Ile Lys Pro Met His Pro Thr Ser Val
        50                  55                  60

His Gly Val Glu Asp Met Ile Arg Leu Gly Asp Leu Asn Glu Ala Gly
65                  70                  75                  80

Ile Leu Arg Asn Leu Leu Ile Arg Tyr Arg Asp His Leu Ile Tyr Thr
                85                  90                  95

Tyr Thr Gly Ser Ile Leu Val Ala Val Asn Pro Tyr Gln Leu Leu Ser
                100                 105                 110

Ile Tyr Ser Pro Glu His Ile Arg Gln Tyr Thr Asn Lys Lys Ile Gly
            115                 120                 125

Glu Met Pro Pro His Ile Phe Ala Ile Ala Asp Asn Cys Tyr Phe Asn
        130                 135                 140

Met Lys Arg Asn Ser Arg Asp Gln Cys Cys Ile Ile Ser Gly Glu Ser
145                 150                 155                 160

Gly Ala Gly Lys Thr Glu Ser Thr Lys Leu Ile Leu Gln Phe Leu Ala
                165                 170                 175

Ala Ile Ser Gly Gln His Ser Trp Ile Glu Gln Gln Val Leu Glu Ala
                180                 185                 190

Thr Pro Ile Leu Glu Ala Phe Gly Asn Ala Lys Thr Ile Arg Asn Asp
            195                 200                 205

Asn Ser Ser Arg Phe Gly Lys Tyr Ile Asp Ile His Phe Asn Lys Arg
        210                 215                 220

Gly Ala Ile Glu Gly Ala Lys Ile Glu Gln Tyr Leu Leu Glu Lys Ser
225                 230                 235                 240

Arg Val Cys Arg Gln Ala Leu Asp Glu Arg Asn Tyr His Val Phe Tyr
                245                 250                 255

Cys Met Leu Glu Gly Met Ser Glu Asp Gln Lys Lys Lys Leu Gly Leu
                260                 265                 270

Gly Gln Ala Ser Asp Tyr Asn Tyr Leu Ala Met Gly Asn Cys Ile Thr
            275                 280                 285

Cys Glu Gly Arg Val Asp Ser Gln Glu Tyr Ala Asn Ile Arg Ser Ala
        290                 295                 300

Met Lys Val Leu Met Phe Thr Asp Thr Glu Asn Trp Glu Ile Ser Lys
305                 310                 315                 320

Leu Leu Ala Ala Ile Leu His Leu Gly Asn Leu Gln Tyr Glu Ala Arg
                325                 330                 335
```

Thr Phe Glu Asn Leu Asp Ala Cys Glu Val Leu Phe Ser Pro Ser Leu
            340                 345                 350

Ala Thr Ala Ala Ser Leu Leu Glu Val Asn Pro Pro Asp Leu Met Ser
        355                 360                 365

Cys Leu Thr Ser Arg Thr Leu Ile Thr Arg Gly Glu Thr Val Ser Thr
    370                 375                 380

Pro Leu Ser Arg Glu Gln Ala Leu Asp Val Arg Asp Ala Phe Val Lys
385                 390                 395                 400

Gly Ile Tyr Gly Arg Leu Phe Val Trp Ile Val Asp Lys Ile Asn Ala
            405                 410                 415

Ala Ile Tyr Lys Pro Pro Ser Gln Asp Val Lys Asn Ser Arg Arg Ser
        420                 425                 430

Ile Gly Leu Leu Asp Ile Phe Gly Phe Glu Asn Phe Ala Val Asn Ser
    435                 440                 445

Phe Glu Gln Leu Cys Ile Asn Phe Ala Asn Glu His Leu Gln Gln Phe
        450                 455                 460

Phe Val Arg His Val Phe Lys Leu Glu Gln Glu Glu Tyr Asp Leu Glu
465                 470                 475                 480

Ser Ile Asp Trp Leu His Ile Glu Phe Thr Asp Asn Gln Asp Ala Leu
            485                 490                 495

Asp Met Ile Ala Asn Lys Pro Met Asn Ile Ile Ser Leu Ile Asp Glu
        500                 505                 510

Glu Ser Lys Phe Pro Lys Gly Thr Asp Thr Thr Met Leu His Lys Leu
    515                 520                 525

Asn Ser Gln His Lys Leu Asn Ala Asn Tyr Ile Pro Pro Lys Asn Asn
530                 535                 540

His Glu Thr Gln Phe Gly Ile Asn His Phe Ala Gly Ile Val Tyr Tyr
545                 550                 555                 560

Glu Thr Gln Gly Phe Leu Glu Lys Asn Arg Asp Thr Leu His Gly Asp
            565                 570                 575

Ile Ile Gln Leu Val His Ser Ser Arg Asn Lys Phe Ile Lys Gln Ile
        580                 585                 590

Phe Gln Ala Asp Val Ala Met Gly Ala Glu Thr Arg Lys Arg Ser Pro
    595                 600                 605

Thr Leu Ser Ser Gln Phe Lys Arg Ser Leu Glu Leu Leu Met Arg Thr
610                 615                 620

Leu Gly Ala Cys Gln Pro Phe Phe Val Arg Cys Ile Lys Pro Asn Glu
625                 630                 635                 640

Phe Lys Lys Pro Met Leu Phe Asp Arg His Leu Cys Val Arg Gln Leu
            645                 650                 655

Arg Tyr Ser Gly Met Met Glu Thr Ile Arg Ile Arg Arg Ala Gly Tyr
        660                 665                 670

Pro Ile Arg Tyr Ser Phe Val Glu Phe Val Glu Arg Tyr Arg Val Leu
    675                 680                 685

Leu Pro Gly Val Lys Pro Ala Tyr Lys Gln Gly Asp Leu Arg Gly Thr
690                 695                 700

Cys Gln Arg Met Ala Glu Ala Val Leu Gly Thr His Asp Asp Trp Gln
705                 710                 715                 720

Ile Gly Lys Thr Lys Ile Phe Leu Lys Asp His His Asp Met Leu Leu
            725                 730                 735

Glu Val Glu Arg Asp Lys Ala Ile Thr Asp Arg Val Ile Leu Leu Gln
        740                 745                 750

Lys Val Ile Arg Gly Phe Lys Asp Arg Ser Asn Phe Leu Lys Leu Lys

```
                755                 760                 765
Asn Ala Ala Thr Leu Ile Gln Arg His Trp Arg Gly His Asn Cys Arg
    770                 775                 780
Lys Asn Tyr Gly Leu Met Arg Leu Gly Phe Leu Arg Leu Gln Ala Leu
785                 790                 795                 800
His Arg Ser Arg Lys Leu His Gln Gln Tyr Arg Leu Ala Arg Gln Arg
                805                 810                 815
Ile Ile Gln Phe Gln Ala Arg Cys Arg Ala Tyr Leu Val Arg Lys Ala
                820                 825                 830
Phe Arg His Arg Leu Trp Ala Val Leu Thr Val Gln Ala Tyr Ala Arg
                835                 840                 845
Gly Met Ile Ala Arg Arg Leu His Gln Arg Leu Arg Ala Glu Tyr Leu
                850                 855                 860
Trp Arg Leu Glu Ala Glu Lys Met Arg Leu Ala Glu Glu Lys Leu
865                 870                 875                 880
Arg Lys Glu Met Ser Ala Lys Lys Ala Lys Glu Ala Glu Arg Lys
                885                 890                 895
His Gln Glu Arg Leu Ala Gln Leu Ala Arg Glu Asp Ala Glu Arg Glu
                900                 905                 910
Leu Lys Glu Lys Glu Ala Ala Arg Arg Lys Lys Glu Leu Leu Glu Gln
                915                 920                 925
Met Glu Arg Ala Arg His Glu Pro Val Asn His Ser Asp Met Val Asp
                930                 935                 940
Lys Met Phe Gly Phe Leu Gly Thr Ser Gly Gly Leu Pro Gly Gln Glu
945                 950                 955                 960
Gly Gln Ala Pro Ser Gly Phe Glu Asp Leu Glu Arg Gly Arg Arg Glu
                965                 970                 975
Met Val Glu Glu Asp Leu Asp Ala Ala Leu Pro Leu Pro Asp Glu Asp
                980                 985                 990
Glu Glu Asp Leu Ser Glu Tyr Lys Phe Ala Lys Phe Ala Ala Thr Tyr
                995                 1000                1005
Phe Gln Gly Thr Thr Thr His Ser Tyr Thr Arg Arg Pro Leu Lys
    1010                1015                1020
Gln Pro Leu Leu Tyr His Asp Asp Glu Gly Asp Gln Leu Ala Ala
    1025                1030                1035
Leu Ala Val Trp Ile Thr Ile Leu Arg Phe Met Gly Asp Leu Pro
    1040                1045                1050
Glu Pro Lys Tyr His Thr Ala Met Ser Asp Gly Ser Glu Lys Ile
    1055                1060                1065
Pro Val Met Thr Lys Ile Tyr Glu Thr Leu Gly Lys Lys Thr Tyr
    1070                1075                1080
Lys Arg Glu Leu Gln Ala Leu Gln Gly Glu Gly Glu Ala Gln Leu
    1085                1090                1095
Pro Glu Gly Gln Lys Lys Ser Ser Val Arg His Lys Leu Val His
    1100                1105                1110
Leu Thr Leu Lys Lys Lys Ser Lys Leu Thr Glu Glu Val Thr Lys
    1115                1120                1125
Arg Leu His Asp Gly Glu Ser Thr Val Gln Gly Asn Ser Met Leu
    1130                1135                1140
Glu Asp Arg Pro Thr Ser Asn Leu Glu Lys Leu His Phe Ile Ile
    1145                1150                1155
Gly Asn Gly Ile Leu Arg Pro Ala Leu Arg Asp Glu Ile Tyr Cys
    1160                1165                1170
```

-continued

Gln Ile Ser Lys Gln Leu Thr His Asn Pro Ser Lys Ser Ser Tyr
1175                1180                1185

Ala Arg Gly Trp Ile Leu Val Ser Leu Cys Val Gly Cys Phe Ala
1190                1195                1200

Pro Ser Glu Lys Phe Val Lys Tyr Leu Arg Asn Phe Ile His Gly
1205                1210                1215

Gly Pro Pro Gly Tyr Ala Pro Tyr Cys Glu Arg Leu Arg Arg
1220                1225                1230

Thr Phe Val Asn Gly Thr Arg Thr Gln Pro Pro Ser Trp Leu Glu
1235                1240                1245

Leu Gln Ala Thr Lys Ser Lys Lys Pro Ile Met Leu Pro Val Thr
1250                1255                1260

Phe Met Asp Gly Thr Thr Lys Thr Leu Leu Thr Asp Ser Ala Thr
1265                1270                1275

Thr Ala Lys Glu Leu Cys Asn Ala Leu Ala Asp Lys Ile Ser Leu
1280                1285                1290

Lys Asp Arg Phe Gly Phe Ser Leu Tyr Ile Ala Leu Phe Asp Lys
1295                1300                1305

Val Ser Ser Leu Gly Ser Gly Ser Asp His Val Met Asp Ala Ile
1310                1315                1320

Ser Gln Cys Glu Gln Tyr Ala Lys Glu Gln Gly Ala Gln Glu Arg
1325                1330                1335

Asn Ala Pro Trp Arg Leu Phe Phe Arg Lys Glu Val Phe Thr Pro
1340                1345                1350

Trp His Ser Pro Ser Glu Asp Asn Val Ala Thr Asn Leu Ile Tyr
1355                1360                1365

Gln Gln Val Val Arg Gly Val Lys Phe Gly Glu Tyr Arg Cys Glu
1370                1375                1380

Lys Glu Asp Asp Leu Ala Glu Leu Ala Ser Gln Gln Tyr Phe Val
1385                1390                1395

Asp Tyr Gly Ser Glu Met Ile Leu Glu Arg Leu Leu Asn Leu Val
1400                1405                1410

Pro Thr Tyr Ile Pro Asp Arg Glu Ile Thr Pro Leu Lys Thr Leu
1415                1420                1425

Glu Lys Trp Ala Gln Leu Ala Ile Ala Ala His Lys Lys Gly Ile
1430                1435                1440

Tyr Ala Gln Arg Arg Thr Asp Ala Gln Lys Val Lys Glu Asp Val
1445                1450                1455

Val Ser Tyr Ala Arg Phe Lys Trp Pro Leu Leu Phe Ser Arg Phe
1460                1465                1470

Tyr Glu Ala Tyr Lys Phe Ser Gly Pro Ser Leu Pro Lys Asn Asp
1475                1480                1485

Val Ile Val Ala Val Asn Trp Thr Gly Val Tyr Phe Val Asp Glu
1490                1495                1500

Gln Glu Gln Val Leu Leu Glu Leu Ser Phe Pro Glu Ile Met Ala
1505                1510                1515

Val Ser Ser Arg Glu Cys Arg Val Trp Leu Ser Leu Gly Cys
1520                1525                1530

Ser Asp Leu Gly Cys Ala Ala Pro His Ser Gly Trp Ala Gly Leu
1535                1540                1545

Thr Pro Ala Gly Pro Cys Ser Pro Cys Trp Ser Cys Arg Gly Ala
1550                1555                1560

```
Lys Thr Thr Ala Pro Ser Phe Thr Leu Ala Thr Ile Lys Gly Asp
1565                1570                1575

Glu Tyr Thr Phe Thr Ser Ser Asn Ala Glu Asp Ile Arg Asp Leu
    1580                1585                1590

Val Val Thr Phe Leu Glu Gly Leu Arg Lys Arg Ser Lys Tyr Val
    1595                1600                1605

Val Ala Leu Gln Asp Asn Pro Asn Pro Ala Gly Glu Glu Ser Gly
    1610                1615                1620

Phe Leu Ser Phe Ala Lys Gly Asp Leu Ile Ile Leu Asp His Asp
    1625                1630                1635

Thr Gly Glu Gln Val Met Asn Ser Gly Trp Ala Asn Gly Ile Asn
    1640                1645                1650

Glu Arg Thr Lys Gln Arg Gly Asp Phe Pro Thr Asp Cys Val Tyr
    1655                1660                1665

Val Met Pro Thr Val Thr Met Pro Pro Arg Glu Ile Val Ala Leu
    1670                1675                1680

Val Thr Met Thr Pro Asp Gln Arg Gln Asp Val Val Arg Leu Leu
    1685                1690                1695

Gln Leu Arg Thr Ala Glu Pro Glu Val Arg Ala Lys Pro Tyr Thr
    1700                1705                1710

Leu Glu Glu Phe Ser Tyr Asp Tyr Phe Arg Pro Pro Pro Lys His
    1715                1720                1725

Thr Leu Ser Arg Val Met Val Ser Lys Ala Arg Gly Lys Asp Arg
    1730                1735                1740

Leu Trp Ser His Thr Arg Glu Pro Leu Lys Gln Ala Leu Leu Lys
    1745                1750                1755

Lys Leu Leu Gly Ser Glu Glu Leu Ser Gln Glu Ala Cys Leu Ala
    1760                1765                1770

Phe Ile Ala Val Leu Lys Tyr Met Gly Asp Tyr Pro Ser Lys Arg
    1775                1780                1785

Thr Arg Ser Val Asn Glu Leu Thr Asp Gln Ile Phe Glu Gly Pro
    1790                1795                1800

Leu Lys Ala Glu Pro Leu Lys Asp Glu Ala Tyr Val Gln Ile Leu
    1805                1810                1815

Lys Gln Leu Thr Asp Asn His Ile Arg Tyr Ser Glu Glu Arg Gly
    1820                1825                1830

Trp Glu Leu Leu Trp Leu Cys Thr Gly Leu Phe Pro Pro Ser Asn
    1835                1840                1845

Ile Leu Leu Pro His Val Gln Arg Phe Leu Gln Ser Arg Lys His
    1850                1855                1860

Cys Pro Leu Ala Ile Asp Cys Leu Gln Arg Leu Gln Lys Ala Leu
    1865                1870                1875

Arg Asn Gly Ser Arg Lys Tyr Pro Pro His Leu Val Glu Val Glu
    1880                1885                1890

Ala Ile Gln His Lys Thr Thr Gln Ile Phe His Lys Val Tyr Phe
    1895                1900                1905

Pro Asp Asp Thr Asp Glu Ala Phe Glu Val Glu Ser Ser Thr Lys
    1910                1915                1920

Ala Lys Asp Phe Cys Gln Asn Ile Ala Thr Arg Leu Leu Leu Lys
    1925                1930                1935

Ser Ser Glu Gly Phe Ser Leu Phe Val Lys Ile Ala Asp Lys Val
    1940                1945                1950

Ile Ser Val Pro Glu Asn Asp Phe Phe Asp Phe Val Arg His
```

| | | | | | | | | | | |
|---|---|---|---|---|---|---|---|---|---|---|
| | | 1955 | | | 1960 | | | 1965 | | |
| Leu | Thr | Asp | Trp | Ile | Lys | Lys | Ala | Arg | Pro | Ile | Lys | Asp | Gly | Ile |
| | | 1970 | | | | 1975 | | | 1980 | |
| Val | Pro | Ser | Leu | Thr | Tyr | Gln | Val | Phe | Phe | Met | Lys | Lys | Leu | Trp |
| | | 1985 | | | | 1990 | | | 1995 | |
| Thr | Thr | Thr | Val | Pro | Gly | Lys | Asp | Pro | Met | Ala | Asp | Ser | Ile | Phe |
| | | 2000 | | | | 2005 | | | 2010 | |
| His | Tyr | Tyr | Gln | Glu | Leu | Pro | Lys | Tyr | Leu | Arg | Gly | Tyr | His | Lys |
| | | 2015 | | | | 2020 | | | 2025 | |
| Cys | Thr | Arg | Glu | Glu | Val | Leu | Gln | Leu | Gly | Ala | Leu | Ile | Tyr | Arg |
| | | 2030 | | | | 2035 | | | 2040 | |
| Val | Lys | Phe | Glu | Glu | Asp | Lys | Ser | Tyr | Phe | Pro | Ser | Ile | Pro | Lys |
| | | 2045 | | | | 2050 | | | 2055 | |
| Leu | Leu | Arg | Glu | Leu | Val | Pro | Gln | Asp | Leu | Ile | Arg | Gln | Val | Ser |
| | | 2060 | | | | 2065 | | | 2070 | |
| Pro | Asp | Asp | Trp | Lys | Arg | Ser | Ile | Val | Ala | Tyr | Phe | Asn | Lys | His |
| | | 2075 | | | | 2080 | | | 2085 | |
| Ala | Gly | Lys | Ser | Lys | Glu | Glu | Ala | Lys | Leu | Ala | Phe | Leu | Lys | Leu |
| | | 2090 | | | | 2095 | | | 2100 | |
| Ile | Phe | Lys | Trp | Pro | Thr | Phe | Gly | Ser | Ala | Phe | Phe | Glu | Val | Lys |
| | | 2105 | | | | 2110 | | | 2115 | |
| Gln | Thr | Thr | Glu | Pro | Asn | Phe | Pro | Glu | Ile | Leu | Leu | Ile | Ala | Ile |
| | | 2120 | | | | 2125 | | | 2130 | |
| Asn | Lys | Tyr | Gly | Val | Ser | Leu | Ile | Asp | Pro | Lys | Thr | Lys | Asp | Ile |
| | | 2135 | | | | 2140 | | | 2145 | |
| Leu | Thr | Thr | His | Pro | Phe | Thr | Lys | Ile | Ser | Asn | Trp | Ser | Ser | Gly |
| | | 2150 | | | | 2155 | | | 2160 | |
| Asn | Thr | Tyr | Phe | His | Ile | Thr | Ile | Gly | Asn | Leu | Val | Arg | Gly | Ser |
| | | 2165 | | | | 2170 | | | 2175 | |
| Lys | Leu | Leu | Cys | Glu | Thr | Ser | Leu | Gly | Tyr | Lys | Met | Asp | Asp | Leu |
| | | 2180 | | | | 2185 | | | 2190 | |
| Leu | Thr | Ser | Tyr | Ile | Ser | Gln | Met | Leu | Thr | Ala | Met | Ser | Lys | Gln |
| | | 2195 | | | | 2200 | | | 2205 | |
| Arg | Gly | Ser | Arg | Ser | Gly | Lys | | | | |
| | | 2210 | | | | 2215 | | | | |

```
<210> SEQ ID NO 7
<211> LENGTH: 6648
<212> TYPE: DNA
<213> ORGANISM: Homo sapiens

<400> SEQUENCE: 7
atggtgattc ttcagcaggg ggaccatgtg tggatggacc tgagattggg gcaggagttc      60
gacgtgccca tcgggcggt ggtgaagctc tgcgactctg gcaggtcca ggtggtggat      120 gatgaagaca tgaacactg gatctctccg cagaacgcaa cgcacatcaa gcctatgcac      180
cccacgtcgg tccacggcgt ggaggacatg atccgcctgg ggaccctcaa cgaggcgggc      240
atcttgcgca acctgcttat ccgctaccgg gaccacctca tctacacgta tacgggctcc      300
atcctggtgg ctgtgaaccc ctaccagctg ctctccatct actcgccaga gcacatccgc      360
cagtatacca acaagaagat tgggagatg ccccccaca tctttgccat tgctgacaac      420
tgctacttca acatgaaacg caacagccga gaccagtgct gcatcatcag tgggaatct      480 ggggccggga agacggagag cacaaagctg atcctgcagt tcctggcagc catcagtggg      540
```

```
cagcactcgt ggattgagca gcaggtcttg gaggccaccc ccattctgga agcatttggg      600
aatgccaaga ccatccgcaa tgacaactca agccgtttcg gaaagtacat cgacatccac      660
ttcaacaagc ggggcgccat cgagggcgcg aagattgagc agtacctgct ggaaaagtca      720
cgtgtctgtc gccaggccct ggatgaaagg aactaccacg tgttctactg catgctggag      780
ggtatgagtg aggatcagaa gaagaagctg ggcttgggcc aggcctctga ctacaactac      840
ttggccatgg gtaactgcat aacctgtgag ggcgggtgg acagccagga gtacgccaac       900
atccgctccg ccatgaaggt gctcatgttc actgacaccg agaactggga gatctcgaag      960
ctcctggctg ccatcctgca cctgggcaac ctgcagtatg aggcacgcac atttgaaaac     1020
ctggatgcct gtgaggttct cttctcccca tcgctggcca cagctgcatc cctgcttgag     1080
gtgaaccccc cagacctgat gagctgcctg actagccgca ccctcatcac ccgcggggag     1140
acggtgtcca ccccactgag cagggaacag gcactggacg tgcgcgacgc cttcgtaaag     1200
gggatctacg gcggctgtt cgtgtggatt gtggacaaga tcaacgcagc aatttacaag      1260
cctcccctcc aggatgtgaa gaactctcgc aggtccatcg gcctcctgga catctttggg     1320
tttgagaact tgctgtgaa cagctttgag cagctctgca tcaacttcgc caatgagcac      1380
ctgcagcagt tctttgtgcg gcacgtgttc aagctggagc aggaggaata tgacctggag     1440
agcattgact ggctgcacat cgagttcact gacaaccagg atgccctgga catgattgcc     1500
aacaagccca tgaacatcat ctccctcatc gatgaggaga gcaagttccc caagggcaca     1560
gacaccacca tgttacacaa gctgaactcc cagcacaagc tcaacgccaa ctacatcccc     1620
cccaagaaca accatgagac ccagtttggc atcaaccatt ttgcaggcat cgtctactat     1680
gagacccaag gcttcctgga gaagaaccga gacaccctgc atgggacat tatccagctg      1740 gtccactcct ccaggaacaa gttcatcaag cagatcttcc aggccgatgt cgccatgggc     1800
gccgagacca ggaagcgctc gcccacactt agcagccagt tcaagcggtc actggagctg     1860
ctgatgcgca cgctgggtgc ctgccagccc ttctttgtgc gatgcatcaa gcccaatgag     1920
ttcaagaagc ccatgctgtt cgaccggcac ctgtgcgtgc gccagctgcg gtactcagga     1980
atgatggaga ccatccgaat ccgccgagct ggctacccca tccgctacag cttcgtagag     2040
tttgtggagc ggtaccgtgt gctgctgcca ggtgtgaagc cggcctacaa gcagggcgac     2100
ctccgcggga cttgccagcg catggctgag gctgtgctgg gcacccacga tgactggcag     2160
ataggcaaaa ccaagatctt tctgaaggac caccatgaca tgctgctgga agtggagcgg     2220
gacaaagcca tcaccgacag agtcatcctc cttcagaaag tcatccgggg attcaaagac     2280
aggtctaact ttctgaagct gaagaacgct gccacactga tccagaggca ctggcggggt     2340
cacaactgta ggaagaacta cgggctgatg cgtctgggct tcctgcggct gcaggccctg     2400
caccgctccc ggaagctgca ccagcagtac cgcctggccc gccagcgcat catccagttc     2460
caggcccgct gccgcgccta tctggtgcgc aaggccttcc gccaccgcct ctgggctgtg     2520
ctcaccgtgc aggcctatgc ccggggcatg atcgcccgca ggctgcacca acgcctcagg     2580
gctgagtatc tgtggcgcct cgaggctgag aaaatgcggc tggcggagga agagaagctt     2640
cggaaggaga tgagcgccaa gaaggccaag gaggaggccg agcgcaagca tcaggagcgc     2700
ctggcccagc tggctcgtga ggacgctgag cgggagctga aggagaagga ggccgctcgg     2760
cggaagaagg agctcctgga gcagatggaa agggcccgcc atgagcctgt caatcactca     2820
gacatggtgg acaagatgtt tggcttcctg gggacttcag gtggcctgcc aggccaggag     2880
ggccaggcac ctagtggctt tgaggacctg gagcgagggc ggagggagat ggtggaggag     2940
```

```
gacctggatg cagccctgcc cctgcctgac gaggatgagg aggacctctc tgagtataaa    3000
tttgccaagt tcgcggccac ctacttccag gggacaacca cgcactccta cacccggcgg    3060
ccactcaaac agccactgct ctaccatgac gacgagggtg accagctggc agccctggcg    3120
gtctggatca ccatcctccg cttcatgggg gacctccctg agcccaagta ccacacagcc    3180
atgagtgatg gcagtgagaa gatccctgtg atgaccaaga tttatgagac cctgggcaag    3240
aagacgtaca gagggagct gcaggccctg cagggcgagg gcgaggccca gctccccgag    3300
ggccagaaga gagcagtgt gaggcacaag ctggtgcatt tgactctgaa aaagaagtcc    3360
aagctcacag aggaggtgac caagaggctg catgacgggg agtccacagt gcagggcaac    3420
agcatgctgg aggaccggcc cacctccaac ctggagaagc tgcacttcat catcggcaat    3480
ggcatcctgc ggccagcact ccgggacgag atctactgcc agatcagcaa gcagctgacc    3540
cacaacccct ccaagagcag ctatgcccgg ggctggattc tcgtgtctct ctgcgtgggc    3600
tgtttcgccc cctccgagaa gtttgtcaag tacctgcgga acttcatcca cggggggccg    3660
cccggctacg ccccgtactg tgaggagcgc ctgagaagga cctttgtcaa tgggacacgg    3720
acacagccgc ccagctggct ggagctgcag gccaccaagt ccaagaagcc aatcatgttg    3780
cccgtgacat tcatggatgg gaccaccaag accctgctga cggactcggc aaccacggcc    3840
aaggagctct gcaacgcgct ggccgacaag atctctctca aggaccggtt cgggttctcc    3900
ctctacattg ccctgtttga caaggtgtcc tccctgggca gcggcagtga ccacgtcatg    3960
gacgccatct cccagtgcga gcagtacgcc aaggagcagg gcgcccagga gcgcaacgcc    4020
ccctggaggc tcttcttccg caaagaggtc ttcacgccct ggcacagccc ctccgaggac    4080
aacgtggcca ccaacctcat ctaccagcag gtggtgcgag gagtcaagtt tggggagtac    4140
aggtgtgaga aggaggacga cctggctgag ctggcctccc agcagtactt tgtagactat    4200
ggctctgaga tgatcctgga gcgcctcctg aacctcgtgc ccacctacat ccccgaccgc    4260
gagatcacgc ccctgaagac gctggagaag tgggcccagc tggccatcgc cgcccacaag    4320
aaggggattt atgcccagag gagaactgat gcccagaagg tcaaagagga tgtggtcagt    4380
tatgcccgct tcaagtggcc cttgctcttc tccaggtttt atgaagccta caattctca    4440 ggccccagtc tccccaagaa cgacgtcatc gtggccgtca actggacggg tgtgtacttt    4500
gtggatgagc aggagcaggt acttctggag ctgtccttcc cagagatcat ggccgtgtcc    4560
agcagcaggg agtgccgtgt ctggctctca ctgggctgct ctgatcttgg ctgtgctgcg    4620
cctcactcag gctgggcagg actgaccccg gcggggccct gttctccgtg ttggtcctgc    4680
aggggagcga aaacgacggc ccccagcttc acgctggcca ccatcaaggg ggacgaatac    4740
accttcacct ccagtaatgc tgaggacatt cgtgacctgg tggtcacctt cctagagggg    4800
ctccggaaga gatctaagta tgttgtggcc ctgcaggata accccaaccc cgcaggcgag    4860
gagtcaggct tcctcagctt tgccaaggga gacctcatca tcctggacca tgacacgggc    4920
gagcaggtca tgaactcggg ctgggccaac ggcatcaatg agaggaccaa gcagcgtggg    4980
gacttcccca ccgactgtgt gtacgtcatg cccactgtca ccatgccacc gcgggagatt    5040
gtggccctgg tcaccatgac tcccgatcag aggcaggacg ttgtccggct cttgcagctg    5100
cgaacggcgg agcccgaggt gcgtgccaag ccctacacgc tggaggagtt ttcctatgac    5160
tacttcaggc cccacccaa gcacacgctg agccgtgtca tggtgtccaa ggcccgaggc    5220
aaggaccggc tgtggagcca cacgcgggaa ccgctcaagc aggcgctgct caagaagctc    5280
```

```
ctgggcagtg aggagctctc gcaggaggcc tgcctggcct tcattgctgt gctcaagtac    5340
atgggcgact acccgtccaa gaggacacgc tccgtcaacg agctcaccga ccagatcttt    5400
gagggtcccc tgaaagccga gcccctgaag gacgaggcat atgtgcagat cctgaagcag    5460
ctgaccgaca ccacatcag gtacagcgag gagcggggtt gggagctgct ctggctgtgc     5520
acgggccttt tcccacccag caacatcctc ctgccccacg tgcagcgctt cctgcagtcc    5580
cgaaagcact gcccactcgc catcgactgc ctgcaacggc tccagaaagc cctgagaaac    5640
gggtcccgga agtaccctcc gcacctggtg gaggtggagg ccatccagca aagaccacc     5700
cagatttttcc acaaggtcta cttccctgat gacactgacg aggccttcga agtggagtcc    5760
agcaccaagg ccaaggactt ctgccagaac atcgccacca ggctgctcct caagtcctca    5820
gagggattca gcctctttgt caaaattgca gacaaggtca tcagcgttcc tgagaatgac    5880
ttcttctttg actttgttcg acacttgaca gactggataa agaaagctcg gcccatcaag    5940
gacggaattg tgccctcact cacctaccag gtgttcttca tgaagaagct gtggaccacc    6000
acggtgccag ggaaggatcc catggccgat tccatcttcc actattacca ggagttgccc    6060
aagtatctcc gaggctacca caagtgcacg cgggaggagg tgctgcagct gggggcgctg    6120
atctacaggg tcaagttcga ggaggacaag tcctacttcc ccagcatccc caagctgctg    6180
cgggagctgg tgccccagga ccttatccgg caggtctcac ctgatgactg gaagcggtcc    6240
atcgtcgcct acttcaacaa gcacgcaggg aagtccaagg aggaggccaa gctggccttc    6300
ctgaagctca tcttcaagtg gccccacctt tggctcagcct tcttcgaggt gaagcaaact    6360
acggagccaa acttccctga gatcctccta attgccatca caagtatgg ggtcagcctc     6420
atcgatccca aaacgaagga tatcctcacc actcatccct tcaccaagat ctccaactgg    6480
agcagcggca acacctactt ccacatcacc attgggaact ggtgcgcgg gagcaaactg      6540
ctctgcgaga cgtcactggg ctacaagatg gatgacctcc tgacttccta cattagccag    6600
atgctcacag ccatgagcaa acagcggggc tccaggagcg gcaagtga                 6648
```

<210> SEQ ID NO 8
<211> LENGTH: 2175
<212> TYPE: PRT
<213> ORGANISM: Homo sapiens

<400> SEQUENCE: 8

```
Met Val Ile Leu Gln Gln Gly Asp His Val Trp Met Asp Leu Arg Leu
1               5                   10                  15

Gly Gln Glu Phe Asp Val Pro Ile Gly Ala Val Lys Leu Cys Asp
            20                  25                  30

Ser Gly Gln Val Gln Val Val Asp Asp Glu Asp Asn Glu His Trp Ile
        35                  40                  45

Ser Pro Gln Asn Ala Thr His Ile Lys Pro Met His Pro Thr Ser Val
    50                  55                  60

His Gly Val Glu Asp Met Ile Arg Leu Gly Asp Leu Asn Glu Ala Gly
65                  70                  75                  80

Ile Leu Arg Asn Leu Leu Ile Arg Tyr Arg Asp His Leu Ile Tyr Thr
                85                  90                  95

Tyr Thr Gly Ser Ile Leu Val Ala Val Asn Pro Tyr Gln Leu Leu Ser
            100                 105                 110

Ile Tyr Ser Pro Glu His Ile Arg Gln Tyr Thr Asn Lys Lys Ile Gly
        115                 120                 125

Glu Met Pro Pro His Ile Phe Ala Ile Ala Asp Asn Cys Tyr Phe Asn
```

```
            130                 135                 140
Met Lys Arg Asn Ser Arg Asp Gln Cys Cys Ile Ile Ser Gly Glu Ser
145                 150                 155                 160

Gly Ala Gly Lys Thr Glu Ser Thr Lys Leu Ile Leu Gln Phe Leu Ala
                165                 170                 175

Ala Ile Ser Gly Gln His Ser Trp Ile Glu Gln Val Leu Glu Ala
            180                 185                 190

Thr Pro Ile Leu Glu Ala Phe Gly Asn Ala Lys Thr Ile Arg Asn Asp
                195                 200                 205

Asn Ser Ser Arg Phe Gly Lys Tyr Ile Asp Ile His Phe Asn Lys Arg
    210                 215                 220

Gly Ala Ile Glu Gly Ala Lys Ile Glu Gln Tyr Leu Leu Glu Lys Ser
225                 230                 235                 240

Arg Val Cys Arg Gln Ala Leu Asp Glu Arg Asn Tyr His Val Phe Tyr
                245                 250                 255

Cys Met Leu Glu Gly Met Ser Glu Asp Gln Lys Lys Lys Leu Gly Leu
                260                 265                 270

Gly Gln Ala Ser Asp Tyr Asn Tyr Leu Ala Met Gly Asn Cys Ile Thr
            275                 280                 285

Cys Glu Gly Arg Val Asp Ser Gln Glu Tyr Ala Asn Ile Arg Ser Ala
        290                 295                 300

Met Lys Val Leu Met Phe Thr Asp Thr Glu Asn Trp Glu Ile Ser Lys
305                 310                 315                 320

Leu Leu Ala Ala Ile Leu His Leu Gly Asn Leu Gln Tyr Glu Ala Arg
                325                 330                 335

Thr Phe Glu Asn Leu Asp Ala Cys Glu Val Leu Phe Ser Pro Ser Leu
            340                 345                 350

Ala Thr Ala Ala Ser Leu Leu Glu Val Asn Pro Pro Asp Leu Met Ser
            355                 360                 365

Cys Leu Thr Ser Arg Thr Leu Ile Thr Arg Gly Glu Thr Val Ser Thr
        370                 375                 380

Pro Leu Ser Arg Glu Gln Ala Leu Asp Val Arg Asp Ala Phe Val Lys
385                 390                 395                 400

Gly Ile Tyr Gly Arg Leu Phe Val Trp Ile Val Asp Lys Ile Asn Ala
                405                 410                 415

Ala Ile Tyr Lys Pro Pro Ser Gln Asp Val Lys Asn Ser Arg Arg Ser
            420                 425                 430

Ile Gly Leu Leu Asp Ile Phe Gly Phe Glu Asn Phe Ala Val Asn Ser
        435                 440                 445

Phe Glu Gln Leu Cys Ile Asn Phe Ala Asn Glu His Leu Gln Gln Phe
450                 455                 460

Phe Val Arg His Val Phe Lys Leu Glu Gln Glu Glu Tyr Asp Leu Glu
465                 470                 475                 480

Ser Ile Asp Trp Leu His Ile Glu Phe Thr Asp Asn Gln Asp Ala Leu
                485                 490                 495

Asp Met Ile Ala Asn Lys Pro Met Asn Ile Ile Ser Leu Ile Asp Glu
            500                 505                 510

Glu Ser Lys Phe Pro Lys Gly Thr Asp Thr Thr Met Leu His Lys Leu
        515                 520                 525

Asn Ser Gln His Lys Leu Asn Ala Asn Tyr Ile Pro Pro Lys Asn Asn
    530                 535                 540

His Glu Thr Gln Phe Gly Ile Asn His Phe Ala Gly Ile Val Tyr Tyr
545                 550                 555                 560
```

```
Glu Thr Gln Gly Phe Leu Glu Lys Asn Arg Asp Thr Leu His Gly Asp
                565                 570                 575
Ile Ile Gln Leu Val His Ser Ser Arg Asn Lys Phe Ile Lys Gln Ile
                580                 585                 590
Phe Gln Ala Asp Val Ala Met Gly Ala Glu Thr Arg Lys Arg Ser Pro
                595                 600                 605
Thr Leu Ser Ser Gln Phe Lys Arg Ser Leu Glu Leu Leu Met Arg Thr
                610                 615                 620
Leu Gly Ala Cys Gln Pro Phe Phe Val Arg Cys Ile Lys Pro Asn Glu
625                 630                 635                 640
Phe Lys Lys Pro Met Leu Phe Asp Arg His Leu Cys Val Arg Gln Leu
                645                 650                 655
Arg Tyr Ser Gly Met Met Glu Thr Ile Arg Ile Arg Arg Ala Gly Tyr
                660                 665                 670
Pro Ile Arg Tyr Ser Phe Val Glu Phe Val Glu Arg Tyr Arg Val Leu
                675                 680                 685
Leu Pro Gly Val Lys Pro Ala Tyr Lys Gln Gly Asp Leu Arg Gly Thr
                690                 695                 700
Cys Gln Arg Met Ala Glu Ala Val Leu Gly Thr His Asp Asp Trp Gln
705                 710                 715                 720
Ile Gly Lys Thr Lys Ile Phe Leu Lys Asp His His Asp Met Leu Leu
                725                 730                 735
Glu Val Glu Arg Asp Lys Ala Ile Thr Asp Arg Val Ile Leu Leu Gln
                740                 745                 750
Lys Val Ile Arg Gly Phe Lys Asp Arg Ser Asn Phe Leu Lys Leu Lys
                755                 760                 765
Asn Ala Ala Thr Leu Ile Gln Arg His Trp Arg Gly His Asn Cys Arg
                770                 775                 780
Lys Asn Tyr Gly Leu Met Arg Leu Gly Phe Leu Arg Leu Gln Ala Leu
785                 790                 795                 800
His Arg Ser Arg Lys Leu His Gln Gln Tyr Arg Leu Ala Arg Gln Arg
                805                 810                 815
Ile Ile Gln Phe Gln Ala Arg Cys Arg Ala Tyr Leu Val Arg Lys Ala
                820                 825                 830
Phe Arg His Arg Leu Trp Ala Val Leu Thr Val Gln Ala Tyr Ala Arg
                835                 840                 845
Gly Met Ile Ala Arg Arg Leu His Gln Arg Leu Arg Ala Glu Tyr Leu
850                 855                 860
Trp Arg Leu Glu Ala Glu Lys Met Arg Leu Ala Glu Glu Glu Lys Leu
865                 870                 875                 880
Arg Lys Glu Met Ser Ala Lys Lys Ala Lys Glu Glu Ala Glu Arg Lys
                885                 890                 895
His Gln Glu Arg Leu Ala Gln Leu Ala Arg Glu Asp Ala Glu Arg Glu
                900                 905                 910
Leu Lys Glu Lys Glu Ala Ala Arg Lys Lys Glu Leu Leu Glu Gln
                915                 920                 925
Met Glu Arg Ala Arg His Glu Pro Val Asn His Ser Asp Met Val Asp
930                 935                 940
Lys Met Phe Gly Phe Leu Gly Thr Ser Gly Gly Leu Pro Gly Gln Glu
945                 950                 955                 960
Gly Gln Ala Pro Ser Gly Phe Glu Asp Leu Glu Arg Gly Arg Arg Glu
                965                 970                 975
```

-continued

Met Val Glu Glu Asp Leu Asp Ala Ala Leu Pro Leu Pro Asp Glu Asp
                980                 985                 990

Glu Glu Asp Leu Ser Glu Tyr Lys Phe Ala Lys Phe Ala Ala Thr Tyr
            995                1000                1005

Phe Gln Gly Thr Thr Thr His Ser Tyr Thr Arg Arg Pro Leu Lys
    1010                1015                1020

Gln Pro Leu Leu Tyr His Asp Asp Glu Gly Asp Gln Leu Ala Ala
    1025                1030                1035

Leu Ala Val Trp Ile Thr Ile Leu Arg Phe Met Gly Asp Leu Pro
    1040                1045                1050

Glu Pro Lys Tyr His Thr Ala Met Ser Asp Gly Ser Glu Lys Ile
    1055                1060                1065

Pro Val Met Thr Lys Ile Tyr Glu Thr Leu Gly Lys Lys Thr Tyr
    1070                1075                1080

Lys Arg Glu Leu Gln Ala Leu Gln Gly Glu Gly Glu Ala Gln Leu
    1085                1090                1095

Pro Glu Gly Gln Lys Lys Ser Ser Val Arg His Lys Leu Val His
    1100                1105                1110

Leu Thr Leu Lys Lys Lys Ser Lys Leu Thr Glu Glu Val Thr Lys
    1115                1120                1125

Arg Leu His Asp Gly Glu Ser Thr Val Gln Gly Asn Ser Met Leu
    1130                1135                1140

Glu Asp Arg Pro Thr Ser Asn Leu Glu Lys Leu His Phe Ile Ile
    1145                1150                1155

Gly Asn Gly Ile Leu Arg Pro Ala Leu Arg Asp Glu Ile Tyr Cys
    1160                1165                1170

Gln Ile Ser Lys Gln Leu Thr His Asn Pro Ser Lys Ser Ser Tyr
    1175                1180                1185

Ala Arg Gly Trp Ile Leu Val Ser Leu Cys Val Gly Cys Phe Ala
    1190                1195                1200

Pro Ser Glu Lys Phe Val Lys Tyr Leu Arg Asn Phe Ile His Gly
    1205                1210                1215

Gly Pro Pro Gly Tyr Ala Pro Tyr Cys Glu Glu Arg Leu Arg Arg
    1220                1225                1230

Thr Phe Val Asn Gly Thr Arg Thr Gln Pro Pro Ser Trp Leu Glu
    1235                1240                1245

Leu Gln Ala Thr Lys Ser Lys Lys Pro Ile Met Leu Pro Val Thr
    1250                1255                1260

Phe Met Asp Gly Thr Thr Lys Thr Leu Leu Thr Asp Ser Ala Thr
    1265                1270                1275

Thr Ala Lys Glu Leu Cys Asn Ala Leu Ala Asp Lys Ile Ser Leu
    1280                1285                1290

Lys Asp Arg Phe Gly Phe Ser Leu Tyr Ile Ala Leu Phe Asp Lys
    1295                1300                1305

Val Ser Ser Leu Gly Ser Gly Ser Asp His Val Met Asp Ala Ile
    1310                1315                1320

Ser Gln Cys Glu Gln Tyr Ala Lys Glu Gln Gly Ala Gln Glu Arg
    1325                1330                1335

Asn Ala Pro Trp Arg Leu Phe Phe Arg Lys Glu Val Phe Thr Pro
    1340                1345                1350

Trp His Ser Pro Ser Glu Asp Asn Val Ala Thr Asn Leu Ile Tyr
    1355                1360                1365

Gln Gln Val Val Arg Gly Val Lys Phe Gly Glu Tyr Arg Cys Glu

-continued

```
            1370                1375                1380
Lys Glu Asp Asp Leu Ala Glu Leu Ala Ser Gln Gln Tyr Phe Val
    1385                1390                1395
Asp Tyr Gly Ser Glu Met Ile Leu Glu Arg Leu Leu Asn Leu Val
    1400                1405                1410
Pro Thr Tyr Ile Pro Asp Arg Glu Ile Thr Pro Leu Lys Thr Leu
    1415                1420                1425
Glu Lys Trp Ala Gln Leu Ala Ile Ala Ala His Lys Lys Gly Ile
    1430                1435                1440
Tyr Ala Gln Arg Arg Thr Asp Ala Gln Lys Val Lys Glu Asp Val
    1445                1450                1455
Val Ser Tyr Ala Arg Phe Lys Trp Pro Leu Leu Phe Ser Arg Phe
    1460                1465                1470
Tyr Glu Ala Tyr Lys Phe Ser Gly Pro Ser Leu Pro Lys Asn Asp
    1475                1480                1485
Val Ile Val Ala Val Asn Trp Thr Gly Val Tyr Phe Val Asp Glu
    1490                1495                1500
Gln Glu Gln Val Leu Leu Glu Leu Ser Phe Pro Glu Ile Met Ala
    1505                1510                1515
Val Ser Ser Ser Arg Gly Ala Lys Thr Thr Ala Pro Ser Phe Thr
    1520                1525                1530
Leu Ala Thr Ile Lys Gly Asp Glu Tyr Thr Phe Thr Ser Ser Asn
    1535                1540                1545
Ala Glu Asp Ile Arg Asp Leu Val Val Thr Phe Leu Glu Gly Leu
    1550                1555                1560
Arg Lys Arg Ser Lys Tyr Val Val Ala Leu Gln Asp Asn Pro Asn
    1565                1570                1575
Pro Ala Gly Glu Glu Ser Gly Phe Leu Ser Phe Ala Lys Gly Asp
    1580                1585                1590
Leu Ile Ile Leu Asp His Asp Thr Gly Glu Gln Val Met Asn Ser
    1595                1600                1605
Gly Trp Ala Asn Gly Ile Asn Glu Arg Thr Lys Gln Arg Gly Asp
    1610                1615                1620
Phe Pro Thr Asp Ser Val Tyr Val Met Pro Thr Val Thr Met Pro
    1625                1630                1635
Pro Arg Glu Ile Val Ala Leu Val Thr Met Thr Pro Asp Gln Arg
    1640                1645                1650
Gln Asp Val Val Arg Leu Leu Gln Leu Arg Thr Ala Glu Pro Glu
    1655                1660                1665
Val Arg Ala Lys Pro Tyr Thr Leu Glu Glu Phe Ser Tyr Asp Tyr
    1670                1675                1680
Phe Arg Pro Pro Pro Lys His Thr Leu Ser Arg Val Met Val Ser
    1685                1690                1695
Lys Ala Arg Gly Lys Asp Arg Leu Trp Ser His Thr Arg Glu Pro
    1700                1705                1710
Leu Lys Gln Ala Leu Leu Lys Lys Leu Leu Gly Ser Glu Glu Leu
    1715                1720                1725
Ser Gln Glu Ala Cys Leu Ala Phe Ile Ala Val Leu Lys Tyr Met
    1730                1735                1740
Gly Asp Tyr Pro Ser Lys Arg Thr Arg Ser Val Asn Glu Leu Thr
    1745                1750                1755
Asp Gln Ile Phe Glu Gly Pro Leu Lys Ala Glu Pro Leu Lys Asp
    1760                1765                1770
```

```
Glu Ala Tyr Val Gln Ile Leu Lys Gln Leu Thr Asp Asn His Ile
1775                1780                1785

Arg Tyr Ser Glu Glu Arg Gly Trp Glu Leu Leu Trp Leu Cys Thr
1790                1795                1800

Gly Leu Phe Pro Pro Ser Asn Ile Leu Leu Pro His Val Gln Arg
1805                1810                1815

Phe Leu Gln Ser Arg Lys His Cys Pro Leu Ala Ile Asp Cys Leu
1820                1825                1830

Gln Arg Leu Gln Lys Ala Leu Arg Asn Gly Ser Arg Lys Tyr Pro
1835                1840                1845

Pro His Leu Val Glu Val Glu Ala Ile Gln His Lys Thr Thr Gln
1850                1855                1860

Ile Phe His Lys Val Tyr Phe Pro Asp Asp Thr Asp Glu Ala Phe
1865                1870                1875

Glu Val Glu Ser Ser Thr Lys Ala Lys Asp Phe Cys Gln Asn Ile
1880                1885                1890

Ala Thr Arg Leu Leu Leu Lys Ser Ser Glu Gly Phe Ser Leu Phe
1895                1900                1905

Val Lys Ile Ala Asp Lys Val Leu Ser Val Pro Glu Asn Asp Phe
1910                1915                1920

Phe Phe Asp Phe Val Arg His Leu Thr Asp Trp Ile Lys Lys Ala
1925                1930                1935

Arg Pro Ile Lys Asp Gly Ile Val Pro Ser Leu Thr Tyr Gln Val
1940                1945                1950

Phe Phe Met Lys Lys Leu Trp Thr Thr Thr Val Pro Gly Lys Asp
1955                1960                1965

Pro Met Ala Asp Ser Ile Phe His Tyr Tyr Gln Glu Leu Pro Lys
1970                1975                1980

Tyr Leu Arg Gly Tyr His Lys Cys Thr Arg Glu Glu Val Leu Gln
1985                1990                1995

Leu Gly Ala Leu Ile Tyr Arg Val Lys Phe Glu Glu Asp Lys Ser
2000                2005                2010

Tyr Phe Pro Ser Ile Pro Lys Leu Leu Arg Glu Leu Val Pro Gln
2015                2020                2025

Asp Leu Ile Arg Gln Val Ser Pro Asp Asp Trp Lys Arg Ser Ile
2030                2035                2040

Val Ala Tyr Phe Asn Lys His Ala Gly Lys Ser Lys Glu Glu Ala
2045                2050                2055

Lys Leu Ala Phe Leu Lys Leu Ile Phe Lys Trp Pro Thr Phe Gly
2060                2065                2070

Ser Ala Phe Phe Glu Gln Thr Thr Glu Pro Asn Phe Pro Glu Ile
2075                2080                2085

Leu Leu Ile Ala Ile Asn Lys Tyr Gly Val Ser Leu Ile Asp Pro
2090                2095                2100

Lys Thr Lys Asp Ile Leu Thr Thr His Pro Phe Thr Lys Ile Ser
2105                2110                2115

Asn Trp Ser Ser Gly Asn Thr Tyr Phe His Ile Thr Ile Gly Asn
2120                2125                2130

Leu Val Arg Gly Ser Lys Leu Leu Cys Glu Thr Ser Leu Gly Tyr
2135                2140                2145

Lys Met Asp Asp Leu Leu Thr Ser Tyr Ile Ser Gln Met Leu Thr
2150                2155                2160
```

```
Ala Met Ser Lys Gln Arg Gly Ser Arg Ser Gly Lys
    2165              2170              2175
```

<210> SEQ ID NO 9
<211> LENGTH: 39
<212> TYPE: DNA
<213> ORGANISM: Artificial Sequence
<220> FEATURE:
<223> OTHER INFORMATION: Synthetic Oligonucleotide

<400> SEQUENCE: 9
gcggcggccg ccaccatggt gattcttcag caggggac                         39

<210> SEQ ID NO 10
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 10
gcggctagcg aagttccgca ggtacttgac                                  30

<210> SEQ ID NO 11
<211> LENGTH: 31
<212> TYPE: DNA
<213> ORGANISM: Artificial Sequence
<220> FEATURE:
<223> OTHER INFORMATION: Synthetic Oligonucleotide

<400> SEQUENCE: 11
gcgcttaagc aggtctaact ttctgaagct g                                31

<210> SEQ ID NO 12
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 12
gcgggtacct cacttgccgc tcctggagcc                                  30

<210> SEQ ID NO 13
<211> LENGTH: 41
<212> TYPE: DNA
<213> ORGANISM: Artificial Sequence
<220> FEATURE:
<223> OTHER INFORMATION: Synthetic Oligonucleotide

<400> SEQUENCE: 13
ggcacctagt ggctttgagg taagtatcaa ggttacaaga c                     41

<210> SEQ ID NO 14
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 14
gcggctagct cagaaacgca agagtcttc                                   29

<210> SEQ ID NO 15
<211> LENGTH: 22
<212> TYPE: DNA

-continued

```
<213> ORGANISM: Artificial Sequence
<220> FEATURE:
<223> OTHER INFORMATION: Synthetic Oligonucleotide

<400> SEQUENCE: 15
cttctttgtg cgatgcatca ag                                              22

<210> SEQ ID NO 16
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 16
gcgcttaagc gacgcatgct cgcgatag                                        28

<210> SEQ ID NO 17
<211> LENGTH: 37
<212> TYPE: DNA
<213> ORGANISM: Artificial Sequence
<220> FEATURE:
<223> OTHER INFORMATION: Synthetic Oligonucleotide

<400> SEQUENCE: 17
cgccctcgct ccaggtcctg tggagagaaa ggcaaag                              37

<210> SEQ ID NO 18
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 18
gaacccgaac cggtccttg                                                  19

<210> SEQ ID NO 19
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 19
gcggctagcc cccgggtgcg cggcg                                           25

<210> SEQ ID NO 20
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 20
gcggtcgacg aaacggtcca ggctatgtg                                       29

<210> SEQ ID NO 21
<211> LENGTH: 27
<212> TYPE: DNA
<213> ORGANISM: Artificial Sequence
<220> FEATURE:
<223> OTHER INFORMATION: Synthetic Olligonucleotide

<400> SEQUENCE: 21
gcggcggccg ccccgggtg cgcggcg                                          27
```

<210> SEQ ID NO 22
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 22
gcgcttaagg aaacggtcca ggctatgtg                              29

<210> SEQ ID NO 23
<211> LENGTH: 40
<212> TYPE: DNA
<213> ORGANISM: Artificial Sequence
<220> FEATURE:
<223> OTHER INFORMATION: Synthetic Oligonucleotide

<400> SEQUENCE: 23
caggcaccta gtggctttga ggtaccaggc tagggacagg                  40

<210> SEQ ID NO 24
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 24
gcggctagcc gcctgagccc agaagttc                               28

<210> SEQ ID NO 25
<211> LENGTH: 38
<212> TYPE: DNA
<213> ORGANISM: Artificial Sequence
<220> FEATURE:
<223> OTHER INFORMATION: Synthetic Oligonucleotide

<400> SEQUENCE: 25
cgccctcgct ccaggtcctg aaggagacaa gaggtatg                    38

<210> SEQ ID NO 26
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 26
gcgcttaagc accgcttgtg ttgatcctc                              29

<210> SEQ ID NO 27
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 27
gccagggaag gatcccatg                                         19

<210> SEQ ID NO 28
<211> LENGTH: 57
<212> TYPE: DNA
<213> ORGANISM: Artificial Sequence
<220> FEATURE:

```
<223> OTHER INFORMATION: Synthetic Oligonucleotide

<400> SEQUENCE: 28
gcgggtacct catgcgtaat ccggtacatc gtaagggtac ttgccgctcc tggagcc        57

<210> SEQ ID NO 29
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 29
agcttcgtag agtttgtgga gcgg                                            24

<210> SEQ ID NO 30
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 30
gaggggcaaa caacagatg                                                  19
```